(12) United States Patent
Gao et al.

(10) Patent No.: US 12,036,319 B2
(45) Date of Patent: Jul. 16, 2024

(54) POLYVALENT STING ACTIVATING COMPOSITIONS AND USES THEREOF

(71) Applicant: The Board of Regents of the University of Texas System, Austin, TX (US)

(72) Inventors: Jinming Gao, Dallas, TX (US); Suxin Li, Dallas, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 178 days.

(21) Appl. No.: 17/469,111

(22) Filed: Sep. 8, 2021

(65) Prior Publication Data

US 2022/0071903 A1    Mar. 10, 2022

Related U.S. Application Data

(60) Provisional application No. 63/075,560, filed on Sep. 8, 2020.

(51) Int. Cl.
| | | |
|---|---|---|
| *A61K 9/107* | (2006.01) | |
| *A61K 31/4184* | (2006.01) | |
| *A61K 31/5377* | (2006.01) | |
| *A61K 31/7076* | (2006.01) | |
| *A61K 47/32* | (2006.01) | |
| *A61P 35/00* | (2006.01) | |

(52) U.S. Cl.
CPC ........ *A61K 9/1075* (2013.01); *A61K 31/4184* (2013.01); *A61K 31/5377* (2013.01); *A61K 31/7076* (2013.01); *A61K 47/32* (2013.01); *A61P 35/00* (2018.01)

(58) Field of Classification Search
None
See application file for complete search history.

(56) References Cited

U.S. PATENT DOCUMENTS

| 9,724,408 | B2 | 8/2017 | Dubensky, Jr. et al. |
|---|---|---|---|
| 10,131,686 | B2 | 11/2018 | Patel et al. |
| 10,633,411 | B2 | 4/2020 | Chen et al. |
| 11,873,319 | B2 | 1/2024 | Vance et al. |
| 2016/0287623 | A1 | 10/2016 | Gajewski et al. |
| 2018/0344758 | A1 | 12/2018 | Li et al. |
| 2020/0330556 | A1* | 10/2020 | Pesiridis .............. A61K 38/217 |

FOREIGN PATENT DOCUMENTS

| EP | EP 2934598 | 4/2018 |
|---|---|---|
| WO | WO 2017/151922 | 9/2017 |
| WO | WO 2018/100558 | 6/2018 |
| WO | WO 2019/161171 | 8/2019 |
| WO | WO 2020/263733 | 12/2020 |

OTHER PUBLICATIONS

Li et al., "Prolonged activation of innate immune pathways by a polyvalent STING agonist," *Nature Biomedical Engineering*, 5:455-466, 2021.
Luo et al., "A STING-activating nanovaccine for cancer immunotherapy," *Nature Nanotechnology*, 12:648, 2017.
PCT International Search Report and Written Opinion issued in International Application No. PCT/US2021/049365, dated Dec. 22, 2021.
Burdette et al., "STING is a direct innate immune sensor of cyclic di-GMP," *Nature*, 478(7370):515-518, 2011.
He et al., "Self-assembled cGAMP-STINGΔTM signaling complex as a bioinspired platform for cGAMP delivery," *Sci. Adv.*, 6:eaba7589, 2020.
Marloye et al., "Current patent and clinical status of stimulator of interform genes (STING) agonists for cancer immunotherapy," *Pharm. Pat. Anal.*, 8(4):87-90, 2019.
Motedayen Aval et al., "Challenges and opportunities in the clinical development of STING agonists fro cancer immunotherapy," *J. Clin. Med.*, 9:3323, 2020.
Shae et al., "Endosomolytic polymersomes increase the activity of cyclic dinucleotide STING agonsits to enhance cancer immunothereapy," *Nature Nanotechnology*, 14:269-278, 2019.
Shu et al., "Structure of STING bound to cyclic di-GMP reveals the mechanism of cyclic dinucleotide recognition by the immune system," *Nat Struct Mol Biol.*, 19(7):722-724, 2012.
Yin et al., "Cyclic di-GMP sensing via the innate immune signaling protein STING," *Mol Cell.*, 46(6):735-745, 2012.
Zhang et al., "Cyclic GMP-AMP containing mixed phosphodiester linkages is an endogenous high affinity ligand for STING," *Mol Cell.*, 51(2):226-235, 2013.

* cited by examiner

*Primary Examiner* — Brian J Davis
(74) *Attorney, Agent, or Firm* — Parker Highlander PLLC

(57) ABSTRACT

Described herein are therapeutic pH responsive compositions useful for the treatment of cancer. The compositions involve combining a STING activating polymer micelle, such as PC7A, with a non-peptide STING agonist, such as cGAMP. Methods of administering these compositions in the treatment of cancer are also disclosed. These methods include administration of the pharmaceutical compositions by intratumoral injection in the treatment of solid tumors.

20 Claims, 17 Drawing Sheets
(17 of 17 Drawing Sheet(s) Filed in Color)
Specification includes a Sequence Listing.

SEQUENCE LISTING

```
<160> NUMBER OF SEQ ID NOS: 18

<210> SEQ ID NO 1
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 1
atgagtggtg gttgcaggc                                                  19

<210> SEQ ID NO 2
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 2
tgacctttca aatgcagtag attca                                           25

<210> SEQ ID NO 3
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 3
ggagtgaagc cacgcacac                                                  19
```

```
<210> SEQ ID NO 4
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 4
atggagagag gctctctgct gt                                               22

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
agtctaaaca gcgcccggta                                                  20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
ggtcgggtgt agtttgagga                                                  20

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 7
tgatgagagg gaggccattt g                                                21

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 8
tctcctttgg ggtgagtctg t                                                21

<210> SEQ ID NO 9
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 9
acacccgcca ccagttcgc                                                   19

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide
```

```
<400> SEQUENCE: 10
atggggtact tcagggtcag gata                                              24

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
gtctcctcca aattgctctc                                                   20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
acaggagctt ctgacactga                                                   20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
tggcattcaa ggagtacctc                                                   20

<210> SEQ ID NO 14
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 14
ttgtagcaat gatctcaaca cg                                                22

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
ggacttcgag caagagatgg                                                   20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
aggaaggaag gctggaagag                                                   20

<210> SEQ ID NO 17
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 17
atgacatcaa gaaggtggtg                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
cataccagga aatgagcttg                                              20
```

POLYVALENT STING ACTIVATING COMPOSITIONS AND USES THEREOF

This application claims the benefit of priority to U.S. Provisional Application No. 63/075,560, filed on Sep. 8, 2020, the entire contents of which are hereby incorporated by reference.

STATEMENT AS TO FEDERALLY SPONSORED RESEARCH

This invention was made with government support under grant numbers U54 CA244719, R01 CA216839, and U01 CA218422 awarded by the National Institutes of Health. The government has certain rights in the invention.

BACKGROUND OF THE INVENTION

Multifunctional nanoparticles have received attention in a wide range of applications such as biosensors, diagnostic nanoprobes and targeted drug delivery systems. These efforts have been driven to a large extent by the need to improve biological specificity with reduced side effects in diagnosis and therapy through the precise, spatiotemporal control of agent delivery in various physiological systems. In order to achieve this goal, efforts have been dedicated to develop stimuli-responsive nanoplatforms. Environmental stimuli that have been exploited for pinpointing the delivery efficiency include pH, temperature, enzymatic expression, redox reaction and light induction. Among these activating signals, pH trigger is one of the most extensively studied stimuli based on two types of pH differences: (a) pathological (e.g. tumor) vs. normal tissues and (b) acidic intracellular compartments. For example, due to the unusual acidity of the tumor extracellular microenvironment (pH~6.5), several pH-responsive nano systems have been reported to increase the efficacy of therapy.

The stimulator of interferon genes (STING) plays a central role in innate immunity during infection and cancer. STING is endogenously activated by 2',3'-cyclic-GMP-AMP (cGAMP), a cyclic dinucleotide synthesized by cGAMP synthase (cGAS) in response to cytosolic DNA as a danger signal. Activation of STING mediates a multifaceted type I interferon (IFN-I) response that promotes the maturation and migration of dendritic cells, and primes cytotoxic T lymphocytes and nature killer cells for spontaneous immune responses. In recent years, STING has emerged as an important target that activates antitumor immune pathways for cancer immunotherapy. Studies have observed punctate structures upon the addition of cGAMP to STING, indicating that oligomerization or even higher order architecture may be critical for activation. Therapeutic attempts to deliver cGAMP into the cytosol of target cells, where STING is located, have been limited by its inherent properties as a small, dual negatively charged molecule. Moreover, the rapid enzymatic degradation and clearance as well as off-target toxicity of cGAMP have hindered its further clinical application. Therefore, the pharmaceutical industry has devoted great efforts to the chemical modification of natural cyclic dinucleotides (CDNs) as well as novel STING agonists to improve their bioavailability and pharmacological activity.

pH sensitive polymers with linear or cyclic tertiary amine structures, have shown strong vaccine adjuvant effect through the STING-dependent pathway. Moreover, some pH sensitive polymers, (e.g. 7-membered cyclic amine, PC7A) can function as polyvalent STING agonists. These pH sensitive polymers can act through polymer-induced phase separation of STING for innate immune activation with more prolonged cytokine expressions than cGAMP. Moreover, a combination of polyvalent STING activation by a pH sensitive polymer, (e.g. PC7A) with cytosol delivered or cell-intrinsic cGAMP stimulation further offers a synergistic and robust strategy to mount antitumor immunity for cancer immunotherapy.

SUMMARY OF THE INVENTION

In some aspects, the present disclosure provides pharmaceutical compositions which may be used to generate an immune response. These pharmaceutical compositions may activate the STING and/or the interferon receptor pathways in vivo leading to an enhanced immunoresponse. These compositions may be used in the treatment of various diseases and disorders such as cancer In certain embodiments, provided herein is a pharmaceutical composition comprising:
(i) a block copolymer of Formula (I), or a pharmaceutically acceptable salt, solvate, or hydrate thereof:

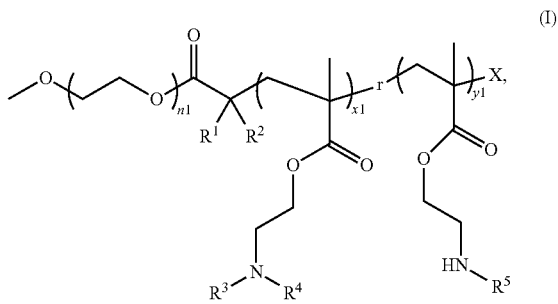

wherein:
  $n_1$ is an integer from 10-200;
  $x_1$ is an integer from 20-300;
  $y_1$ is an integer from 0-10;
  X is a halogen, —OH, or —C(O)OH;
  r denotes randomness in the order of $x_1$ and $y_1$ blocks in the block copolymer;
  $R^1$ and $R^2$ are each independently hydrogen or optionally substituted $C_1$-$C_6$ alkyl;
  $R^3$ and $R^4$ are each independently an optionally substituted $C_1$-$C_6$ alkyl, $C_3$-$C_{10}$ cycloalkyl or aryl;
  or $R^3$ and $R^4$ are taken together with the corresponding nitrogen to which they are attached form an optionally substituted 5 to 7-membered ring;
  $R^5$ is hydrogen or —C(O)CH$_3$; and
(ii) a non-peptide STING agonist.

In some embodiments, the of the block copolymer of Formula (I), $R^1$ and $R^2$ are each independently an optionally substituted $C_1$-$C_6$ alkyl. In some embodiments, $R^1$ and $R^2$ are each independently —CH3. In some embodiments, $R^3$ and $R^4$ are each independently an optionally substituted C1-C6 alkyl. In some embodiments, $R^3$ and $R^4$ are each independently —CH$_2$CH$_3$, —CH$_2$CH$_2$CH$_3$, or —CH$_2$CH$_2$CH$_2$CH$_3$. In some embodiments, $R^3$ and $R^4$ are taken together with the corresponding nitrogen to which they are attached form an optionally substituted 5 to 7-membered ring. In some embodiments, $R^3$ and $R^4$ taken together are —CH$_2$(CH$_2$)$_2$CH$_2$—, —CH$_2$(CH$_2$)$_3$CH$_2$—, or —CH$_2$(CH$_2$)$_4$CH$_2$—. In some embodiments, $R^5$ is hydrogen. In some embodiments, $R^5$ is —C(O)CH$_3$. In some embodiments, the non-peptide STING agonist is a cyclic dinucleotide. In some embodiments, the cyclic dinucleotide is cGAMP.

In another aspect of the invention is a method for treating cancer in a subject in need thereof, comprising administration to the subject a pharmaceutically effective amount of the pharmaceutical composition comprising a non-peptide STING agonist as described herein. In some embodiments, the cancer comprises a solid tumor. In some embodiments, the tumor is of a cancer, wherein the cancer is of the breast, ovarian, prostate, peritoneal metastasis, colorectal, bladder, esophageal, head and neck (HNSCC), lung, brain, kidney, or skin (including melanoma and sarcoma).

In another aspect of the invention is a method of activating the STING pathway in a subject comprising administering to the subject in need thereof a pharmaceutical composition comprising a non-peptide STING agonist as described herein.

Other objects, features and advantages of the block copolymers, micelle compositions, and methods described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The patent application file contains at least one drawing executed in color. Copies of this patent application publication with color drawing(s) will be provided by the Office upon request and payment of the necessary fee.

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings below.

DETAILED DESCRIPTION OF THE INVENTION

Figure 1:
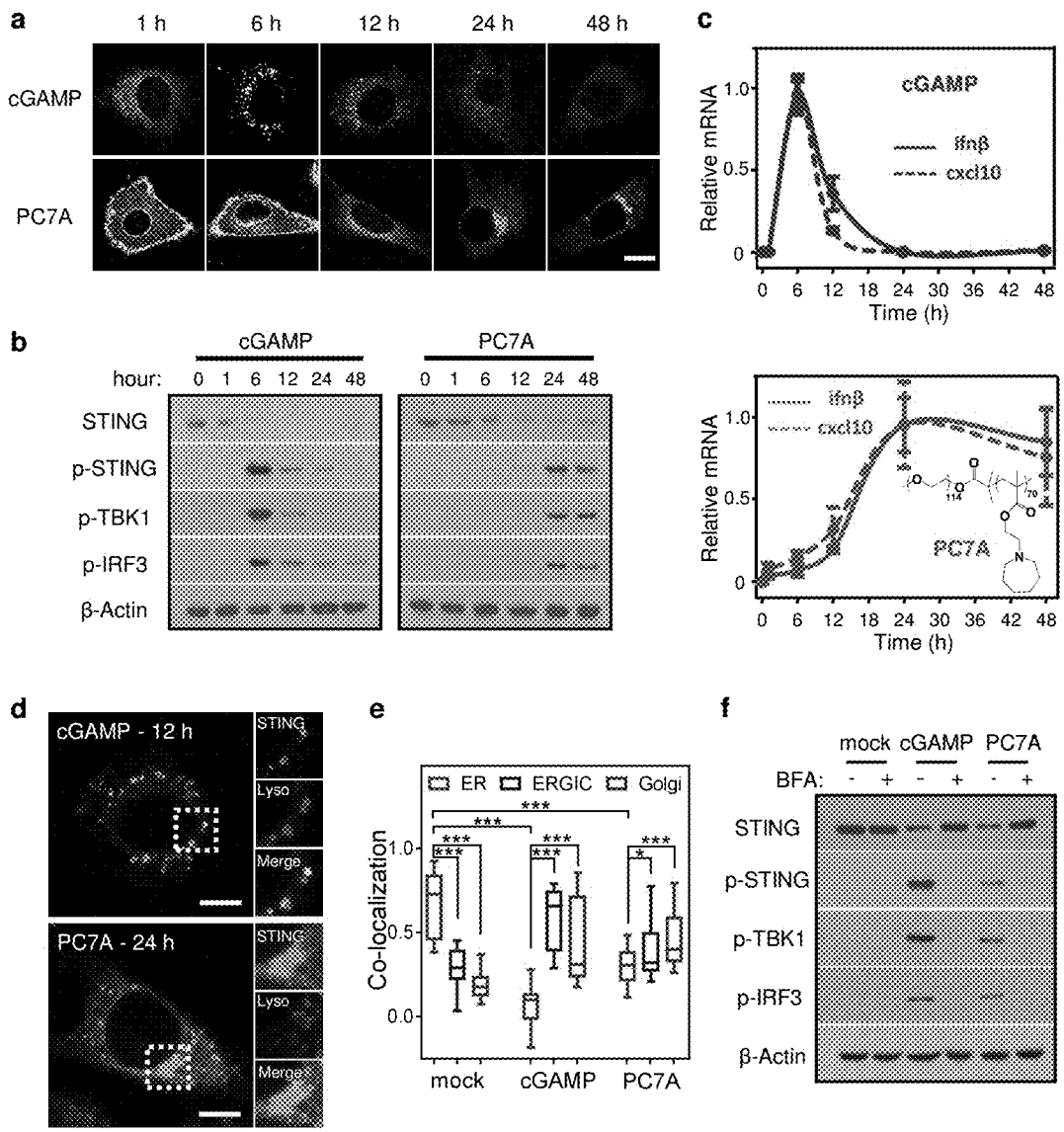
FIG. 1 shows that PC7A polymer activates STING with a spatiotemporal profile distinct from cGAMP. a, MEF cells primed by cGAMP or PC7A exhibit different geometric and temporal patterns of GFP-STING punctate formation and depletion. Cells were first incubated with cGAMP (10 µM, PEI was used for cytosolic delivery) or PC7A micelles (10 µM) for 1 h, then media was exchanged and cells were incubated for indicated periods prior to imaging. Scale bar, 10 µm. b, THP1 cells treated with cGAMP display a burst effect of TBK1/IRF3 phosphorylation followed by rapid STING degradation, while treatment by PC7A leads to sustained TBK1/IRF3 phosphorylation and slower STING degradation. c, Relative ifn-0 and cxcl10 mRNA levels show slower but prolonged STING activation in THP1 cells by PC7A compared to cGAMP. Values are mean±SD, n=3. d, STING-GFP colocalizes with lysosomes in MEFs 12 h after cGAMP treatment, supporting rapid degradation. In contrast, PC7A inhibits lysosomal degradation of GFP-STING, as indicated by lack of colocalization and persistent GFP fluorescence. Scale bar, 5 µm. e, cGAMP and PC7A induce similar STING translocation from ER to ERGIC and Golgi apparatus. Colocalization was quantified by Pearson's correlation coefficient. Box and whisker, ±min/max, n=20. Two-tailed Student's t-test: *, P<0.05; ***, P<0.001. f, STING translocation is necessary for downstream signaling as BFA, an inhibitor of protein transport from ER to Golgi, prevents phosphorylation of TBK1/IRF3 by cGAMP or PC7A.

Provided herein are pharmaceutical compositions comprising a block copolymer and a non-peptide STING agonist. In some embodiments, the block copolymer is a diblock copolymer. In some embodiments, the block copolymer forms a micelle encapsulating the non-peptide STING agonist.

I. Compositions

In certain embodiments, provided herein is a pharmaceutical compositing comprising:
(i) a block copolymer of Formula (I), or a pharmaceutically acceptable salt, solvate, or hydrate thereof:

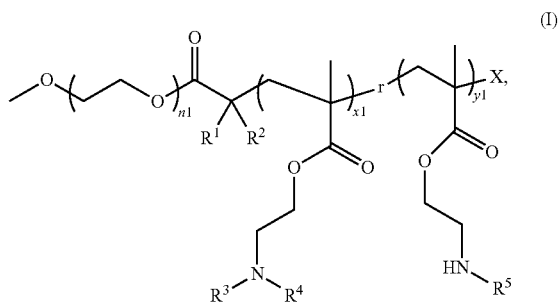

wherein:
$n_1$ is an integer from 10-200;
$x_1$ is an integer from 20-300;
$y_1$ is an integer from 0-10;
r denotes randomness in the order of $x_1$ and $y_1$ blocks in the block copolymer;
X is a halogen, —OH, or —C(O)OH;
$R^1$ and $R^2$ are each independently hydrogen or optionally substituted $C_1$-$C_6$ alkyl;
$R^3$ and $R^4$ are each independently an optionally substituted $C_1$-$C_6$ alkyl, $C_3$-$C_{10}$ cycloalkyl or aryl;
or $R^3$ and $R^4$ are taken together with the corresponding nitrogen to which they are attached form an optionally substituted 5 to 7-membered ring;
$R^5$ is hydrogen or —C(O)CH$_3$; and
(ii) a non-peptide STING agonist.

(i) Block Copolymers

In some embodiments, the pharmaceutical composition comprises a block copolymer of Formula (I), or a pharmaceutically acceptable, salt, solvate, or hydrate thereof.

In some embodiments of Formula (I), $R^1$ and $R^2$ are each independently an optionally substituted $C_1$-$C_6$ alkyl. In some embodiments, $R^1$ and $R^2$ are each independently —CH$_3$, —CH$_2$CH$_3$, —CH$_2$CH$_2$CH$_3$, or —CH$_2$CH$_2$CH$_2$CH$_3$. In some embodiments, $R^1$ and $R^2$ are each independently —CH$_3$. In some embodiments, $R^1$ and $R^2$ are each independently hydrogen.

In some embodiments of Formula (I), the $R^3$ and $R^4$ are each independently an optionally substituted $C_1$-$C_6$ alkyl. In some embodiments, the alkyl is a straight chain or a branch alkyl. In some embodiments, the alkyl is a straight chain alkyl. In some embodiments, $R^3$ and $R^4$ are each independently —CH$_2$CH$_3$, —CH$_2$CH$_2$CH$_3$, or —CH$_2$CH$_2$CH$_2$CH$_3$. In some embodiments, $R^3$ and $R^4$ are each independently —CH$_2$CH$_2$CH$_2$CH$_3$.

In some embodiments, the alkyl is a branched alkyl. In some embodiments, $R^3$ and R4 are each independently —CH(CH$_3$)$_2$ or —CH(CH$_3$)CH$_2$CH$_3$. In some embodiments, $R^3$ and R4 are each independently —CH(CH$_3$)$_2$.

In some embodiments of the block copolymer of Formula (I), $R^3$ and $R^4$ are each independently an optionally substituted $C_3$-$C_{10}$ cycloalkyl or aryl. In some embodiments, $R^3$ and $R^4$ are each independently an optionally substituted cyclopropyl, cyclobutyl, cyclopentyl, cyclohexyl, or cycloheptyl. In some embodiments, $R^3$ and $R^4$ are each independently an optionally substituted phenyl.

In some embodiments of the block copolymer of Formula (I), $R^3$ and $R^4$ are taken together with the corresponding nitrogen to which they are attached form an optionally substituted 5 to 7-membered ring. In some embodiments, $R^3$ and $R^4$ taken together are —CH$_2$(CH$_2$)$_2$CH$_2$—, —CH$_2$(CH$_2$)$_3$CH$_2$—, or —CH$_2$(CH$_2$)$_4$CH$_2$—. In some embodiments, $R^3$ and $R^4$ taken together are —CH$_2$(CH$_2$)$_2$CH$_2$—. In some embodiments, $R^3$ and $R^4$ taken together are —CH$_2$(CH$_2$)$_3$CH$_2$—. In some embodiments, $R^3$ and $R^4$ taken together are —CH$_2$(CH$_2$)$_4$CH$_2$—.

In some embodiments of the block copolymer of Formula (I), $R^5$ is hydrogen. In some embodiments, $R^5$ is —C(O)CH$_3$. In some embodiments, $R^5$ is acetyl.

In some embodiments of the block copolymer of Formula (I), $y_1$, is an integer 1-10, 1-9, 1-8, 1-7, 1-6, 1-5, 1-4, 1-3, 1-2, or any range derivable therein. In some embodiments, $y_1$, is 1, 2, 3, 4, 5, 6, 7, 8, or 9. In some embodiments, $y_1$, is 1, 2, or 3. In some embodiments, $y_1$, is 0.

In some embodiments, the block copolymer of Formula (I) has the structure of Formula (Ia), or a pharmaceutically acceptable salt, solvate, or hydrate thereof:

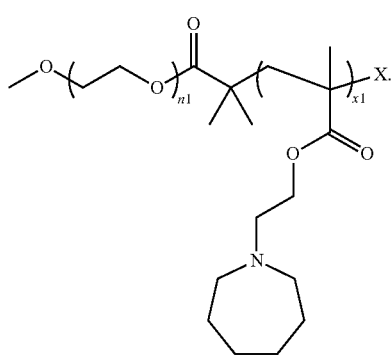

(Ia)

In some embodiments, the block copolymer is a diblock copolymer. In some embodiments, the block copolymer comprises a hydrophilic polymer segment and a hydrophobic segment.

In some embodiments, the hydrophilic polymer segment comprises poly(ethylene oxide) (PEO). In some embodiments, the hydrophilic polymer segment is about 2 kD to about 10 kD in size. In some embodiments, the hydrophilic polymer segment is about 2 kD to about 5 kD in size. In some embodiments, the hydrophilic polymer segment is about 3 kD to about 8 kD in size. In some embodiments, the hydrophilic polymer segment is about 4 kD to about 6 kD in size. In some embodiments, the hydrophilic polymer segment is about 5 kD in size.

In some embodiments, $n_1$ is an integer from 1-5, 5-10, 10-15, 15-20, 20-25, 25-30, 30-35, 35-40, 40-45, 45-50, 50-55, 55-60, 60-65, 65-70, 70-75, 75-80, 80-85, 85-90, 90-95, 95-99, 100-109, 110-119, 120-129, 130-139, 140-149, 150-159, 160-169, 170-179, 180-189, 190-199 or any range derivable therein. In some embodiments, $n_1$ is an integer from 60-150, 100-140, or 110-120. In some embodiments, $n_1$ is 100-140.

In some embodiments, the block copolymer comprises a hydrophobic polymer segment. In some embodiments, the hydrophobic polymer segment is selected from:

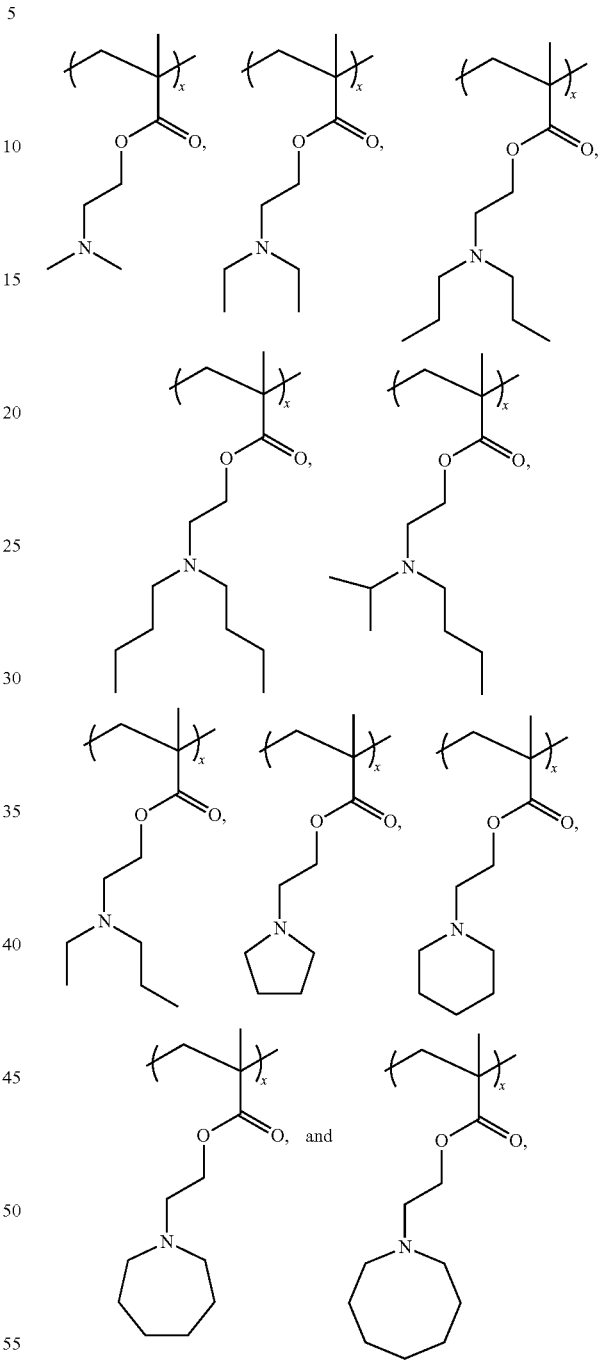

wherein x is about 20-300 in total.

In some embodiments, the hydrophobic segment comprises a dibutyl amine. In some embodiments, the hydrophobic segment comprises a cyclic amine. In some embodiments, the cyclic amine is a 5 to 8-membered cyclic amine. In some embodiments, the cyclic amine is a 7-membered cyclic amine (PC7A). In some embodiments, the hydrophobic segment comprises

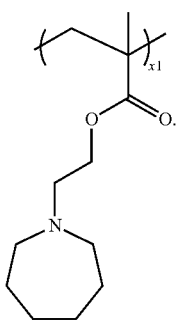

In some embodiments, $x_1$, is an integer 1-5, 5-10, 10-15, 15-20, 20-25, 25-30, 30-35, 35-40, 40-45, 45-50, 50-55, 55-60, 60-65, 65-70, 70-75, 75-80, 80-85, 85-90, 90-95, 95-99, 100-109, 110-119, 120-129, 130-139, 140-149, 150-159, 160-169, 170-179, 180-189, 190-199 or any range derivable therein. In some embodiments, $x_1$ is an integer from 50-200, 60-160, or 90-140. In some embodiments, $x_1$ is 90-140.

In some embodiments, X is a terminal group. In some embodiments, the terminal capping group is the product of an atom transfer radical polymerization (ATRP) reaction. For example, the terminal capping group may be a halogen, such as —Br, when atom transfer radical polymerization (ATRP) is used. In some embodiments, X is Br. In some embodiments, X is independently —OH. In some embodiments, each X is an acid. In some embodiments, X is —C(O)OH. In some embodiments, X is H. The end group may optionally be further modified following polymerization with an appropriate moiety.

(ii) Non-Peptide STING Agonists

In some embodiments, the non-peptide STING agonist is a small molecule. In some embodiments, the non-peptide STING agonist is a dinucleotide. In some embodiments, the non-peptide STING agonist is a synthetic cyclic dinucleotide (CDN). In some embodiments, the CDN is naturally occurring or synthetic CDN. The CDN can be modified as the 2' hydroxyl or at the 4' hydroxyl site. In some instances, the CDN the 2' hydroxyl group in a locked or bridged ribose modification (e.g., locked nucleic acid or LNA) in which the oxygen molecule bound at the 2' carbon is linked to the 4' carbon by a methylene group, thus forming a 2'-C,4'-C-oxymethylene-linked bicyclic ribonucleotide monomer.

In some embodiments, the cyclic dinucleotide has the structure of Formula (IIa) or Formula (IIb), or a pharmaceutically acceptable salt, solvate, or hydrate thereof:

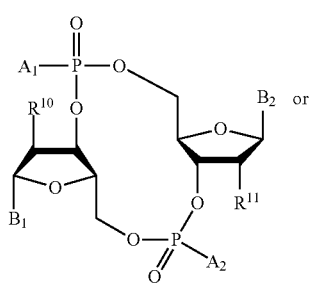

(IIa)

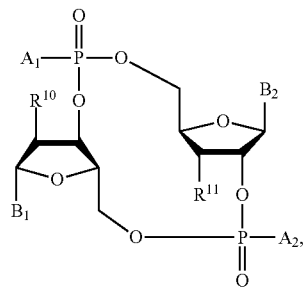

(IIb)

wherein:

$A^1$ and $A^2$ are each independently OH or SH;

B1 and $B^2$ are each independently guanine or adenine; and $R^{10}$ is H, halogen, OH, $OCH_3$; and $R^{11}$ is halogen or OH.

In some embodiments of Formula (IIa) or (IIb), or a pharmaceutically acceptable salt, solvate or hydrate thereof, $R^{10}$ is OH or $OCH_3$. In some embodiments, $R^{10}$ is fluoro or chloro. In some embodiments, $R^{11}$ is OH. In some embodiments, $R^{11}$ is fluoro or chloro. In some embodiments, $A^1$ and $A^2$ are each independently OH. In some embodiments, $A^1$ and $A^2$ are each independently SH. In some embodiments, $B^1$ and $B^2$ are each independently guanine. In some embodiments, B1 and $B^2$ are each independently adenine. In some embodiments, one of $B^1$ or $B^2$ is guanine and the other is adenine.

In some embodiments, the cyclic dinucleotide of Formula (IIa) has the structure of Formula (IIa)(1), or a pharmaceutically acceptable salt, solvate, or hydrate thereof:

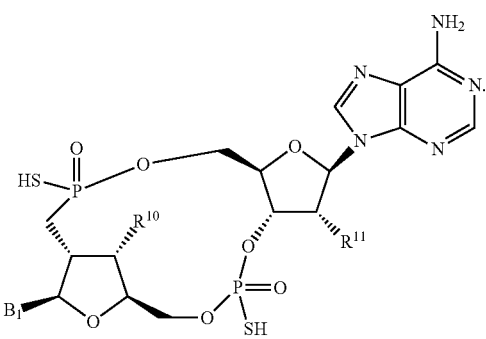

(IIa-1)

In some embodiments, the cyclic dinucleotide has the structure of Formula (III), or a pharmaceutically acceptable salt, solvate, or hydrate thereof:

In some embodiments the cyclic dinucleotide is a compound selected from:

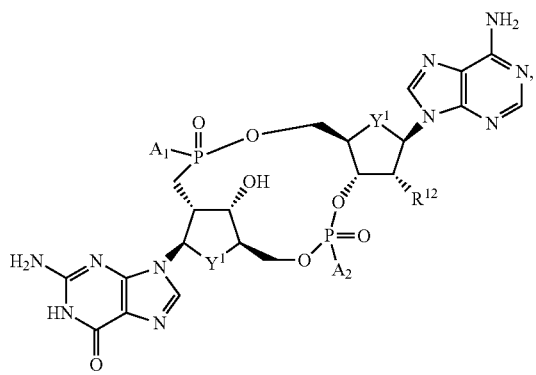

(III)

wherein:
A¹ and A² are each independently OH or SH; and
Y¹ and Y² are each independently —CH— or —O—.

In some embodiments of Formula (III), or a pharmaceutically acceptable salt, solvate or hydrate thereof, A¹ and A² are each independently OH. In some embodiments, A¹ and A² are each independently SH. In some embodiments, Y¹ and Y² are each independently —O—. In some embodiments, Y¹ and Y² are each independently —CH—. In some embodiments, one of Y¹ or Y² is —O— while the other is —CH—.

Naturally occurring cyclic dinucleotides include CDG, CDA, 3',3'-cGAMP and 2',3'-cGAMP. In some embodiments, the cyclic dinucleotide is cyclic guanosine monophosphate-adenosine monophosphate (cyclic GMP-AMP or cGAMP), or a pharmaceutically acceptable salt, solvate, or hydrate. cGAMP functions as an endogenous second messenger inducing STING-dependent type I interferon response. cGAMP has also been shown to be an effective adjuvant that boosts the production of antigen-specific antibodies and T cell responses in mice. In some embodiments, cGAMP is 2',3'-cGAMP. In some embodiments, cGAMP has the following structure, or a pharmaceutically acceptable salt, solvate, of hydrate thereof:

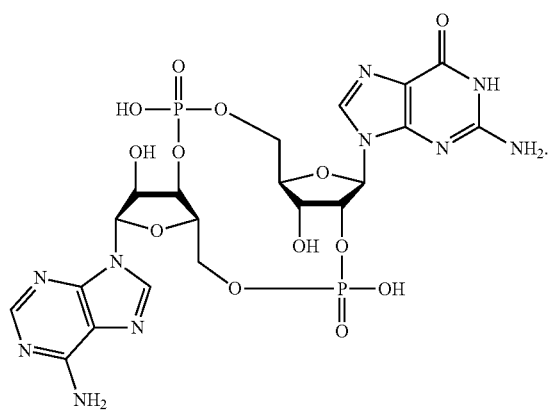

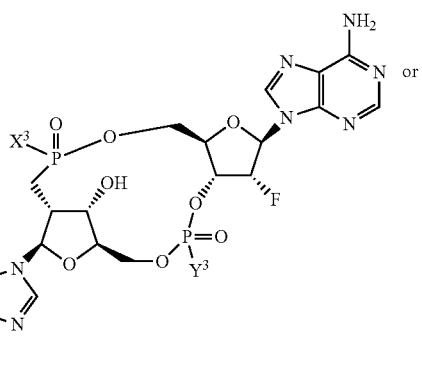

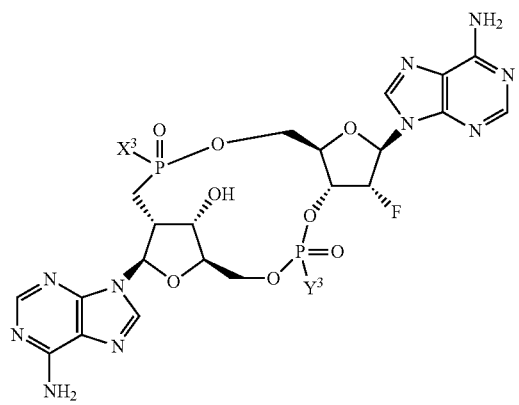

wherein X³ and Y³ are each independently OH, SH, or BH₃; or a pharmaceutically acceptable salt, solvate, or hydrate thereof.

In some embodiments the cyclic dinucleotide is a compound selected from:

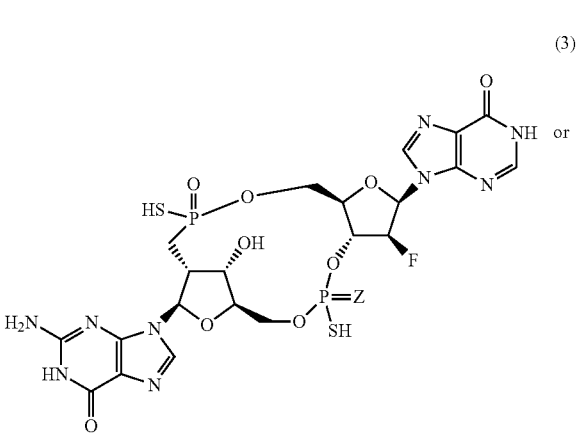

(3)

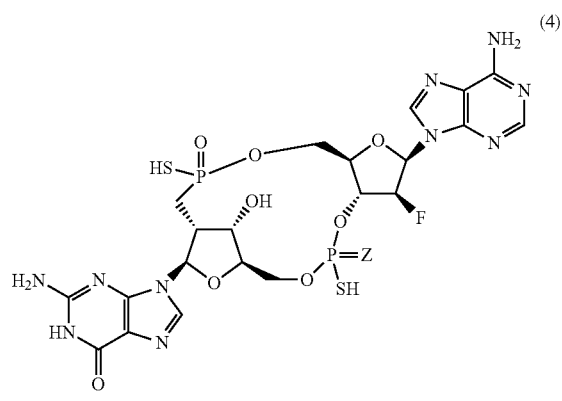 (4)
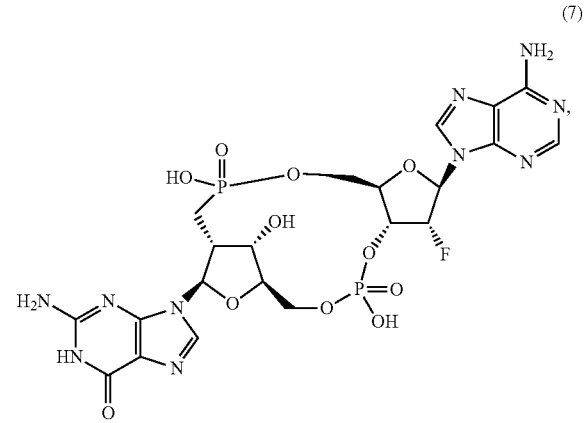 (7)
wherein Z is O or S; or a pharmaceutically acceptable salt, solvate, or hydrate thereof.
In some embodiments the cyclic dinucleotide is a compound selected from:
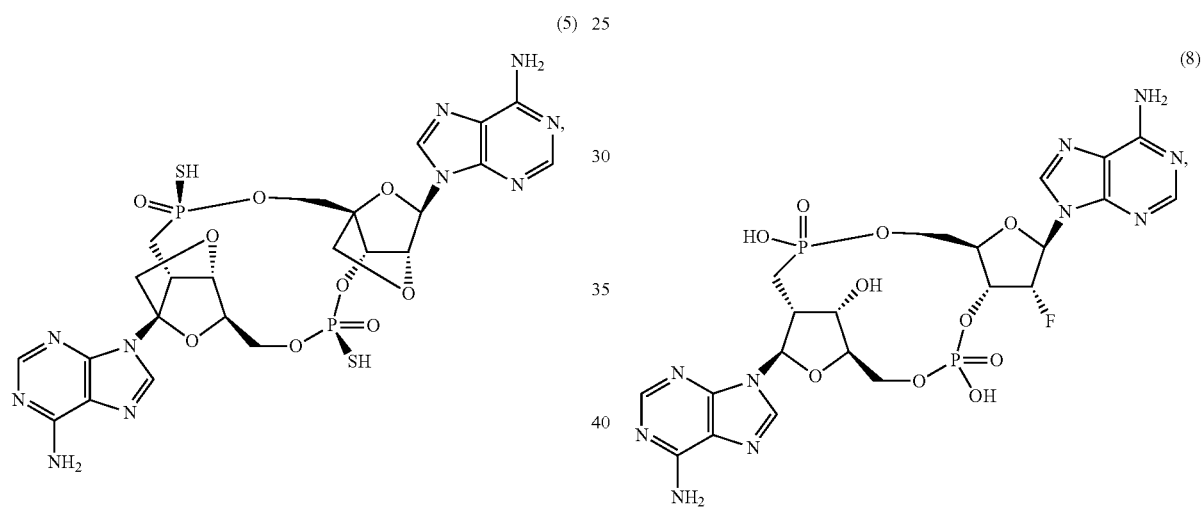
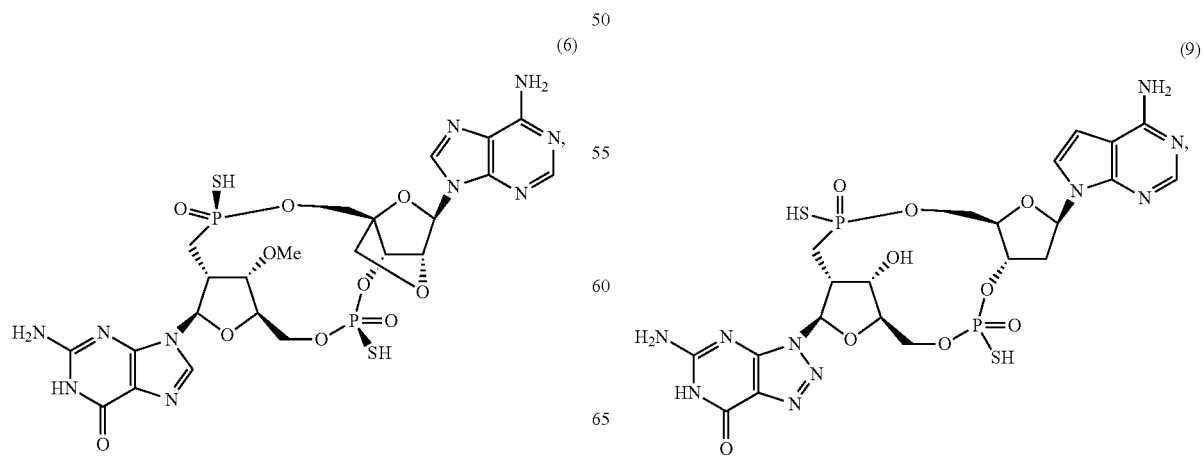

(10)
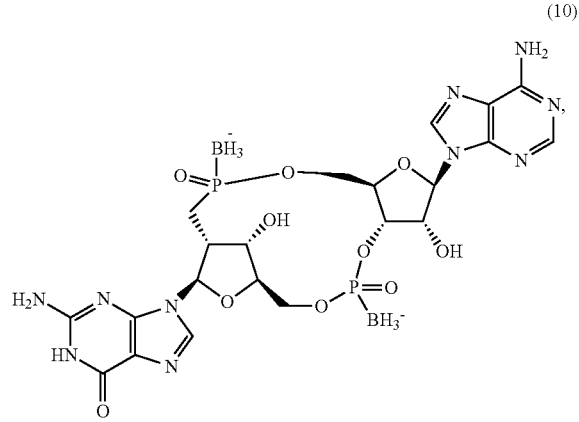
(11)
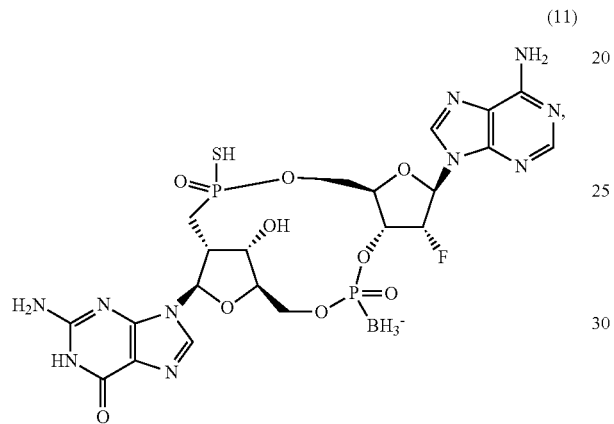
(12)
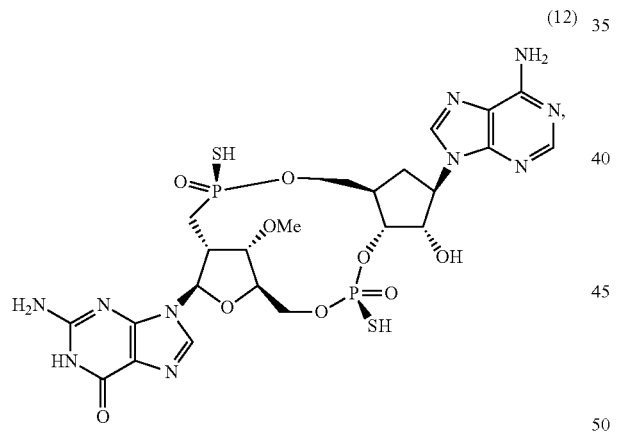
(13)
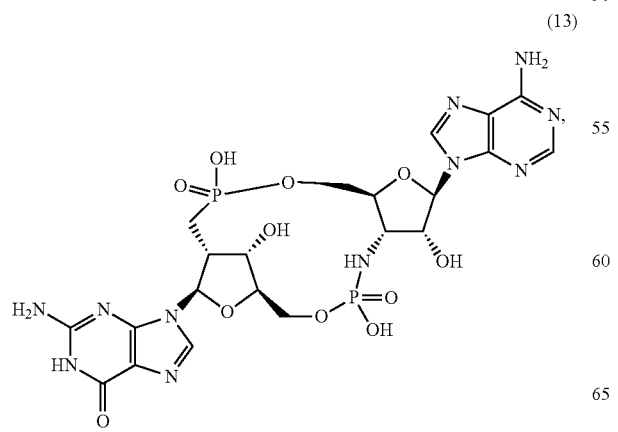
(14)
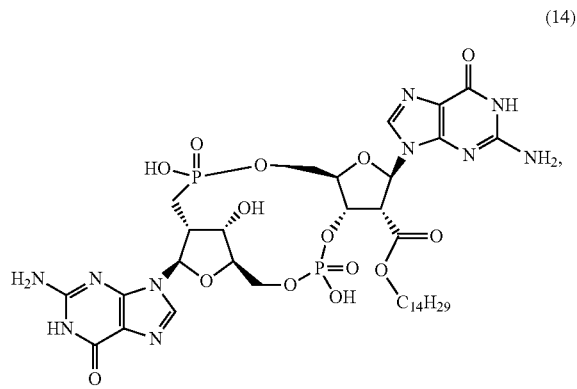
(15)
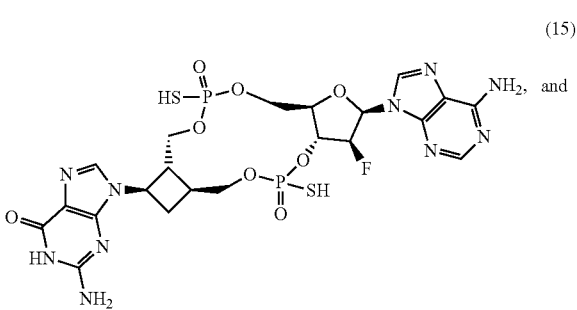
(16)
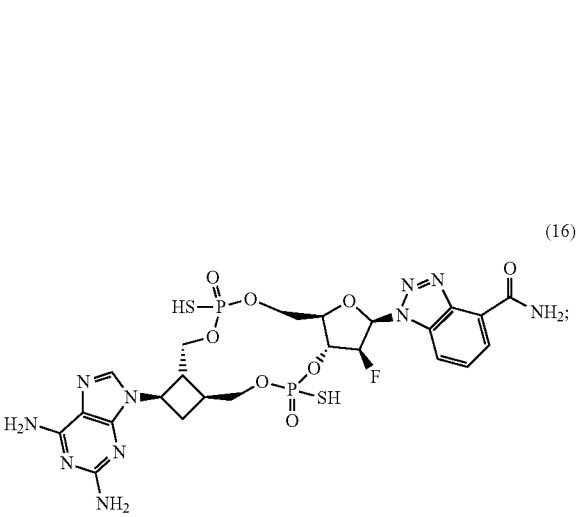
or a pharmaceutically acceptable salt, solvate, or hydrate thereof.
In some embodiments, the cyclic dinucleotide is a further modified. In some embodiments, the cyclic dinucleotide is an S-alkylated dinucleotide. In some embodiments, the cyclic dinucleotide is the compound selected from:

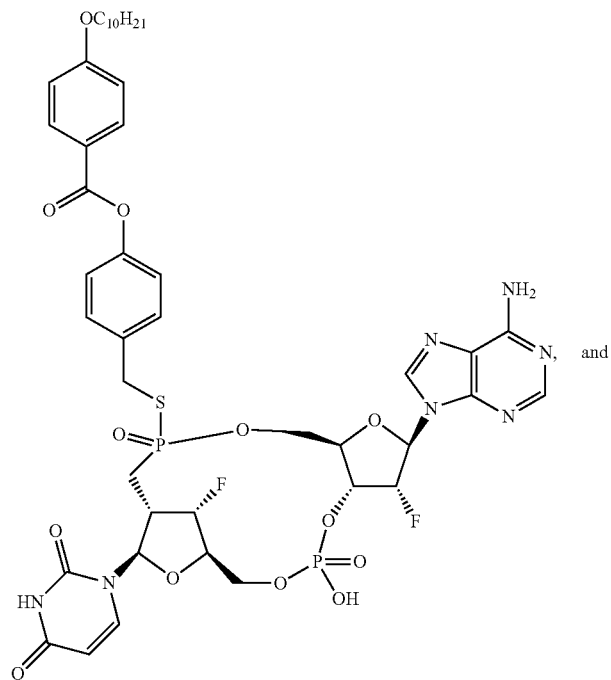
(17)
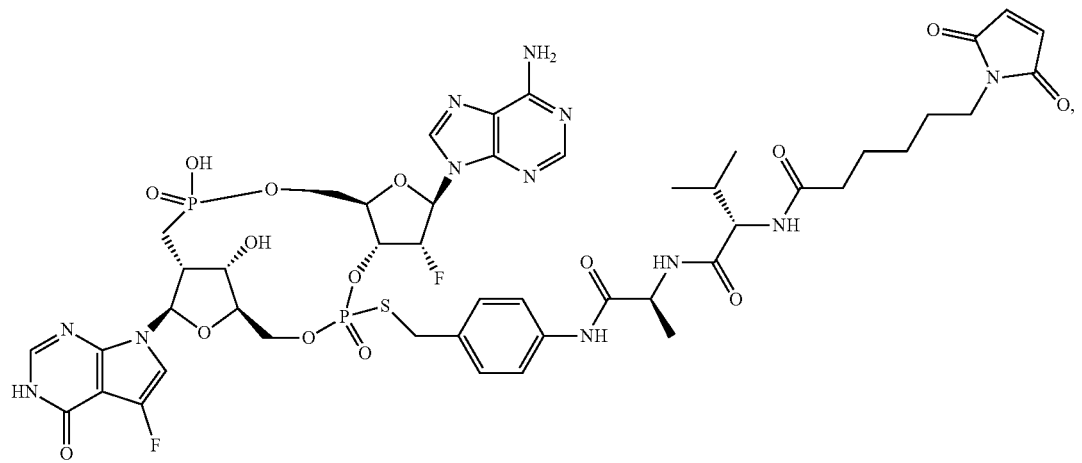
(18)
or a pharmaceutically acceptable salt thereof.

In some embodiments, the cyclic dinucleotide is a compound selected from:

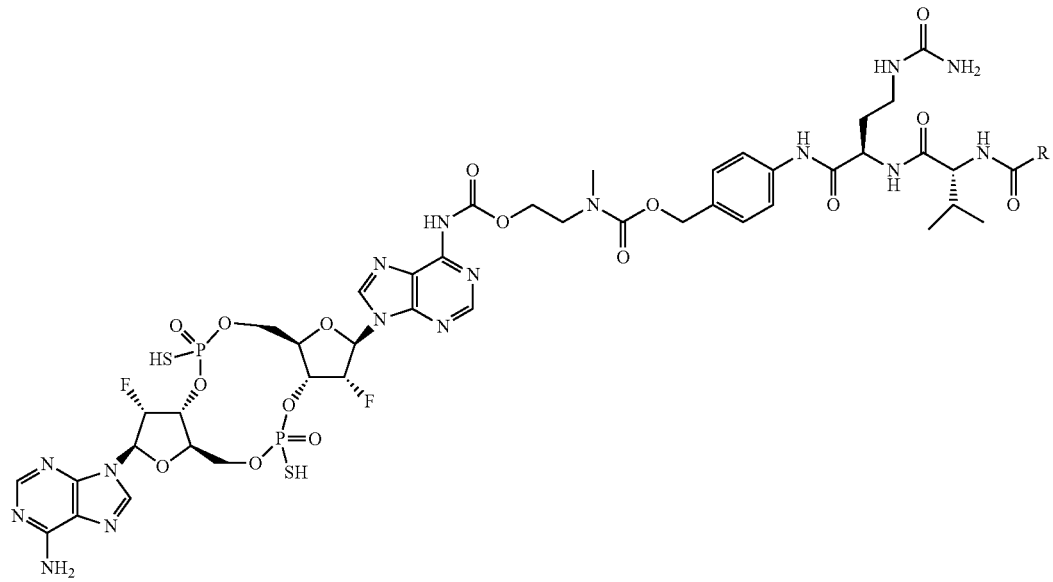

where R is 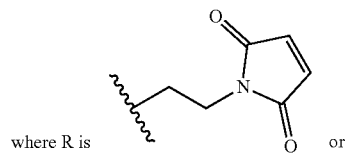 (19)

or 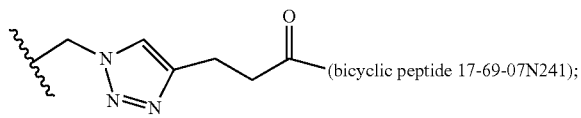 (20)

or a pharmaceutically acceptable salt, solvate, or hydrate thereof.

In some embodiments, the cyclic dinucleotide is modified with a T cell epitome KLFAVWKITYKDT derived from polio virus in combination with a glycopeptide antigen. In some embodiments, the cyclic dinucleotide is:

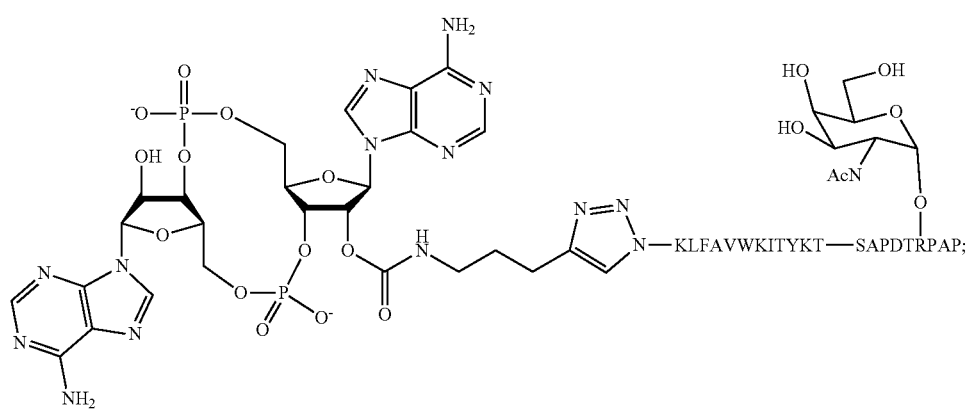 (21)

or a pharmaceutically acceptable salt, solvate, or hydrate thereof.

In some embodiments, the non-peptide STING agonist is not a cyclic dinucleotide. In some embodiments, the non-peptide STING agonist is a small molecule such as flavone acetic acid (FAA), 10-carboxymethyl-9-acridanone (CMA), or α-Mangostin. In some embodiments, the non-peptide STING agonist is a compound selected from:

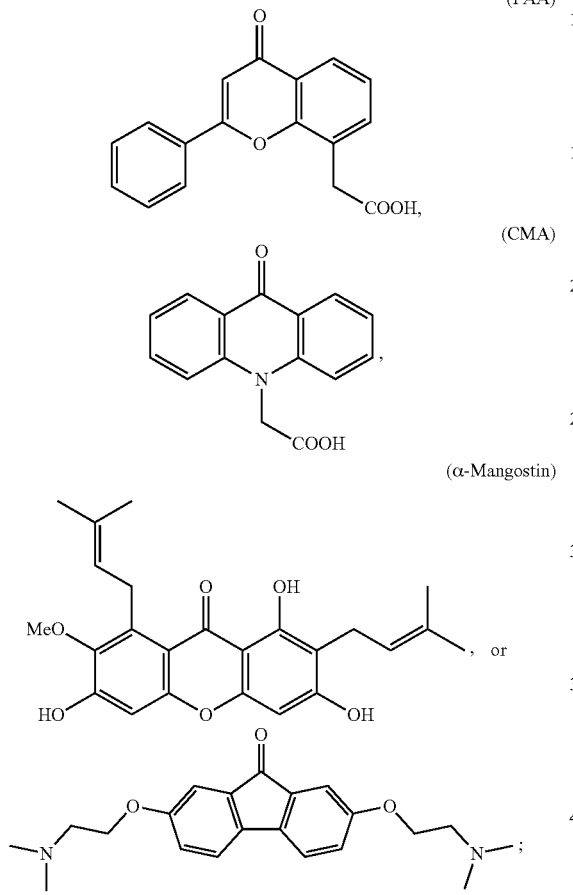

or a pharmaceutically acceptable salt, solvate, or hydrate thereof.

In some embodiments, the non-peptide STING agonist is a small molecule such as a benzothiophene. In some embodiments, the small molecule STING agonist is a compound selected from:

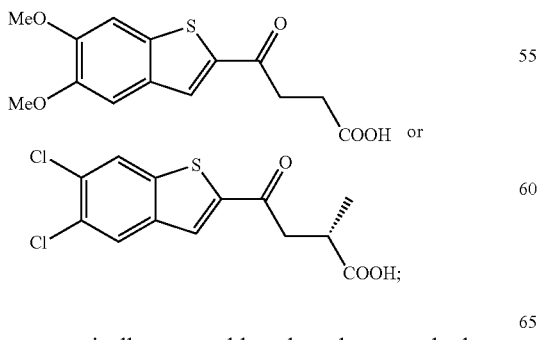

or a pharmaceutically acceptable salt, solvate, or hydrate thereof.

In some embodiments, the non-peptide STING agonist is a compound selected from:

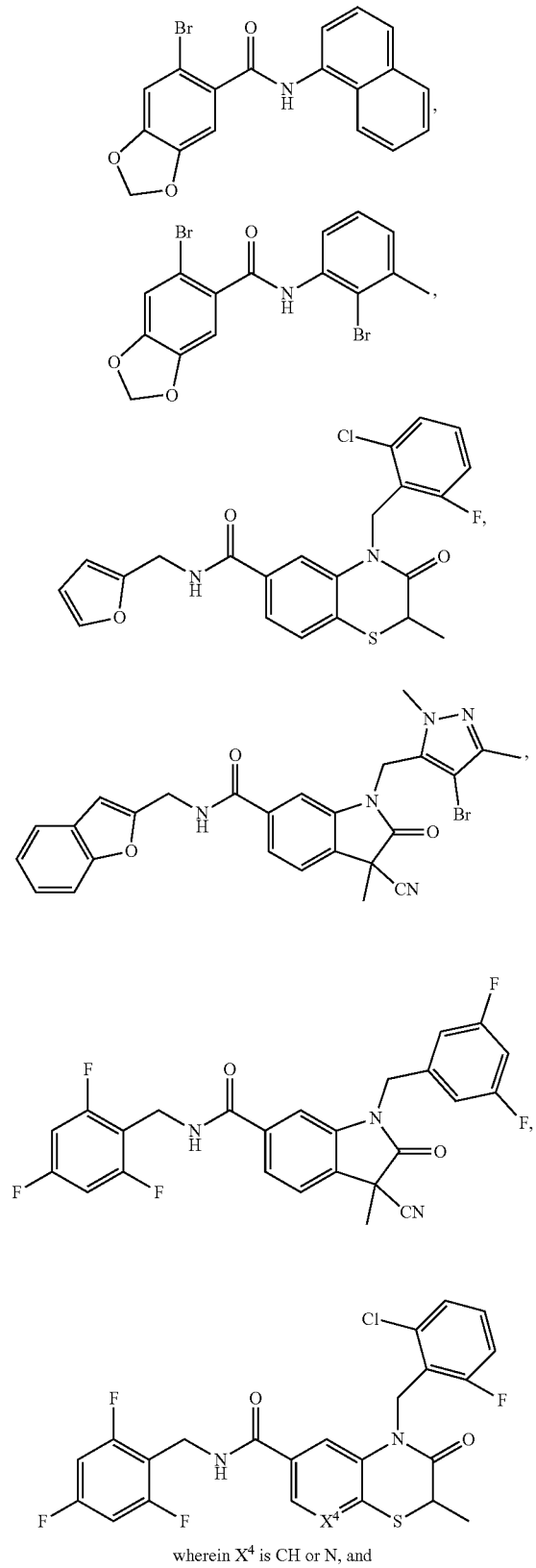

wherein $X^4$ is CH or N, and

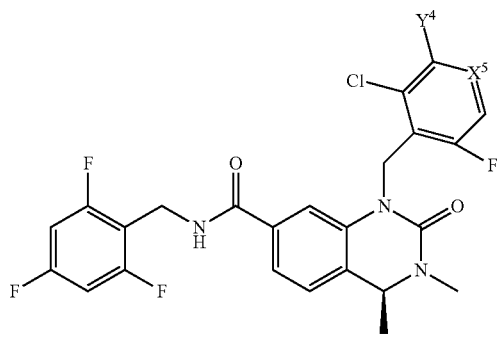

wherein $X^5$ is CH or N and $Y^4$ is $NH_2$ or $CH_3$; or a pharmaceutically acceptable salt, solvate, or hydrate thereof.

In some embodiments, the non-peptide STING agonist is:

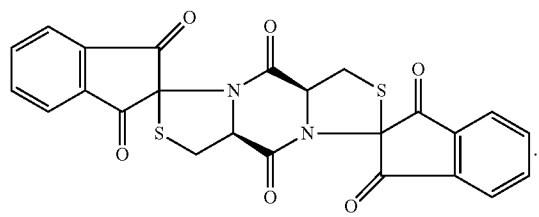 [SMILES: O=C1[C@H]2CSC3(C(=O)c4ccccc4C3=O)N2C(=O)[C@H]2CSC3(C(=O)c4ccccc4C3=O)N12]

In some embodiments, the non-peptide STING agonist is ADU-S100, or a pharmaceutically acceptable salt, solvate, or hydrate thereof. In some embodiments, ADU-100 has the structure:

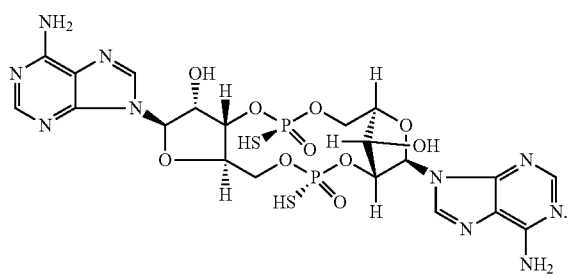 [SMILES: Nc1ncnc2c1ncn2[C@@H]1O[C@@H]2CO[P@@](=O)(S)O[C@@H]3C(O)[C@@H](CO[P@@](=O)(S)O[C@H]2[C@H]1O)O[C@H]3n1cnc2c(N)ncnc21]

In some embodiments, the non-peptide STING agonist is an amidobenzimidazole. In some embodiments, the non-peptide STING agonist has the structure of Formula (IV), or a pharmaceutically acceptable salt, solvate, or hydrate thereof:

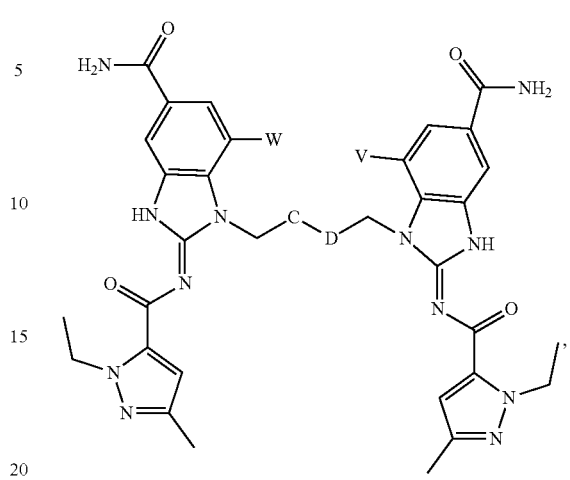

wherein:

C-D is an alkylene or alkenylene;

W is H or —$OCH_3$; and

V is H or —O—($C_1$-$C_3$)alkyl-($C_3$-$C_6$)heterocycle.

In some embodiments of Formula (IV), or a pharmaceutically acceptable salt, solvate, or hydrate thereof, C-D is a $C_2$-$C_8$ alkylene. In some embodiments, C-D is a $C_2$-$C_8$ alkenylene. In some embodiments, C-D is —$CH_2CH_2$— or —CH=CH—. In some embodiments, W is hydrogen. In some embodiments, W is —$OCH_3$. In some embodiments, V is hydrogen. In some embodiments, V is —O—$(CH_2)_3$—$C_6$ heterocycloalklyl.

In some embodiments, the non-peptide STING agonist is selected from:

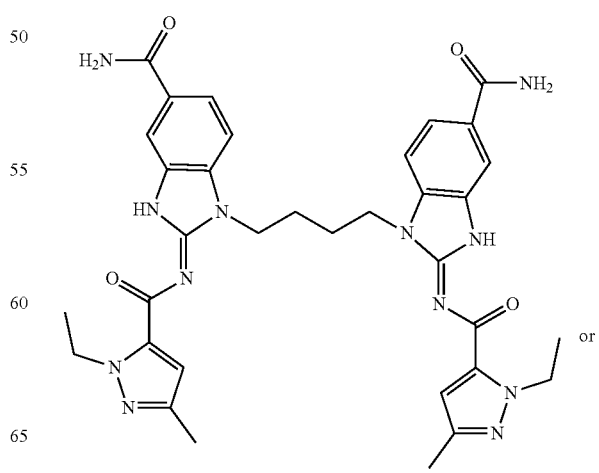

or

-continued

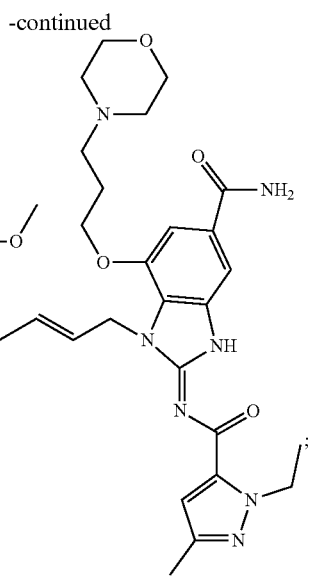

or a pharmaceutically acceptable salt, solvate, or hydrate thereof.

In some embodiments, the non-peptide STING agonist is:

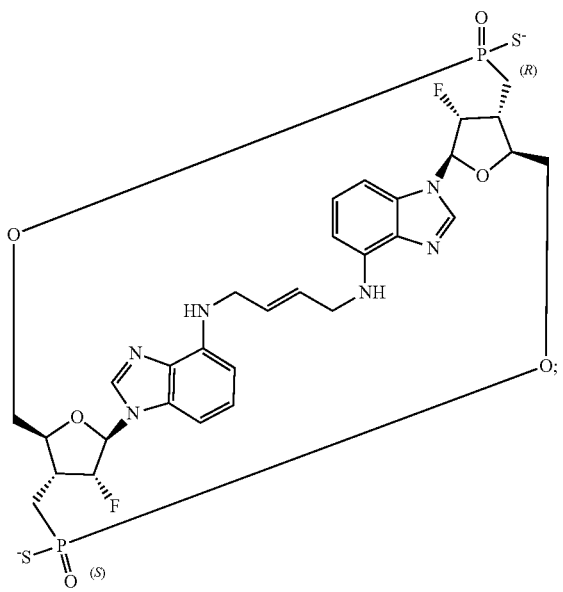

or a pharmaceutically acceptable salt, solvate, or hydrate thereof.

II. Micelles, Mixtures, and Compositions

In some embodiments, the non-peptide STING agonist is encapsulated within a micelle comprising the block copolymer. In some embodiments, the micelle comprises one or more different types of block copolymer components from various unimers. In some embodiments, the non-peptide STING agonist is non-covalently encapsulated by the micelle comprising the block copolymer.

In some embodiments, the pharmaceutical compositing comprises one or more micelles wherein each micelle comprises (i) a block copolymer of Formula (I) and (ii) a non-peptide STING agonist. In some embodiments, the one of more micelles comprise two, three, or more different non-peptide STING agonists. In some embodiments, the one or more micelles comprise two or three different non-peptide STING agonists. In some embodiments, the one of more micelles comprise the same non-peptide STING agonist.

The use of micelles in cancer therapy may enhance anti-tumor efficacy and reduce toxicity to healthy tissues, in part due to the size of the micelles. While small molecules such as certain chemotherapeutic agents can enter both normal and tumor tissues, non-targeted micelle nanoparticles may preferentially cross leaky tumor vasculature. The size of the micelles will typically be in the nanometer scale (i.e., between about 1 nm and 1 μm in diameter). In some embodiments, the micelle has a diameter of less than about 1 μm. In some embodiments, the micelle has a size of about 10 to about 200 nm. In some embodiments, the micelle has a size of about 20 to about 100 nm. In some embodiments, the micelle has a size of about 30 to about 50 nm.

In some embodiments, the non-peptide STING agonist is not encapsulated within the micelle. In some embodiments, the pharmaceutical composition comprises a mixture of components comprising (i) a block copolymer of Formula (I) and (ii) a non-peptide STING agonist. In some embodiments, the mixture comprises two, three, or more different non-peptide STING agonists. In some embodiments, the mixture comprises two or three different non-peptide STING agonists. In some embodiments, the mixture comprises one distinct type of non-peptide STING agonist. In some embodiments, the mixture comprises one or more different types of block copolymer components from various unimers.

In some embodiments, the pharmaceutical composition comprises a 10:1, 5:3, 5:2, 5:1, 4:1, 3:2, 3:1, 2:1; 1:1, or any combination therein, molar ratio of (i) a block copolymer of Formula (I) and (ii) a non-peptide STING agonist. In some embodiments, the pharmaceutical composition comprises a 2:1 or 1:1 molar ratio. In some embodiments, the non-peptide STING agonist is a small molecule. In some embodiments, the non-peptide STING agonist is a cyclic dinucleotide. In some embodiments, the non-peptide STING agonist is cGAMP.

In some embodiments, the pharmaceutical composition further comprises a saline or a saccharide solution. In some embodiments, the saccharide or saline solution is a buffer. In some embodiments, the saccharide solution is a glucose solution. In some embodiments, the saline solution is a sodium chloride solution.

pH Responsive Compositions

In some embodiments, the pharmaceutically composition is a pH responsive composition. The pH responsive compositions disclosed herein, comprise one or more pH-responsive micelles and/or nanoparticles that comprise block copolymers and a non-peptide STING agonist. Each block copolymer comprises a hydrophilic polymer segment and a hydrophobic polymer segment wherein the hydrophobic polymer segment comprises an ionizable amine group to render pH sensitivity. This pH sensitivity is exploited to provide compositions suitable as drug delivery therapeutics.

The micelles may have different pH transition values within physiological range, in order to target specific cells or microenvironments. In some embodiments, the micelle has a pH transition value of about 5 to about 8. In some embodiments, the micelle has a pH transition value of about 5 to about 6. In some embodiments, the micelle has a pH transition value of about 6 to about 7. In some embodiments, the micelle has a pH transition value of about 7 to about 8. In some embodiments, the micelle has a pH transition value of about 6.3 to about 6.9. In some embodiments, the micelle has a pH transition value of about 5.0 to about 6.2. In some embodiments, the micelle has a pH transition value of about 5.9 to about 6.2. In some embodiments, the micelle has a pH transition value of about 5.0 to about 5.5. In some embodiments, the pH transition point is 4.8, 4.9, 5.0, 5.1, 5.2, 5.3, 5.4, or 5.5.

The pH-sensitive micelle compositions of the invention may advantageously have a narrow pH transition range, in contrast to other pH sensitive compositions in which the pH response is very broad (i.e. 2 pH units). This pH transition is the transition point at which the micelle dissociates, releasing the payload or activating the photophore (i.e., an indocyanine green dye). In some embodiments, the micelles have a pH transition range of less than about 1 pH unit. In various embodiments, the micelles have a pH transition range of less than about 0.9, less than about 0.8, less than about 0.7, less than about 0.6, less than about 0.5, less than about 0.4, less than about 0.3, less than about 0.2, less than about 0.1 pH unit. In some embodiments, the micelles have a pH transition range of less than about 0.5 pH unit. In some embodiments, the micelles have a pH transition range of less than about 0.25 pH unit. The narrow pH transition range advantageously provides a sharper pH response that can result in complete release the therapeutic payload, such as the non-peptide STING agonist, with subtle changes of pH.

III. Methods of Use

Aerobic glycolysis, known as the Warburg effect, in which cancer cells preferentially uptake glucose and convert it into lactic acid or other acids, occurs in all solid cancers. Lactic acid or other acids preferentially accumulates in the extracellular space due to monocarboxylate transporters or other transporters. The resulting acidification of the extracellular space promotes remodeling of the extracellular matrix for further tumor invasion and metastasis.

Some embodiments provided herein describe compounds that form micelles at physiologic pH (7.35-7.45). In some embodiments, the compounds described herein are non-covalently conjugated to a therapeutic agent. In some embodiments, the micelle has a molecular weight of greater than $2 \times 10^7$ Daltons. In some embodiments, the micelle has a molecular weight of $\sim 2.7 \times 10^7$ Daltons. In some embodiments, the therapeutic agents are sequestered within the micelle core at physiologic pH (7.35-7.45) (e.g., during blood circulation). In some embodiments, when the micelle encounters an acidic environment (e.g., tumor tissues), the micelles dissociate into individual compounds with an average molecular weight of about $3.7 \times 10^4$ Daltons, allowing the release of the therapeutic agent. In some embodiments, the micelle dissociates at a pH below the pH transition point (e.g. the acidic state of tumor microenvironment).

In some embodiments, the therapeutic agent may be incorporated into the interior of the micelles. Specific pH conditions (e.g. acidic pH present in tumors and endocytic compartments) may lead to rapid protonation and dissociation of micelles into unimers, thereby releasing the therapeutic agent (e.g. a drug). In some embodiments, the micelle provides stable drug encapsulation at physiological pH (pH 7.4), but can quickly release the drug in acidic environments.

In some instances, the pH-sensitive micelle compositions described herein have a narrow pH transition range. In some embodiments, the micelles described herein have a pH transition range ($\Delta pH_{10-90\%}$) of less than 1 pH unit. In various embodiments, the micelles have a pH transition range of less than about 0.9, less than about 0.8, less than about 0.7, less than about 0.6, less than about 0.5, less than about 0.4, less than about 0.3, less than about 0.2, less than about 0.1 pH unit. In some embodiments, the micelles have a pH transition range of less than about 0.5 pH unit. In some embodiments, the pH transition range is less than 0.25 pH units. In some embodiments, the pH transition range is less than 0.15 pH units. A sharp transition point allows the micelles to dissociate with the acidic tumor microenvironment.

These micelles may be used as drug-delivery agents and STING agonists. Micelles comprising a drug may be used to treat cancers, or other diseases wherein the drug may be delivered to the appropriate location due to localized pH differences (e.g. a pH different from physiological pH (7.4). In some embodiments, the disorder treated is a cancer. In some embodiments, the cancer comprises a solid tumor. In some embodiments, the tumor is a secondary tumor from metastasis of a primary tumor(s). In some embodiments, the drug-delivery may be to a lymph node or to a peritoneal or pleural surface.

In some embodiments is a method of treating a cancer in a subject in need thereof, comprising administering to the subject a therapeutically effective amount of any of the compositions disclosed herein.

In some embodiments, the cancer is a carcinoma, sarcoma, lymphoma, leukemia, melanoma, mesothelioma, multiple myeloma, or seminoma.

In some embodiments, the cancer is of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the cancer is breast cancer, head and neck squamous cell carcinoma (HNSCC), lung cancer, ovarian cancer, prostate cancer, bladder cancer, urethral cancer, esophageal cancer, colorectal cancer, peritoneal metastasis, renal cancer, or brain, skin (including melanoma and sarcoma). In some embodiments, the cancer is breast cancer, head and neck squamous cell carcinoma (HNSCC), esophageal cancer, colorectal cancer, or renal cancer.

In some embodiments, the cancer is a solid tumor.

In some embodiments, the tumor is reduced by about 5%, about 10%, about 15%, about 25%, about 30%, about 40%, about 50%, about 60%, about 70%, about 80%, or about 90%. In some embodiments, the tumor is reduced by about 50%. In some embodiments, the tumor is reduced by about 60%. In some embodiments, the tumor is reduced by about 70%. In some embodiments, the tumor is reduced by about 75%. In some embodiments, the tumor is reduced by about 80%. In some embodiments, the tumor is reduced by about 85%. In some embodiments, the tumor is reduced by about 90%. In some embodiments, the tumor is reduced by about 95%. In some embodiments, the tumor is reduced by about 99%.

The stimulator of interferon genes (STING) has received extensive interest as a target for autoimmunity and cancer immunotherapy. Early phase clinical trials using small molecule agonists, however, show limited antitumor efficacy and have dose-limiting toxicity.

In another aspect is a method of activating the STING pathway in a patient comprising administering to the patient in need thereof a pharmaceutical composition described herein.

In some embodiments is a method of activating the STING pathway in a subject comprising administering to the subject a therapeutically effective amount of a pharmaceutical composition as described here.

In some embodiments, the subject is a mammal. In some embodiments, the subject is a human.

In some embodiments, the method comprises administering the composition once. In some embodiments, the method comprises administering the composition two or more times. In some embodiments, the method comprises administering the composition before cancer surgery.

IV. Combination Therapy

In another aspect, the pharmaceutical compositions disclosed herein are administered with one or more additional therapies. In some embodiments, the method further comprises a second anti-cancer therapy. In some embodiments, the second anti-cancer therapy is surgery, chemotherapeutic, radiation therapy, gene therapy, or second immunotherapy. In some embodiments, the second anti-cancer therapy is a second immunotherapy. In some embodiments, the second immunotherapy is a checkpoint therapy. In some embodiments, the second anti-cancer therapy is radiation therapy. In some embodiments, the second therapy is surgery.

V. Kits

The present disclosure also provides kits. Any of the components disclosed herein may be combined in a kit. In certain embodiments the kits comprise a composition of the preceding embodiments described herein.

The kits will generally include at least one vial, test tube, flask, bottle, syringe or other container, into which a component may be placed, and preferably, suitably aliquoted. Where there is more than one component in the kit, the kit also will generally contain a second, third or other additional containers into which the additional components may be separately placed. However, various combinations of components may be comprised in a container. In some embodiments, all of the micelle populations in a series are combined in a single container. In other embodiments, some or all of the micelle population in a series are provided in separate containers.

The kits of the present disclosure also will typically include packaging for containing the various containers in close confinement for commercial sale. Such packaging may include cardboard or injection or blow molded plastic packaging into which the desired containers are retained. A kit may also include instructions for employing the kit components. Instructions may include variations that can be implemented.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Oxo" refers to the =O substituent.

"Thioxo" refers to the =S substituent.

"Alkyl" refers to a straight or branched hydrocarbon chain radical, having from one to twenty carbon atoms, and which is attached to the rest of the molecule by a single bond. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$ alkyl, $C_1$-$C_9$ alkyl, $C_1$-$C_8$ alkyl, $C_1$-$C_7$ alkyl, C1-$C_6$ alkyl, $C_1$-$C_5$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (i-propyl), n-butyl, i-butyl, s-butyl, n-pentyl, 1,1-dimethylethyl (t-butyl), 3-methylhexyl, 2-methylhexyl, 1-ethyl-propyl, and the like. In some embodiments, the alkyl is methyl, ethyl, s-butyl, or 1-ethyl-propyl. Unless stated otherwise specifically in the specification, an alkyl group may be optionally substituted as described below. "Alkylene" or "alkylene chain" refers to a straight or branched divalent hydrocarbon chain linking the rest of the molecule to a radical group. In some embodiments, the alkylene is —$CH_2$—, —$CH_2CH_2$—, or —$CH_2CH_2CH_2$—. In some embodiments, the alkylene is —$CH_2$—. In some embodiments, the alkylene is —$CH_2CH_2$—. In some embodiments, the alkylene is —$CH_2CH_2CH_2$—.

"Alkoxy" refers to a radical of the formula —OR where R is an alkyl radical as defined. Unless stated otherwise specifically in the specification, an alkoxy group may be optionally substituted as described below. Representative alkoxy groups include, but are not limited to, methoxy, ethoxy, propoxy, butoxy, pentoxy. In some embodiments, the alkoxy is methoxy. In some embodiments, the alkoxy is ethoxy.

"Heteroalkylene" refers to an alkyl radical as described above where one or more carbon atoms of the alkyl is replaced with a O, N or S atom. "Heteroalkylene" or "heteroalkylene chain" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkyl groups include, but are not limited to —$OCH_2OMe$, —$OCH_2CH_2OMe$, or —$OCH_2CH_2OCH_2CH_2NH_2$. Representative heteroalkylene groups include, but are not limited to —$OCH_2CH_2O$—, —$OCH_2CH_2OCH_2CH_2O$—, or —$OCH_2CH_2OCH_2CH_2OCH_2CH_2O$—.

"Alkylamino" refers to a radical of the formula —NHR or —NRR where each R is, independently, an alkyl radical as defined above. Unless stated otherwise specifically in the specification, an alkylamino group may be optionally substituted as described below.

The term "aromatic" refers to a planar ring having a delocalized π-electron system containing 4n+2π electrons, where n is an integer. Aromatics can be optionally substituted. The term "aromatic" includes both aryl groups (e.g., phenyl, naphthalenyl) and heteroaryl groups (e.g., pyridinyl, quinolinyl).

"Aryl" refers to an aromatic ring wherein each of the atoms forming the ring is a carbon atom. Aryl groups can be optionally substituted. Examples of aryl groups include, but are not limited to phenyl, and naphthalenyl. In some embodiments, the aryl is phenyl. Depending on the structure, an aryl group can be a monoradical or a diradical (i.e., an arylene group). Unless stated otherwise specifically in the specification, the term "aryl" or the prefix "ar-" (such as in "aralkyl") is meant to include aryl radicals that are optionally substituted.

"Carboxy" refers to —CO$_2$H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to:

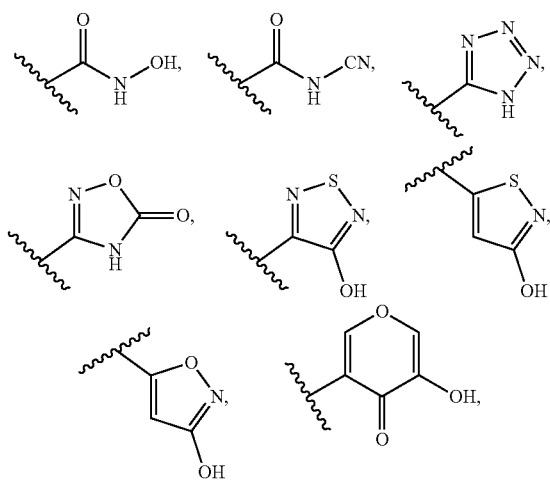

and the like.

"Cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. In some embodiments, a cycloalkyl is a C$_3$-C$_6$ cycloalkyl. In some embodiments, a cycloalkyl is a 3- to 6-membered cycloalkyl. Representative cycloalkyls include, but are not limited to, cycloalkyls having from three to ten carbon atoms, from three to eight carbon atoms, from three to six carbon atoms, or from three to five carbon atoms. Monocyclic cyclcoalkyl radicals include, for example, cyclopropyl, cyclobutyl, cyclopentyl, cyclohexyl, cycloheptyl, and cyclooctyl. In some embodiments, the monocyclic cyclcoalkyl is cyclopropyl, cyclobutyl, cyclopentyl or cyclohexyl. Polycyclic radicals include, for example, adamantyl, norbornyl, decalinyl, and 3,4-dihydronaphthalen-1(2H)-one. Unless otherwise stated specifically in the specification, a cycloalkyl group may be optionally substituted.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" refers to an alkoxy radical, as defined above, that is substituted by one or more halo radicals, as defined above, e.g., trifluoromethoxy, difluoromethoxy, fluoromethoxy, trichloromethoxy, 2,2,2-trifluoroethoxy, 1,2-difluoroethoxy, 3-bromo-2-fluoropropoxy, 1,2-dibromoethoxy, and the like. Unless stated otherwise specifically in the specification, a haloalkoxy group may be optionally substituted.

"Heterocycloalkyl" or "heterocyclyl" or "heterocyclic ring" refers to a stable 3- to 14-membered non-aromatic ring radical comprising 2 to 13 carbon atoms and from one to 6 heteroatoms selected from the group consisting of nitrogen, oxygen, and sulfur. In some embodiments, the heterocycloalkyl is a C$_2$-C$_7$ heterocycloalkyl. In some embodiments, the heterocycloalkyl is a C2-C6 heterocycloalkyl. In some embodiments, the heterocycloalkyl is a C2-C5 heterocycloalkyl. In some embodiments, the heterocycloalkyl is a 3- to 8-membered heterocycloalkyl. In some embodiments, the heterocycloalkyl is a 3- to 7-membered heterocycloalkyl. In some embodiments, the heterocycloalkyl is a 3- to 6-membered heterocycloalkyl. In some embodiments, the heterocycloalkyl is a 3- to 5-membered heterocycloalkyl. Unless stated otherwise specifically in the specification, the heterocycloalkyl radical may be a monocyclic, or bicyclic ring system, which may include fused (when fused with an aryl or a heteroaryl ring, the heterocycloalkyl is bonded through a non-aromatic ring atom) or bridged ring systems. The nitrogen, carbon or sulfur atoms in the heterocyclyl radical may be optionally oxidized. The nitrogen atom may be optionally quaternized. The heterocycloalkyl radical is partially or fully saturated. Examples of such heterocycloalkyl radicals include, but are not limited to, dioxolanyl, thienyl [1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. Unless otherwise noted, heterocycloalkyls have from 2 to 10 carbons in the ring. In some embodiments, heterocycloalkyls have from 2 to 8 carbons in the ring. In some embodiments, heterocycloalkyls have from 2 to 8 carbons in the ring and 1 or 2 N atoms. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

"Heteroaryl" refers to an aryl group that includes one or more ring heteroatoms selected from nitrogen, oxygen and sulfur. The heteroaryl is monocyclic or bicyclic. In some embodiments, the heteroaryl is a 5- or 6-membered heteroaryl. In some embodiments, the heteroaryl is a 5-membered heteroaryl. In some embodiments, the heteroaryl is a 6-membered heteroaryl. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, pyrazinyl, pyrimidinyl, thiazolyl, thienyl, thiadiazolyl or furyl. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring.

The term "optionally substituted" or "substituted" means that the referenced group may be substituted with one or more additional group(s) individually and independently selected from alkyl, haloalkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halogen, acyl, acyloxy, —CO$_2$H, —CO$_2$alkyl, nitro, and amino, including mono- and di-substituted amino groups (e.g., —NH$_2$, —NHR, —N(R)$_2$), and the protected derivatives thereof. In some embodiments, optional substituents are independently selected from alkyl, alkoxy, haloalkyl, cycloalkyl, halogen, —CN, —NH$_2$, —NH(CH$_3$), —N(CH$_3$)$_2$, —OH, —CO$_2$H, and —CO$_2$alkyl. In some embodiments, optional substituents are independently selected from fluoro, chloro, bromo, iodo, —CH$_3$, —CH$_2$CH$_3$, —CF$_3$, —OCH$_3$, and —OCF$_3$. In some embodiments, optional substituents are independently selected from fluoro, chloro, —CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (=O).

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

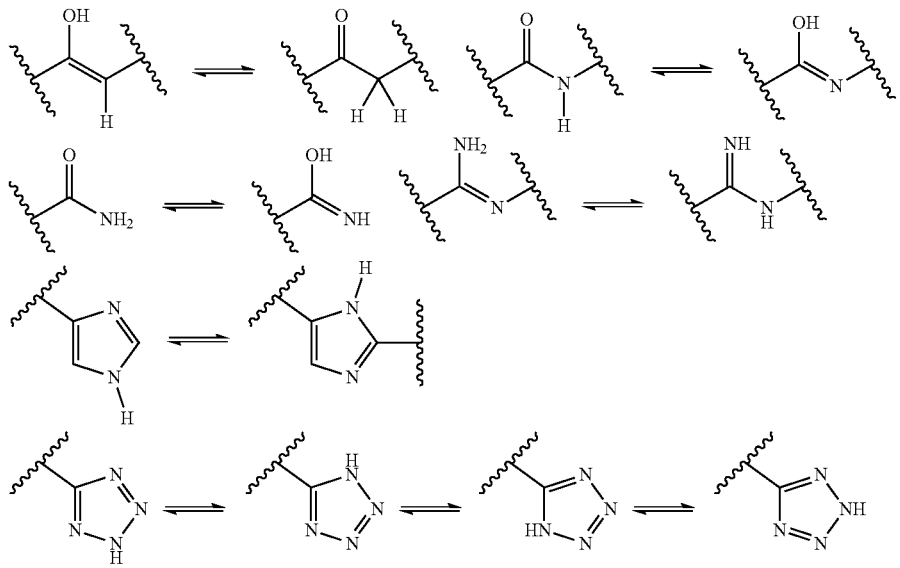

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

"Pharmaceutically acceptable," as used herein, refers a material, such as a carrier or diluent, which does not abrogate the biological activity or properties of the block copolymer, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zurich:Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts are obtained by reacting a block copolymer with an acid. In some embodiments, the block copolymer of Formula (I) (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a block copolymer of Formula (I) is prepared as a chloride salt, sulfate salt, bromide salt, mesylate salt, maleate salt, citrate salt or phosphate salt.

In some embodiments, pharmaceutically acceptable salts are obtained by reacting a block copolymer of Formula (I) with a base. In some embodiments, the block copolymer of Formula (I) is acidic and is reacted with a base. In such situations, an acidic proton of the block copolymer of Formula (I) is replaced by a metal ion, e.g., lithium, sodium, potassium, magnesium, calcium, or an aluminum ion. In some cases, block copolymers described herein coordinate with an organic base, such as, but not limited to, ethanolamine, diethanolamine, triethanolamine, tromethamine, meglumine, N-methylglucamine, dicyclohexylamine, tris (hydroxymethyl)methylamine. In other cases, block copolymers described herein form salts with amino acids such as, but not limited to, arginine, lysine, and the like. Acceptable inorganic bases used to form salts with block copolymers that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the block copolymers provided herein are prepared as a sodium salt, calcium salt, potassium salt, magnesium salt, melamine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), or pharmaceutically acceptable salts of block copolymers having the structure of Formula (I), as well as active metabolites of these compounds having the same type of activity.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine chlorine, iodine, phosphorus, such as, for example, $^{2}H$, $^{3}H$, $^{13}C$, $^{14}C$, $^{15}N$, $^{18}O$, $^{17}O$, $^{35}S$, $^{18}F$, $^{36}Cl$, $^{123}I$, $^{124}I$, $^{125}I$, $^{131}I$, $^{32}P$ and $^{33}P$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

As used herein, "pH responsive system," "pH responsive composition," "micelle," "pH-responsive micelle," "pH-sensitive micelle," "pH-activatable micelle" and "pH-activatable micellar (pHAM) nanoparticle" are used interchangeably herein to indicate a micelle comprising one or more compounds, which disassociates depending on the pH (e.g., above or below a certain pH). As a non-limiting example, at a certain pH, the block copolymers of Formula (I) is substantially in micellar form. As the pH changes (e.g., decreases), the micelles begin to disassociate, and as the pH further changes (e.g., further decreases), the block copolymers of Formula (I) is present substantially in disassociated (non-micellar) form.

As used herein, "pH transition range" indicates the pH range over which the micelles disassociate.

As used herein, "pH transition value" (pH) indicates the pH at which half of the micelles are disassociated.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular, intratumoral, or infusion), topical and rectal administration. Those of skill in the art are familiar with administration techniques that can be employed with the compounds and methods described herein. In some embodiments, the compounds and compositions described herein are administered orally. In some embodiments, the compositions described herein are administered intravenously.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the standard deviation of error for the device or method being employed to determine the value. Following longstanding patent law, the words "a" and "an," when used in conjunction with the word "comprising" in the claims or specification, denotes one or more, unless specifically noted.

EXAMPLES

Block copolymers and micelles described herein are synthesized using standard synthetic techniques or using methods known in the art.

Unless otherwise indicated, conventional methods of mass spectroscopy, NMR, HPLC, protein chemistry, biochemistry, recombinant DNA techniques and pharmacology are employed.

Block copolymers are prepared using standard organic chemistry techniques such as those described in, for example, March's Advanced Organic Chemistry, $6^{th}$ Edition, John Wiley and Sons, Inc.

Some abbreviations used herein are as follows:
DCM: dichloromethane
DMAP: 4-dimethylaminopyridine
DMF: dimethyl formamide
DMF-DMA: N,N-dimethylformamide dimethyl acetal
EDCI: 1-ethyl-3-(3-dimethylaminopropyl) carbodiimide
EtOAc: ethyl acetate
EtOH: ethanol
MeOH: methanol
PMDETA: N,N,N',N'',N''-Pentamethyldiethylenetriamine
CDI carbonyldiimidazole
TEA: triethyl amine
Hr Hour(s)
ISR Incurred sample reanalysis
IV Intravenous
kg Kilogram
mg Milligram(s)
mL Milliliters(s)
μg Microgram(s)
μm Mircons(s)
NC Not calculated
NR Not reported Suitable PEG polymers may be purchased (for example, from Sigma Aldrich) or may be synthesized according to methods known in the art. In some embodiments, the hydrophilic polymer can be used as an initiator for polymerization of the hydrophobic monomers to form a block copolymer. For example, 2-methacryloyloxyethyl phosphorylcholine (MPC) polymers (e.g. narrowly distributed MPC polymers) can be prepared by atom transfer radical polymerization (ATRP) with commercially available small molecule initiators such as ethyl 2-bromo-2-methylpropanoate (e.g. from Sigma Aldrich). These resulting MPC polymers can be used as macromolecular ATRP initiators to further copolymerize with other monomers to form block polymers can be synthesized using atom transfer radical polymerization (ATRP) or reversible addition-fragmentation chain transfer (RAFT) methods.

Example 1. Synthesis and Characterization

Syntheses of polymers. Monomers including 2-hexamethyleneiminoethyl methacrylate (C7A-MA), 2-(4-methylpiperidineleneimino)ethyl methacrylate (C6S1A-MA), 2-heptamethyleneiminoethyl methacrylate (C8A-MA), 2-diisopropylaminoethyl methacrylate (DPA-MA), and 2-ethylpropylaminoethyl methacrylate (EPA-MA) were synthesized. PEG-b-PR copolymers were synthesized using an atom transfer radical polymerization (ATRP) method. Poly(ethylene glycol)-b-poly(2-hexamethyleneiminoethyl methacrylate) with 70 repeating units, PC7A(70), is used as an example to illustrate the procedure. First, C7A-MA (1.5 g, 7 mmol), MeO-PEG$_{114}$-Br (0.5 g, 0.1 mmol, Sigma Aldrich), and PMDETA (21 µL, 0.1 mmol, Sigma Aldrich) were dissolved in a mixture of 2-propanol (2 mL) and dimethylformamide (2 mL) in a Schlenk flask. Oxygen was removed by three cycles of freeze-pump-thaw, then CuBr (14 mg, 0.1 mmol, Alfa Aesar) was added under nitrogen protection. Polymerization was carried out in vacuo at 40° C. overnight. After polymerization, the reaction mixture was diluted in tetrahydrofuran (10 mL), then passed through a neutral Al$_2$O$_3$ column to remove the catalyst. The organic solvent was removed by rotary evaporation. The residue was dialyzed in distilled water and lyophilized to obtain a white powder. After syntheses, the product was characterized by $^1$H NMR and gel permeation chromatography. The four other polymers, including PC6S1A, PC8A, PDPA, and PEPA, were all synthesized with 70 repeating units. PC7A polymers with different repeating units were synthesized by adjusting the initial ratio of C7A-MA monomer over the MeO-PEG$_{114}$-Br initiator.

Syntheses of dye-conjugated copolymers followed a similar procedure. Primary amino groups (aminoethyl methacrylate or AMA-MA, Polysciences) were introduced into each polymer chain by controlling the feeding ratio of AMA-MA monomer to the initiator (3:1). After synthesis, PEG-b-(PR-r-AMA) was dissolved in dimethylformamide, and dye-N-hydroxylsuccinimidal ester was added (3 molar equivalences to the primary amino group, Lumiprobe). After overnight reaction, the copolymer was purified by ultracentrifugation (MW=10 kD cutoff) three times to remove free dye molecules. The product was lyophilized and stored at −80° C.

Preparation of Micelle Nanoparticles. Micelle nanoparticles for cellular studies were prepared following a solvent evaporation method. Briefly, polymer (4 mg) was first dissolved in methanol (0.4 mL) and then added dropwise into distilled water (3.6 mL) under sonication. Methanol was removed by ultrafiltration (MW=100 kD cutoff) three times with fresh distilled water. Sterile PBS was added to adjust the concentration to 200 µM as a stock solution.

cGAMP-loaded nanoparticles were prepared by mixing 2'3'-cGAMP in PC7A polymer solution containing 5% D-glucose at pH 4, followed by adjusting to pH 7.4 using NaOH. After micelle formation, the nanoparticles were analyzed by dynamic light scattering to measure size and size distribution. The cGAMP loading efficiency (>90%) was quantified by HPLC.

Expression, purification and labeling of recombinant STING proteins. Human STING C-terminal domain (CTD, amino acid sequence between 139-379) plasmid containing His$_6$ tag encoded in pET-SUMO vector (provided by Dr. Z. J. Chen, UT Southwestern) was used as a template to generate E296A/D297A, D319A/D320A, and E336A/E337A/E339A/E340A mutants using a Q5 site directed mutagenesis kit (NEB). Overexpression of WT or mutant protein was induced in Escherichia coli. (E. coli) strain BL21/pLys with 0.8 mM isopropyl-β-D-thiogalactoside (IPTG) at 16° C. for 18 h. Bacterial cells were collected, suspended (50 mM Tris-Cl, 300 mM NaCl, 20 mM imidazole, pH 8.0), and disrupted by sonication on ice. Cellular debris was removed by centrifugation at 20,000 g at 4° C. for 1 h. The supernatant was loaded onto a Ni$^{2+}$-nitrilotriacetate affinity resin (Ni-NTA, QIAGEN). After 4 h incubation at 4° C., the resin was rinsed three times with washing buffer (50 mM Tris-Cl, 1 M NaCl, 20 mM imidazole, pH 8.0). The SUMO tag was then removed by digesting the proteins using ULP1 SUMO protease at 4° C. overnight. Proteins were eluted with elution buffer (20 mM Tris-Cl, 50 mM NaCl, 20 mM imidazole, pH 7.5). Subsequently, the eluted proteins were subjected to size-exclusion chromatography using a Superdex 200 column (GE Healthcare), and the fractions were collected, concentrated, and dialyzed against a buffer containing 25 mM HEPES and 150 mM NaCl (pH 7.5). For dye-conjugation, protein solution was mixed with Cy5-NHS in NaHCO$_3$ (pH 8.4) at 4° C. overnight. Free dye molecules were removed by using a desalting column (7K, Thermo Scientific). Dye-labeled proteins were collected, concentrated, and used in phase separation studies.

Isothermal titration calorimetry (ITC). A MicroCal VP-ITC was used to measure the binding affinity between protein and polymer. STING dimer concentration was held at 12.5 µM and PC7A(70) at 10 µM. The titrations were performed at 20° C. in a buffer containing 25 mM HEPES and 150 mM NaCl (pH 6.5). Twenty-nine injections were performed in 3 min spacing time. The titration traces were integrated by NITPIC, the curves were fitted by SEDFIT, and the figures were prepared using GUSSI software: (http://biophysics.swmed.edu/MBR/software.html).

Nile Red assay. Nile Red assay is used for studying protein-protein interaction and interruption in protein structure. Briefly, Nile Red (final concentration 5 µM, Thermo Scientific), STING dimer (2.1 µM), and PC7A (0, 0.6, 1.2, 3, 6, or 12 µM) were mixed for 4 h. Their max excitation wavelengths and fluorescence intensities were recorded on a fluorescence spectrophotometer (Hitachi F-7000 model).

Phase condensation assay. Wild type (WT) or mutant human STING CTD (Cy5-labeled) was mixed with PC7A polymers of varying repeating units in a 96-well glass plate (coated with mPEG-silane) at 25° C. After 4 h, the mixture was centrifuged at 13,000 g for 5 minutes, and the supernatant was transferred to another plate. Fluorescent intensity of the supernatant was measured by a plate reader (CLARIOstar). Data are representative of at least three independent measurements. The degree of condensation (D) was calculated by the following equation:

$$D_i = \frac{F_3 - F_i}{F_0}$$

where $F_i$ is the fluorescent intensity of the supernatant for a specific group i and $F_0$ is the Cy5-STING intensity at the same concentration without PC7A addition.

For phase reversibility assay, STING CTD (Cy5-labeled) and PC7A polymer were first mixed. After condensate formation, the mixture was diluted ten times in pH=6.5 HEPES buffer, and shaken on a plate shaker for 24 h. The fluorescent intensity of supernatant was measured, and reversibility (R) was calculated by following equation:

$$R_i = \frac{D_i - D_{Ri}}{D_i}$$

where $D_{Ri}$ was the new DPS value after 24 h recovery.

For microscopy examination, STING protein (Cy5-labeled) was mixed with PC7A polymer in a 4-well glass chamber (Thermo Scientific, coated with mPEG-silane) at 25° C., and images were acquired over a 140-s time course in 4-s intervals with a Zeiss 700 confocal laser scanning microscope. Size was calculated as the average of longest and shortest axis of each condensate Example 2. Animals and Cells All animals were maintained at the animal facilities under specific pathogen-free conditions and all animal procedures were performed with ethical compliance. Female C57BL/6 mice (6-8 weeks old) were obtained from the UT Southwestern breeding core.

STING-GFP MEFs, HEK293T (ATCC), B16F10 (ATCC), MC38 (ATCC), TC-1 were cultured in complete DMEM media supplemented with 10% fetal bovine serum (FBS). THP-1 cells (ATCC) were cultured in RPMI media supplemented with 10% FBS and 0.05 mM β-mercaptoethanol (O-ME). All cells were grown at 37° C. in 5% $CO_2$. THP-1 monocytes were differentiated into macrophages by phorbol 12-myristate 13-acetate (PMA, 150 nM, InvivoGen) before use.

In cell mutagenesis assay, GFP tagged full-length WT STING plasmid was used as a template to generate E296A/D297A, D319A/D320A, and E336A/E337A/E339A/E340A mutants. HEK293T cells were transfected with lipofectamine 2000 (Invitrogen) carrying full-length WT or mutant STING-GFP plasmid for 24 h and allowed to recover for 12 h before use. WT or R232H THP-1 reporter cells were purchased from Invitrogen. R238A/Y240A and single or dual Q273A/A277Q Hela mutants were used as cGAMP-resistant STING mutant cells.

Microscopy. Cells were grown in a 4-well glass chamber and treated with cGAMP or PC7A polymer for indicated time. In STING degradation assay, LysoTracker Red DND-99 (Thermo Scientific) was used to stain lysosomes in live cells. In STING trafficking assay, cells were fixed in 4% paraformaldehyde, then permeabilized and stained for ER (Calnexin, Abcam), ERGIC (p58, Sigma Aldrich), Golgi (GM130, BD Biosciences), or p-TBK1 (Ser 172, Cell Signaling) using an immunofluorescence kit (Cell Signaling). Samples were mounted in prolong gold antifade with Dapi stain (Thermo Scientific) and imaged using a Zeiss 700 confocal laser scanning microscope with a 63× oil objective. ImageJ was used to quantify co-localization by Pearson's correlation coefficient. Data are representative of at least twenty cells. In inhibitor assay, cells were pre-treated with Brefeldin A (BFA, 10 μM, Selleckchem) for 1 h before cGAMP/PC7A addition.

Fluorescence recovery after photobleaching (FRAP) experiments. FRAP method is a versatile tool for determining diffusion and exchange properties of biomacromolecules. Both in vitro and cellular FRAP experiments were performed on a Zeiss 700 confocal laser scanning microscope at 25° C. In a typical procedure, a 2 μm diameter spot in the condensation was photobleached with 100% laser power for 5 seconds using a 633 nm laser. Images were acquired over a 150-s time course with 4-s intervals. Fluorescent intensity of the region of interest (ROI) was corrected by an unbleached control region and then normalized to pre-bleached intensity of the ROI. At least five ROIs per sample were measured. The mean intensity of the bleached spot was fit to a single exponential model.

Western blot analysis. All solutions were purchased from Bio-Rad and antibodies against STING, p-STING (S366), p-TBK1 (Ser 172) and p-IRF3 (Ser 369) were obtained from Cell Signaling. Briefly, cells were lysed in SDS sample buffer (with protease and phosphatase inhibitor cocktail) and heated for denaturation. Supernatant was loaded onto a 4-15% Mini-PROTEAN gel (Bio-Rad), and run at 50 V for 20 min followed by 100 V for 60 min. Electro transfer was performed using 100 V for 60 min on ice. After transfer, the membrane was blocked either in 5% non-fat milk or BSA (phosphorylated protein) for 1 h at room temperature, and incubated with primary antibody overnight at 4° C. HRP-linked secondary antibody (Bio-Rad) was used for 1 h at room temperature before detection on X-ray film (GE Healthcare). Membrane was stripped in stripping buffer for 30 min and reused for R-actin (Sigma Aldrich) detection.

RT-qPCR. Total RNAs were extracted from cells or human tissues by using RNeasy mini kit (QIAGEN). RNA quantity and quality were confirmed using NanoDrop (DeNovix DS-11). Genomic DNA was removed and cDNA was synthesized using an iScript™ gDNA clear cDNA synthesis kit (Bio-Rad). Bio-Rad SoAdvanced™ universal SYBR green supermix and CFX connect real-time system were used for PCR analysis. Results were corrected by β-actin or GAPDH. DNA primers are listed as follows:

Mouse ifn-β: ATGAGTGGTGGTTGCAGGC (SEQ ID NO: 1), TGACCTTTCAAATGCAGTAGATTCA (SEQ ID NO: 2).

Mouse cxcl10: GGAGTGAAGCCACGCACAC (SEQ ID NO: 3), ATGGAGAGAGGCTCTCTGCTGT (SEQ ID NO: 4).

Mouse irf7: AGTCTAAACAGCGCCCGGTA (SEQ ID NO: 5), GGTCGGGTGTAGTTTGAGGA (SEQ ID NO: 6).

Mouse tnf-α: TGATGAGAGGGAGGCCATTTG (SEQ ID NO: 7), TCTCCTTTGGGGTGAGTCTGT (SEQ ID NO: 8).

Mouse β-actin: ACACCCGCCACCAGTTCGC (SEQ ID NO: 9), ATGGGGTACTTCAGGGTCAGGATA (SEQ ID NO: 10).

Human ifn-β: GTCTCCTCCAAATTGCTCTC (SEQ ID NO: 11), ACAGGAGCTTCTGACACTGA (SEQ ID NO: 12).

Human cxcl10: TGGCATTCAAGGAGTACCTC (SEQ ID NO: 13), TTGTAGCAATGATCTCAACACG (SEQ ID NO: 14).

Human β-actin: GGACTTCGAGCAAGAGATGG (SEQ ID NO: 15), AGGAAGGAAGGCTGGAAGAG (SEQ ID NO: 16).

Human gapdh: ATGACATCAAGAAGGTGGTG (SEQ ID NO: 17), CATACCAGGAAATGAGCTTG (SEQ ID NO: 18).

Example 3. Evaluation of STING Activation in Tumor-Bearing Mouse

Mice were subcutaneously inoculated with B16F10 melanoma cells ($1.0\times10^5$) or TC-1 cells ($1.0\times10^5$) into the right flank. Intratumoral injection of different agents (50 µL of 5% glucose, 50 µg PC7A polymer, 0.5 or 2.5 µg cGAMP, or a formulation with 2.5 µg cGAMP in 50 µg PC7A nanoparticles, n=6 for each group) was performed when tumor size reached $100\pm20$ mm$^3$. Mice were euthanized one-day post-injection, and tumors and draining lymph nodes were collected. Total RNAs were extracted by TRIzol (Invitrogen), and the expressions of interferon-stimulated genes (ifn-β, cxcl10, tnf-α, and irf7) were measured via RT-qPCR.

Tumor therapy experiments. Mice were subcutaneously inoculated with MC38 cells ($1.0\times10^6$) or TC-1 cells ($1.0\times10^5$) into the right flank. Tumor size was measured every other day via a digital caliper, and tumor volume was calculated as $0.5\times length\times width^2$. On reaching sizes of ~50 mm$^3$, tumors were injected with different STING agonists (50 µL of 5% glucose, 50 µg PC7A polymer, 2.5 µg cGAMP, or 2.5 µg cGAMP in 50 µg PC7A nanoparticles), and some groups were intraperitoneally injected with 200 µg checkpoint inhibitors (anti-mPD-1, BioXcell, BE0146) for comparison or synergy evaluation. Mice were injected 3× in MC38 model and 4× in TC-1 model with treatments spaced 4 d apart. Mice were euthanized at a tumor burden endpoint of 2,000 mm$^3$.

Evaluation of STING activation in resected human tissues. Patients were consented to the use of biospecimens for research as approved by the UT Southwestern Institutional Review Board. Freshly resected human tissues (squamous cell carcinoma from the base of tongue, cervical tumor tissues, and a sentinel lymph node) were rinsed and divided into several sections (1-5 mm$^3$) using a scalpel, followed by injection at multiple sites using 5% glucose control, free cGAMP (80 ng), PC7A polymer (50 µg), or cGAMP-loaded PC7A nanoparticles (80 ng cGAMP in 50 µg PC7A nanoparticles) in 5% glucose solution within 30 min of resection. Each section was cultured in 0.5 mL RPMI 1640 medium (supplemented with 10% heat-inactivated human serum, 1% insulin-transferrin-selenium, 1% glutamax, and 1% penicillin-streptomycin) in a 24-well plate for 24 h. RNA was isolated and RT-qPCR was performed as previously described. For CD45 selection, tumor tissues were first digested by 1 mg/mL collagenase IV and 0.2 mg/mL DNase I (Sigma Aldrich) for 45 minutes at 37° C., then passed through a 70 µm nylon cell strainer to obtain single cells. CD45$^+$ leukocytes and CD45$^-$ cell populations were collected via magnetic separation using CD45 TIL microbeads and MS columns (Miltenyi Biotec) according to the manufacturer's instructions before RT-qPCR analysis.

Example 4. Results of PC7A with STING

Figure 7:
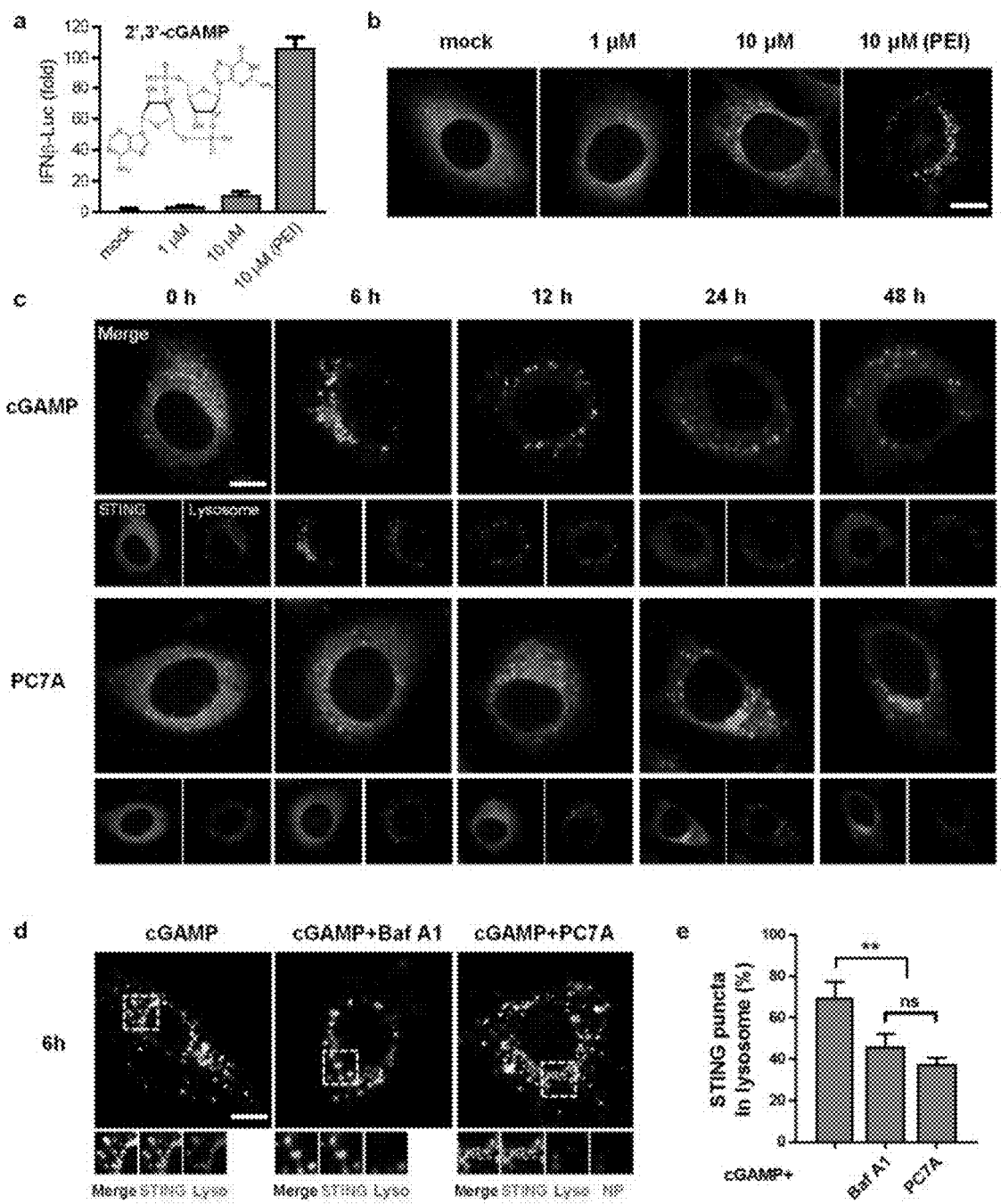
FIG. 7 shows that PC7A polymer induces durable immune activation and prevents rapid STING degradation compared to cGAMP. (a, b), Free cGAMP alone has limited STING activation in ISG-THP1 (a) and STING-GFP MEF cells (b) due to limited membrane permeability. A transfection agent, polyethyleneimine or PEI, was used to aid cytosolic delivery of cGAMP in the ensuing studies unless stated otherwise. c, STING proteins rapidly degrade within 12 h after cGAMP treatment, whereas PC7A prevents STING degradation over 48 h. Confocal microscopy images show varying degrees of colocalization of STING-GFP and lysosomes over time after cGAMP or PC7A treatment in MEFs. STING-GFP is shown in green and lysosomes were stained with LysoTracker DND-99 shown in red. Scale bar, 10 µm. (d, e) Treatment by PC7A or Bafilomycin A1 (Baf A1) reduced the fusion of cGAMP-induced STING puncta with lysosomes. Scale bar, 10 µm. Values are mean±SD, n=3. One-way ANOVA: ns, not significant; **, P<0.01.

PC7A polymer activates STING with a spatiotemporal profile distinct from cGAMP. To understand how PC7A-induced STING activation differs from cGAMP, the intracellular distribution of GFP-labeled STING and the downstream signals in live cells in response to treatment was investigated. The temporal profile of PC7A-induced STING puncta formation and maturation is distinct from those induced by cGAMP. When primed by cGAMP, STING puncta formation occurs rapidly, producing a strong immune response which peaks around 6 h after stimulation, followed by rapid degradation and subsequent immune silence (FIG. 1a-c). In contrast, PC7A generates a durable STING activation profile, with sustained expression of interferon-stimulated genes (ifn-0 and cxcl10) over 48 h. STING degradation is delayed after PC7A stimulation, as indicated by the limited fusion of STING puncta with lysosomes even at 48 h (FIG. 1d and FIG. 7c). A similar effect of delayed STING degradation was observed in cGAMP-treated cells pre-incubated with bafilomycin A1 (Baf A1), a vacuolar H$^+$ ATPase inhibitor which blocks lysosome acidification, and in cells treated with combined cGAMP and PC7A (FIG. 7d, e). Overall, these data suggest the endo-lysosomal pH buffering capability of PC7A may be responsible for slow STING degradation.

Figure 8:
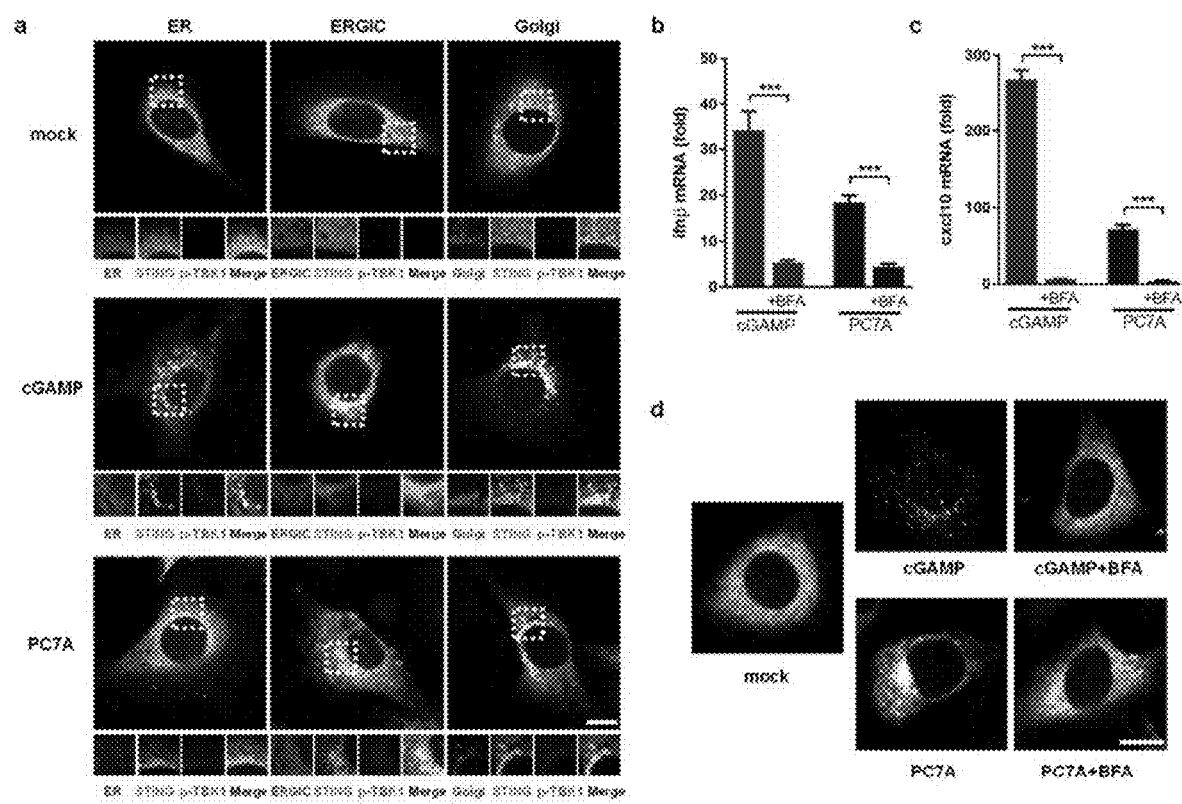
FIG. 8 shows that PC7A polymer activates STING through ER-ERGIC-Golgi translocation. a, STING-GFP is co-localized with ERGIC and Golgi following treatment by cGAMP or PC7A. STING-GFP MEF cells were first incubated with PEI-cGAMP (10 µM) or PC7A micelles (10 µM) for 1 h, followed by media exchange. Cells in cGAMP and PC7A treatment groups were fixed 6 h and 24 h later, respectively, prior to staining p-TBK1, ER (Calnexin), ERGIC (P58), Golgi (GM130), or nucleus. b-d, Brefeldin A (BFA) abolishes cGAMP or PC7A-induced STING activation in THP1 (b, c) and STING-GFP MEF (d) cells. In inhibited groups, cells were pre-treated with BFA (10 µM) before cGAMP or PC7A addition. Scale bars, 10 µm.

Despite the differences in size and kinetics of puncta formation, intracellular STING foci resulting from cGAMP or PC7A treatment follow a similar course of translocation from the endoplasmic reticulum (ER) to the ER-Golgi intermediate compartments (ERGIC) and the Golgi apparatus (FIG. 1e and FIG. 8a). During transportation, STING forms clusters and phosphorylates TANK-binding kinase 1 (TBK1) and interferon regulatory factor 3 (IRF3, FIG. 1f), which initiates the downstream production of type I IFNs. In the presence of brefeldin A (BFA), which blocks protein trafficking between ER and Golgi, both cGAMP and PC7A fail to trigger p-TBK1/p-IRF3 production and proinflammatory cytokine expression (FIG. 1f and FIG. 8b-d)

Figure 2:
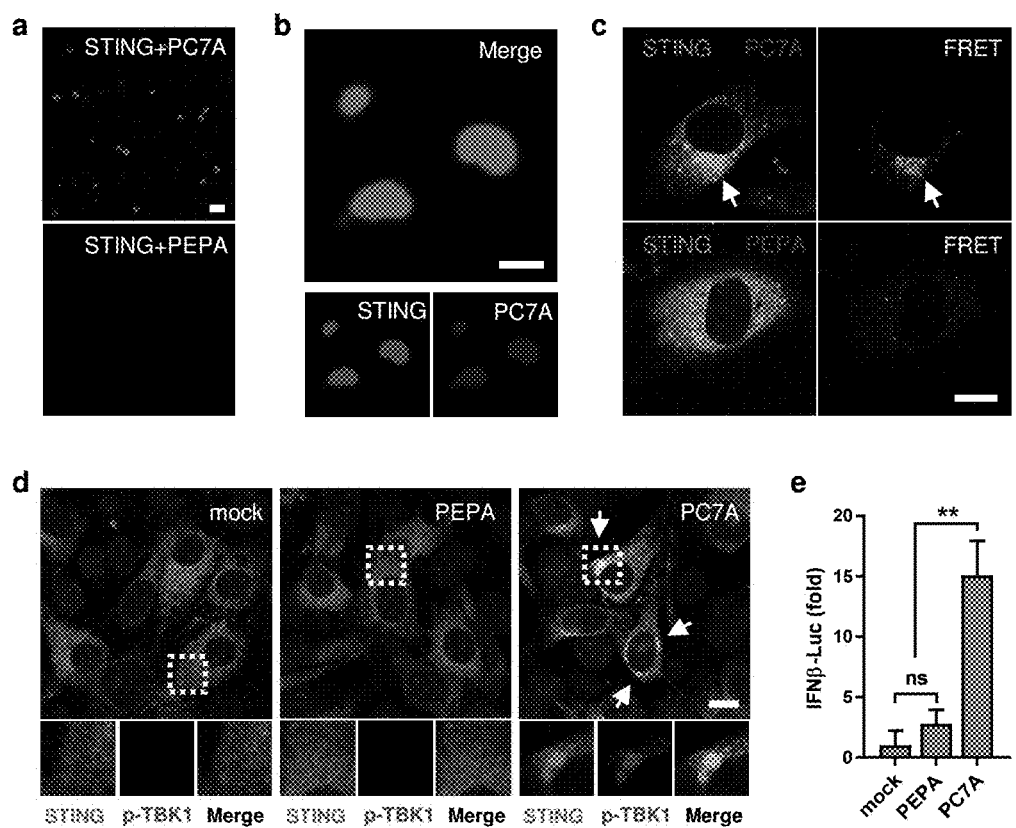
FIG. 2 shows that PC7A polymer induces STING condensation and immune activation. a, PC7A, but not PEPA, induces STING (Cy5-labeled) phase condensation after 4 h incubation. Scale bar, 10 µm. b, STING (4 µM, Cy5-labeled) and PC7A polymer (2 µM, AMCA-labeled) are colocalized within the condensates. Scale bar, 5 µm. c, Hetero-FRET from GFP-STING to TMR-PC7A illustrates colocalization of STING and PC7A in MEF cells. Energy transfer was not observed from GFP-STING to TMR-PEPA. Cell culture conditions identical to FIG. 1. GFP ($\lambda_{ex}/\lambda_{em}$=488/515 nm) and TMR (555/580 nm) signals are shown in the left panels as green and red, respectively. FRET signals (488/580 nm) are shown as yellow in the right panels. d, p-TBK1 is recruited in the STING/PC7A condensates. Scale bar, 10 µm. e, PC7A, not PEPA, induces expression of IFNβ-luciferase in ISG-THP1 cells. Values are mean±SD, n=3. One-way ANOVA: ns, not significant; **, P<0.01.
Figure 9:
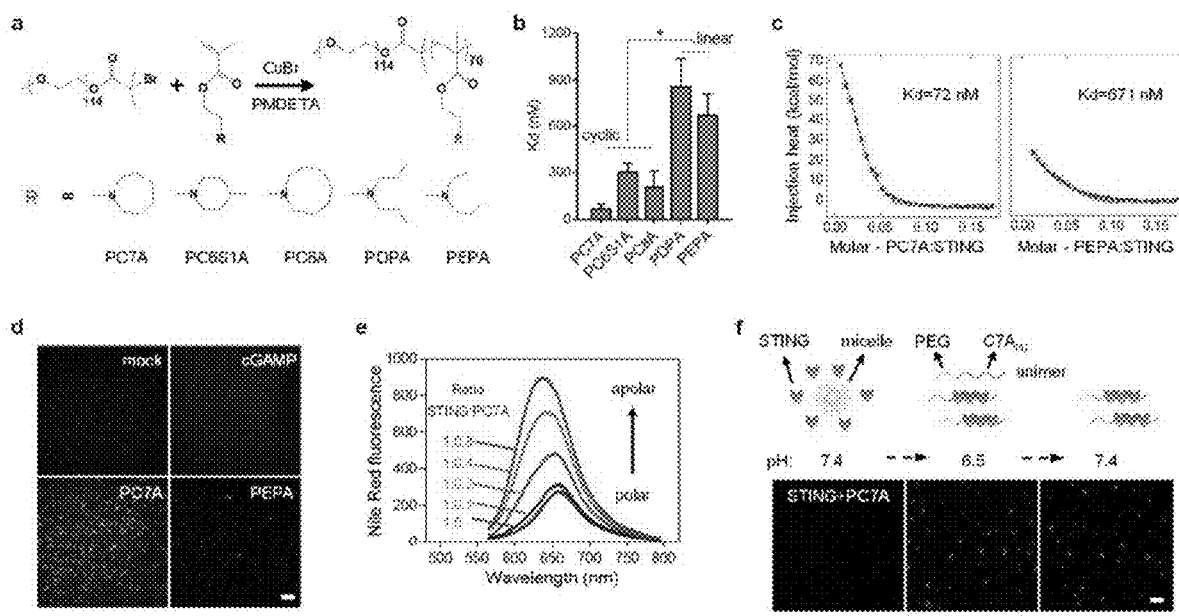
FIG. 9 displays that PC7A polymer shows STING-specific binding affinity, phase condensation, and immune activation compared to PEPA and other polymers. a, Schematic syntheses of block copolymers with different side chain structures using an atom-transfer radical polymerization (ATRP) method. b, ITC shows apparent binding affinity between STING and different polymers. Five polymers were divided into two groups based on their cyclic or linear side chains. Student's t-test: *, P<0.05. c, PC7A and PEPA, two polymers of the same backbone structure and identical pH transition (6.9), have different binding affinities to STING as measured by ITC. d, PC7A, not PEPA or cGAMP, induces STING phase separation from cell lysates. STING-GFP MEF cell lysate was treated with cGAMP, PC7A, or PEPA for 4 h. Scale bar, 20 µm. e, Fluorescence spectra of Nile Red in STING solutions with increasing concentrations of PC7A suggests the formation hydrophobic biomolecular condensates. f, PC7A tertiary amine blocks are shielded in the hydrophobic core of micelles under neutral pH (7.4), preventing their interactions with STING and phase condensation. Micelles dissociate into cationic unimers at pH 6.5 and induce STING phase separation. The newly formed PC7A-STING condensates are not pH reversible as indicated by the presence of condensates when the pH is titrated back to 7.4. Scale bar, 20 µm.

PC7A binds to STING and forms biomolecular condensates. To investigate the biophysical mechanism of PC7A-mediated STING clustering and activation, the binding affinity between PC7A and STING (human AA137-379, C-terminal domain) was determined by isothermal calorimetry (ITC). STING binds strongly to PC7A (apparent $K_d$=72 nM), but weakly to other polymers with the same backbone, such as PEPA (apparent $K_d$=671 nM, FIG. 9a-c). Notably, polymers with cyclic side chains exhibit higher affinity to STING than linear analogs, and the seven-membered-ring of PC7A elicits the strongest binding. To investigate whether PC7A was sufficient to induce clustering of STING in vitro, cyanine-5 (Cy5)-labeled STING CTD dimer was incubated with PC7A or PEPA at pH 6.5 (both P7CA and PEPA have apparent pKa's at 6.9, and stay as cationic unimers at pH 6.5). PEPA was used as a negative control due to its poor binding affinity to STING. Upon mixing of Cy5-STING and PC7A, liquid droplets were observed within minutes and grew over time, with approximately 85% of STING proteins present in condensates after 4 h (FIG. 2a, b). Incubation of Cy5-STING with PC7A labeled with aminomethylcoumarin acetate (AMCA) confirms co-localization of PC7A with STING puncta (FIG. 2b). Similar condensates were also observed in GFP-STING-expressing cell lysates after PC7A incubation (FIG. 9d). The biomolecular condensates are hydrophobic as indicated by the increased fluorescence intensity and red-shifted maximum emission wavelength in a Nile-Red assay (FIG. 9e). Fluorescence resonance energy transfer (FRET) from GFP-STING to tetramethylrhodamine (TMR)-PC7A further confirms the formation of a biomolecular condensate consisting of PC7A and STING in human-STING-overexpressing mouse embryonic fibroblasts (MEFs) (FIG. 2c). The downstream protein product, p-TBK1, was also found in this macromolecular cluster (FIG. 2d). In contrast, no obvious STING condensation or activation was observed when PEPA was used in these studies (FIG. 2 and FIG. 9d). At pH 7.4, few PC7A-STING condensates were formed (FIG. 9f) due to micellization of PC7A polymers above its pKa (6.9) and PEG shielding. Following endocytosis, PC7A micelles dissociate into cationic unimers during endosomal maturation, allowing for endosomal escape and cytosolic STING condensation and activation. Once PC7A unimers are bound into condensates with STING, the polymer is no longer available to form micelles and does not demonstrate a pH dependence of punctate formation (FIG. 9*i*).

Figure 3:
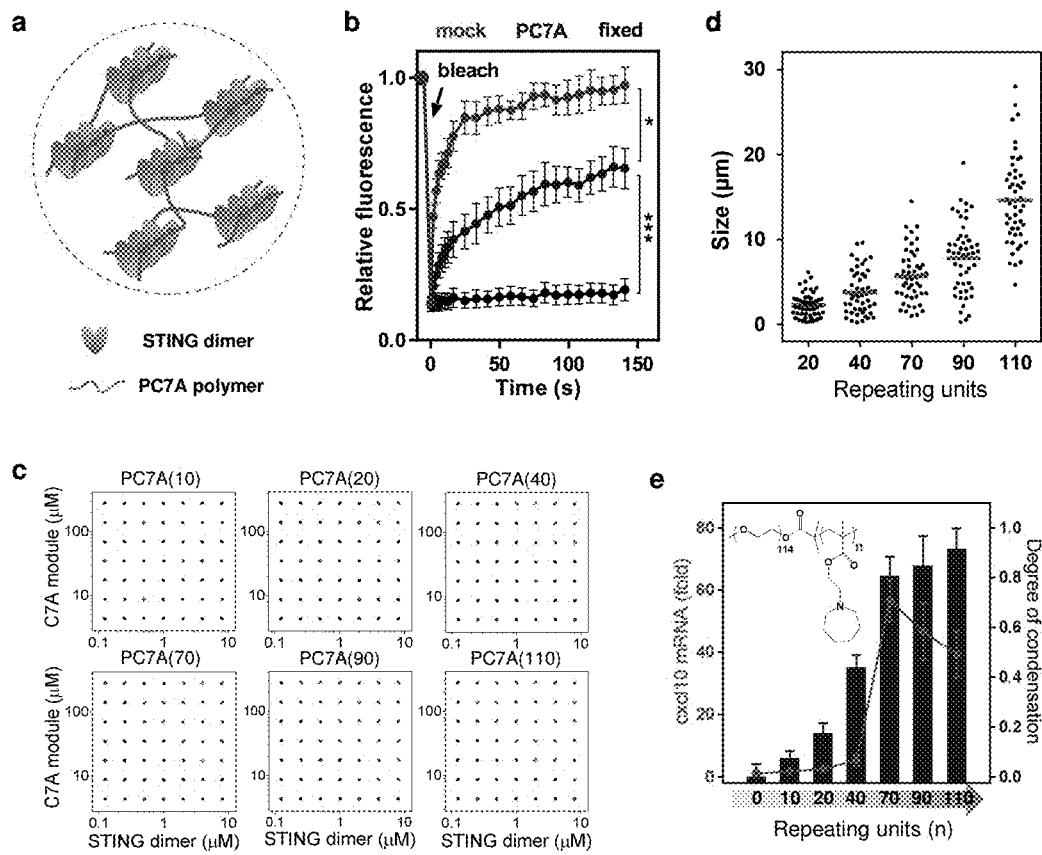
FIG. 3 shows that PC7A polymer induces STING condensation and immune activation through polyvalent interactions. a, Schematic of STING oligomerization and condensation driven by PC7A through polyvalent interactions. b, PC7A decreases the molecular mobility of GFP-STING in the condensates compared to free GFP-STING in MEF cells. Bleaching was performed 24 h after PC7A treatment, and recovery was monitored over 150 s. Untreated (mock) and fixed cells were used as mobile and stationary STING controls, respectively. Values are mean±SD, n=5. One-way ANOVA: *, P<0.05; ***, P<0.001. c, Biomolecular condensation of STING and PC7A is dependent on PC7A valency. Red dots indicate phase separation while blue dots indicate no phase separation. d, Size distributions of STING condensates induced by PC7A increase with higher PC7A valency. Condensate size was calculated as the average of longest and shortest axis, n=50. e, STING activation in THP1 cells correlates with the PC7A valency, with optimal cxcl10 expression induced by PC7A(70). Values are mean±SD, n=3. In experiments c through e, polymers with different repeating units were used at the same C7A modular concentrations.
Figure 10:
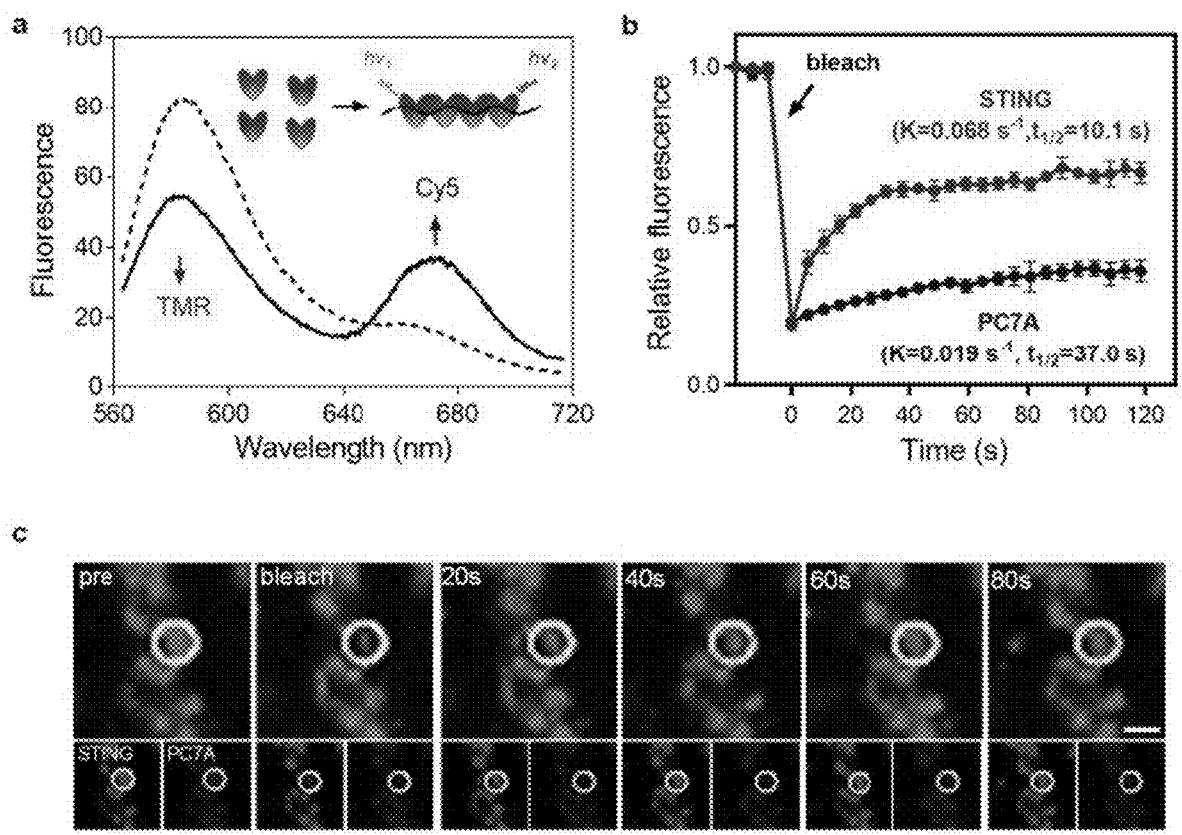
FIG. 10 shows that PC7A polymer induces STING oligomerization and condensation in which the two species express different recovery kinetics. a, Fluorescent spectra show hetero-FRET between STING dimers labeled by a FRET pair, TMR and Cy5 (mixed in a 1:1 ratio) after PC7A treatment (solid line). The decrease of TMR signal and increase of Cy5 signal after PC7A addition indicate STING oligomerization. b, c, STING protein or PC7A polymer in condensates exhibits different exchange kinetics by fluorescence recovery after photobleaching (FRAP) measurement. STING (4 µM, Cy5-labeled) and PC7A polymer (2 µM, AMCA-labeled) were incubated for 4 h. After photobleaching, recovery was observed over 120 s. Values are mean±SD, n=5. Fluorescence intensities of regions of interest were fit to the single exponential model: It=I0+(I$_\infty$−I0)× (1−e$^{-kt}$). Scale bar, 2 µm.

PC7A induces STING activation through polyvalent interactions. STING oligomerization upon cGAMP binding is responsible for the recruitment and activation of downstream TBK1 and IRF3 proteins. PC7A polymer may be able to serve as a supramolecular scaffold and directly engage polyvalent interactions to multimerize STING molecules for activation (FIG. 3*a*). To test this idea, STING proteins were labeled using a FRET pair (TMR and Cy5) and mixed the two differentially labeled proteins in a 1:1 ratio. Upon addition of PC7A, a strong energy transfer from TMR to Cy5 was observed (FIG. 10*a*), indicating close proximity of STING dimers after polyvalent binding to PC7A. Fluorescence recovery after photobleaching (FRAP) experiments on STING-PC7A condensates revealed that while both PC7A polymer and STING protein are exchangeable with surrounding molecules, PC7A exhibited a slower recovery rate than STING (FIG. 3*b* and FIG. 10*b, c*).

Figure 11:
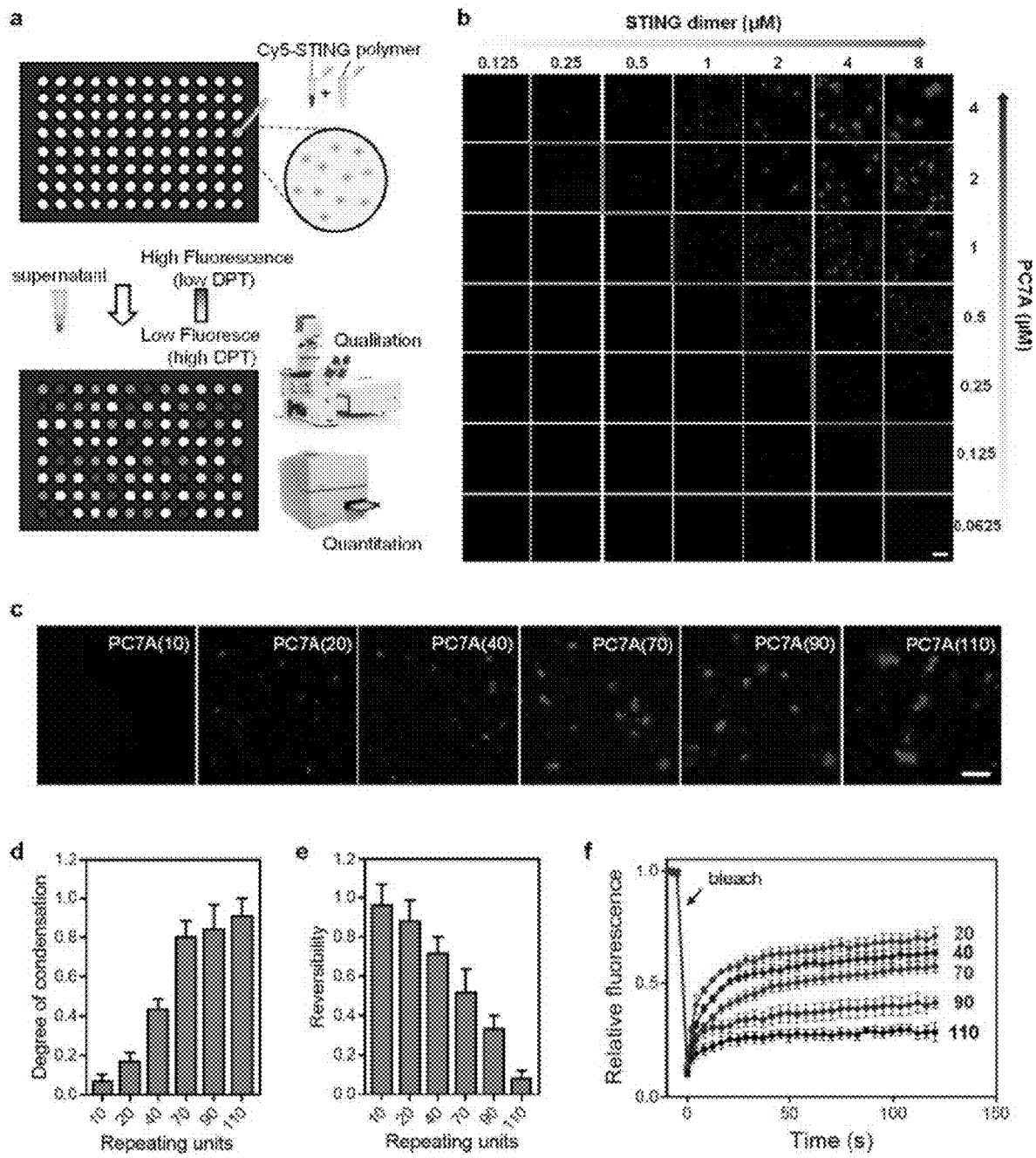
FIG. 11 shows that longer PC7A chain length induces larger condensate formation and slower recovery of STING. a, Schematic shows the qualitative and quantitative methods used to test the degree of condensation. b, Fluorescent images of condensates induced by indicated concentrations of PC7A and STING were used to generate phase diagrams. PC7A(70) is used as an example. Scale bar, 20 µm. c, PC7A of higher repeating units induce the formation of larger PC7A-STING condensates. Scale bar, 20 µm. d, Degree and e, reversibility of STING-PC7A condensates are inversely related. Values are mean±SD, n=3. f, STING recovery rate decreases with increasing PC7A length determined by FRAP method. Values are mean±SD, n=5. In all experiments, STING (4 µM, Cy5-labeled) and PC7A polymer (140 µM C7A modular concentration unless otherwise noted) were incubated for 4 h prior to analysis.

To examine the effects of binding valence, a series of PC7A polymers with an increasing number of repeating units. PC7A(n) refers to a polymer with n repeating units of C7A methacrylate monomer were synthesized. PC7A of increasing lengths was then incubated with STING dimer under a matrix of concentrations in vitro to generate a phase diagram, which shows a minimum requirement of 20 repeating units for condensation (FIG. 3*c*). No phase separation was observed for PC7A(10). Higher degree of PC7A polymerization resulted in larger condensates (FIG. 3*d* and FIG. 11*a-c*). For PC7A(110), over 90% of STING proteins were found in the condensates, compared to 17% when PC7A(20) was used (FIG. 11*d*). PC7A with higher degree of polymerization exhibited lower phase reversibility and slower recovery rate of STING after photobleaching (FIG. 11*e, f*). To investigate the relationship between condensate formation and STING activation in live cells, treated THP1 cells were treated with PC7A of varying lengths, and compared mRNA expression levels of cxcl10. Longer polymers induced higher cxcl10 expression, with peak levels observed at 70 repeating units of PC7A (FIG. 3*e*). Further elongation of chain length (e.g., 110) led to reduced cxcl10 expression, probably because of the weaker signaling capacity of oversized condensates with excessive crosslinking and poor molecular dynamics.

Figure 12:
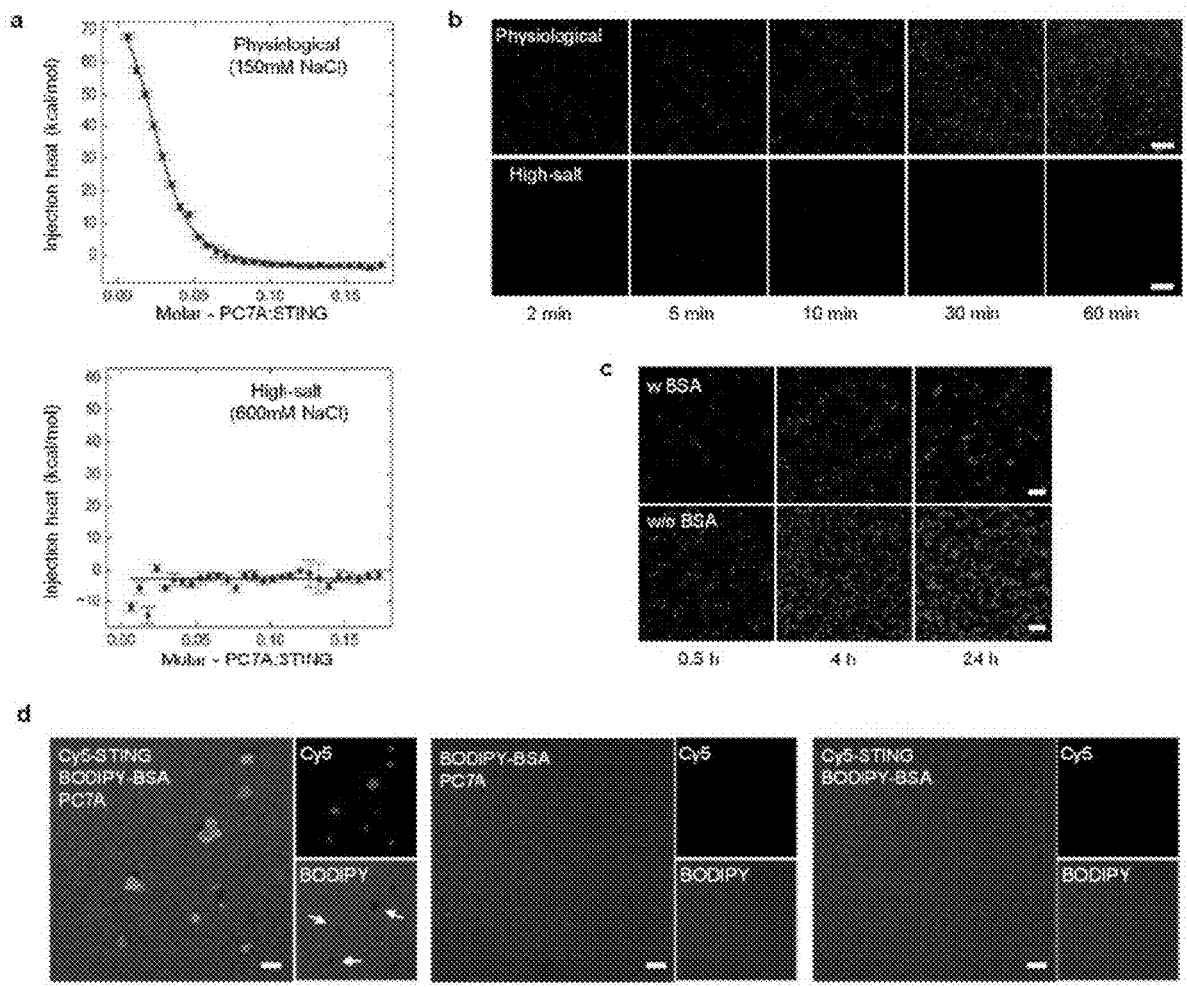
FIG. 12 shows that high salt and non-specific protein concentrations hinder STING-PC7A condensation. a, b, High salt concentration (e.g., 600 mM NaCl) abolishes binding and condensation of PC7A-STING. Scale bar, 20 µm. c, PC7A-STING condensates decrease in number and size in the presence of bovine serum albumin (BSA). Scale bar, 20 µm. d, BSA (labelled by BODIPY) is excluded from PC7A-STING condensates (lack of green fluorescence in the puncta). STING, BSA, and PC7A polymer were mixed for 4 h before observation under a confocal microscope. Controls without STING or PC7A were used to confirm STING-PC7A specificity in condensate formation. Scale bar, 10 µm. Experiments in b-d were performed with STING dimer (4 µM, Cy5-labeled) and PC7A (2 µM). BSA or BODIPY-labeled BSA (8 µM) were used.

PC7A binds to a distinct surface site from the cGAMP-binding pocket. The STING-PC7A condensates are sensitive to high concentrations of salt or the presence of other proteins. While STING-PC7A condensates were successfully formed at a physiological concentration of NaCl (150 mM), no phase separation was observed when salt concentration was raised to 600 mM (FIG. 12*a, b*). When bovine serum albumin (BSA) was added in the mixture of STING and PC7A, the condensates decreased in number and size (FIG. 12*c*). To further investigate the specificity of PC7A induced condensate, STING was labeled with Cy5 and BSA with boron-dipyrromethene (BODIPY) dyes. In the presence of PC7A, only Cy5-STING was present in the condensates, whereas the majority of BODIPY-BSA was excluded (FIG. 12*d*). As controls, mixtures of BSA/PC7A or STING/BSA did not form condensates.

Figure 4:
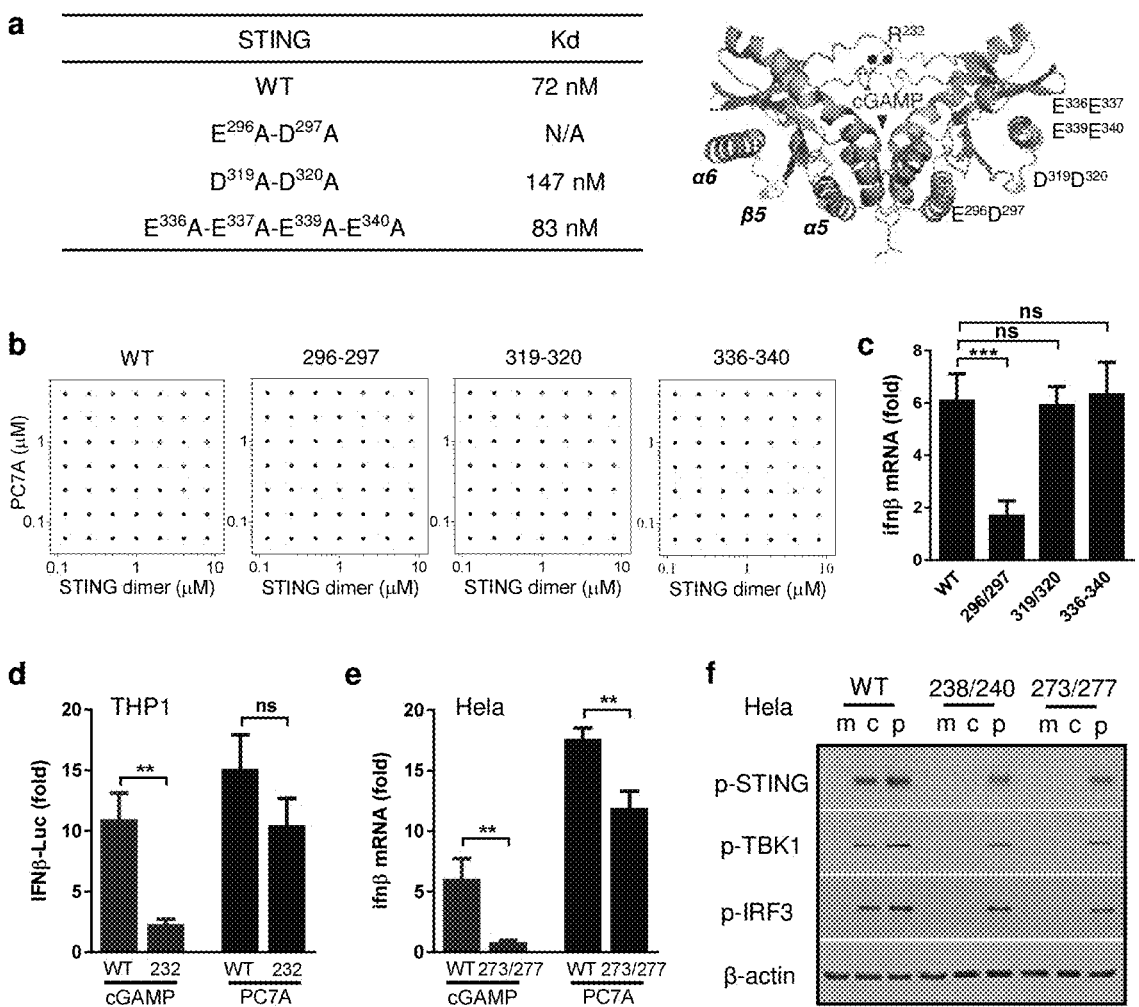
FIG. 4 shows that STING condensation and activation by PC7A polymer occurs through a distinct binding site from cGAMP. a-c, Mutation of E296A/D297A in STING abolishes PC7A affinity (a), condensation (b), and immune activation (c) in response to PC7A. Other mutations of STING do not affect PC7A-induced STING activation. Mutation sites are indicated on the STING structure and are distinct from the cGAMP binding site. Values are mean±SD, n=3. One-way ANOVA: ns, not significant; *, P<0.001. (d-f), PC7A retains immune activity in several cGAMP-resistant STING variants. R232H in THP1 cells or R238A/Y240A in Hela cells abrogate cGAMP binding. Q273A/A277Q, which disrupts the tetramer interface and cGAMP mediated STING oligomerization, abolishes STING activation by cGAMP but not by PC7A. Values are mean±SD, n=3. Two-tailed Student's t-test: ns, not significant; , P<0.01. m: mock; c: cGAMP; p: PC7A polymer.
Figure 13:
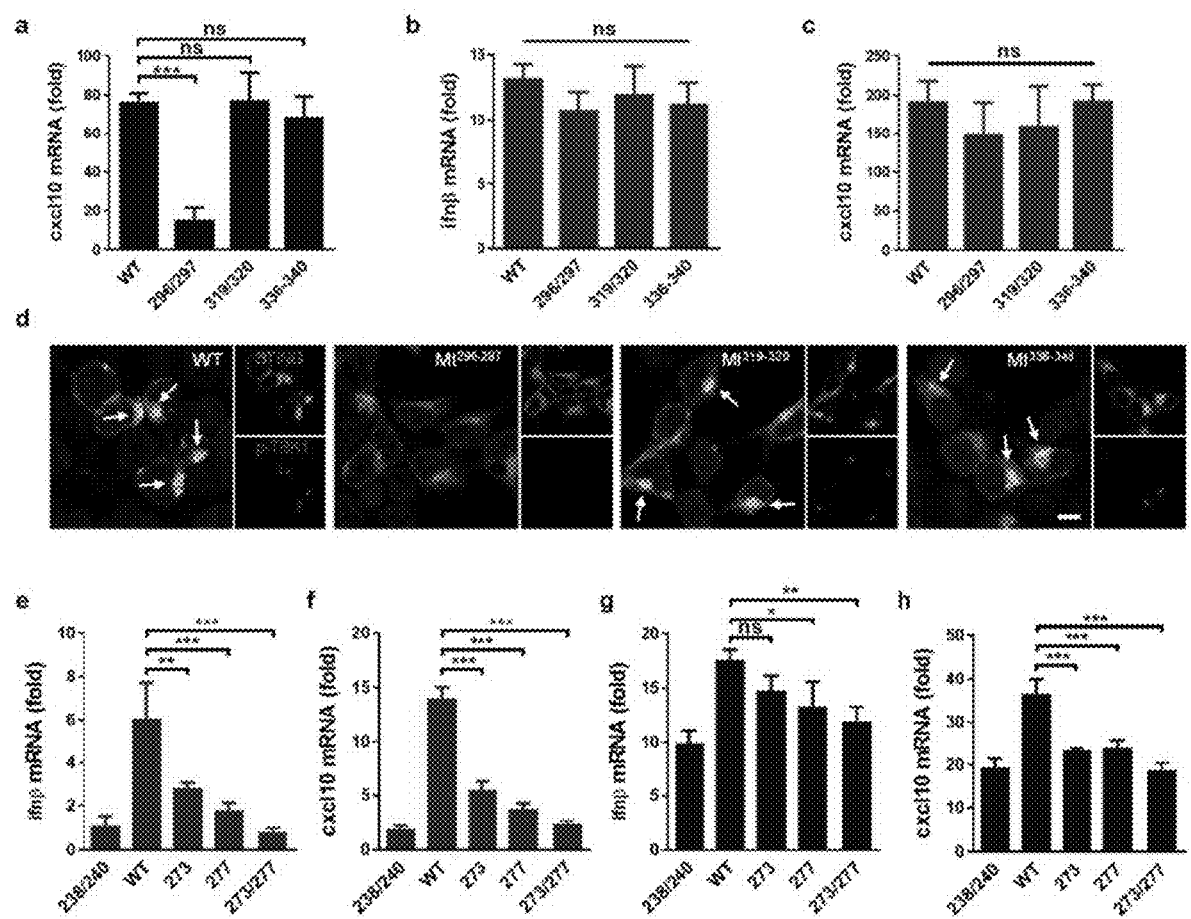
FIG. 13 shows that PC7A polymer activates STING through a different binding site from cGAMP. a-c, Mutation of E296D297 to neutral Ala residues abolishes ifn-β/cxc110 mRNA expression by PC7A polymer (a), but has no effect on cGAMP-stimulated STING response (b, c). Values are mean±SD, n=3. One-way ANOVA: ns, not significant; ***, P<0.001. d, Mutation of E296D297 abolishes intracellular p-TBK1 production after PC7A treatment. Scale bar, 10 μm. In a-d, HEK293T cells were transfected with WT or mutant STING-GFP plasmids for 24 h before use. e-h, STING mutant Hela cells (R238A/Y240A, Q273A/A277Q) abolish cGAMP-mediated STING activation (e, f), whereas they had less effects on PC7A-mediated response (g, h). R238A/Y240A is resistant to cGAMP binding, while single or dual Q273A/A277Q mutation disrupts the tetramer interface of cGAMP-induced STING oligomerization. Values are mean±SD, n=3. One-way ANOVA: ns, not significant; *, P<0.05; , P<0.01; *, P<0.001.

Based on the pH (FIG. 9*f*) and salt effects (FIG. 12*a, b*) on the PC7A-STING interactions and computational modeling, it appears that negatively charged surface sites on STING may be responsible for PC7A binding. To test this, STING mutants were constructed with several negatively charged amino acids in the α5-β5-α6 region replaced by alanine and investigated their PC7A binding affinity, phase condensation, and STING activation both in vitro and in live cells. Strikingly, mutation of two acidic residues (E296A/D297A) on the α5 helix was sufficient to abolish polymer binding and biomolecular condensation, whereas two other mutants (D319A/D320A and E336A/E337A/E339A/E340A) exhibited marginal effects (FIG. 4*a, b*). HEK293T cells were then transfected with mutant STING plasmids and measured downstream activation. Consistent with the abrogation of PC7A binding and condensation, the E296A/D297A mutant was deficient in forming condensate structures and inducing TBK1 phosphorylation and ifn-β/cxcl10 expression in cells (FIG. 4*c* and FIG. 13*a, d*). In contrast, these STING mutants did not impact cGAMP-mediated STING activation (FIG. 13*b, c*). Together, these data suggest that the $E^{296}D^{297}$ site on the α5 helix of STING, which is distinct from the cGAMP binding site, is responsible for PC7A binding and induced activation.

Endogenous STING agonists (cGAMP or other CDNs) bind to the STING dimer interface covered by a lip of four-stranded antiparallel R sheet (human AA 219-249). A natural STING variant (R232H) occurring in ~14% of the human population exhibits a reduced response to small molecule STING agonists. Since PC7A binds to a STING site different from the cGAMP binding pocket, the biological activity of PC7A was tested in THP1 cells harboring the STING R232H variant. Whereas the cGAMP response was expectedly abrogated in these cells, PC7A was still able to elevate IFN-β-Luc expression (FIG. 4*d*). Additional studies in mutant Hela cells (R238A/Y240A or Q273A/A277Q mutations that abolish cGAMP binding or prevent STING oligomerization upon cGAMP binding, respectively) show persistent PC7A-induced STING activation, whereas cGAMP-mediated effects were abolished (FIG. 4*e, f* and FIG. 13*e-h*). Collectively, these results demonstrate PC7A stimulates STING through cGAMP-independent mechanisms.

Figure 14:
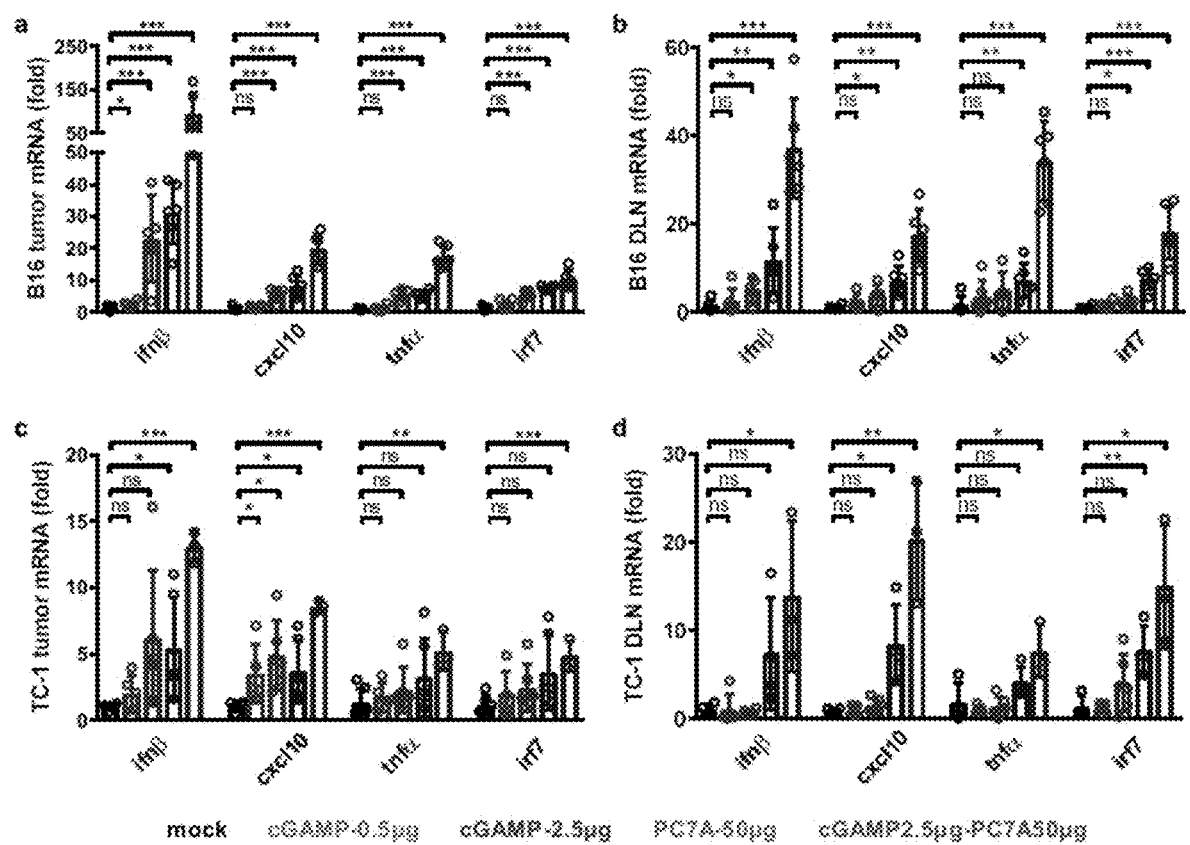
FIG. 14 shows that PC7A nanoparticle triggers STING activation in both tumor tissues and draining lymph node (DLN), and further synergizes with cGAMP in cytokine expression. Ifn, cxcl10, tnfα and irf7 gene expressions in tumor (a, c), or DLN (b, d) in B16 melanoma (a, b) or TC-1 tumor (c, d) mouse model after the indicated treatments. Values are mean±SD, n=6. One-way ANOVA: ns, not significant; *, P<0.05; , P<0.01; *, P<0.001.

PC7A boosts antitumor immune response in vivo and synergizes with cGAMP. The antitumor immunity of PC7A polymer was evaluated in subcutaneous tumors (100±20 mm³). C57BL/6 mice bearing the B16-F10 melanoma tumor model were treated with a single, intratumoral injection of PC7A nanoparticle (50 μg) or free cGAMP (low dose: 0.5 μg; high dose: 2.5 μg), and measured the expression of interferon-stimulated genes after 24 hours (ifn-β, cxcl10, tnf-α, and irf7, FIG. 14*a*). As expected, free cGAMP failed to induce interferon-stimulated gene expressions when administered at the low dose, while PC7A elevated the expressions by 5-30 folds. Furthermore, upon injection of cGAMP-loaded PC7A NP, the expression of ifn-β increased nearly 100-fold, indicating a synergistic effect in STING activation. This effect is likely mediated through cell intrinsic and noncanonical mechanisms as well as cytosolic delivery of cGAMP by PC7A NP. Importantly, PC7A NP and cGAMP-loaded PC7A NP generated a robust immune stimulation not only in the tumor but also in draining lymph nodes (FIG. 14*b*). In comparison, despite local STING activation within the tumor following an intratumoral injection of high dose cGAMP, minimal STING activation was detected in draining lymph nodes. A similar STING-activation effect was observed in a human papilloma virus (HPV) E6/7 TC-1 tumor model (FIG. 14*c, d*).

Figure 5:
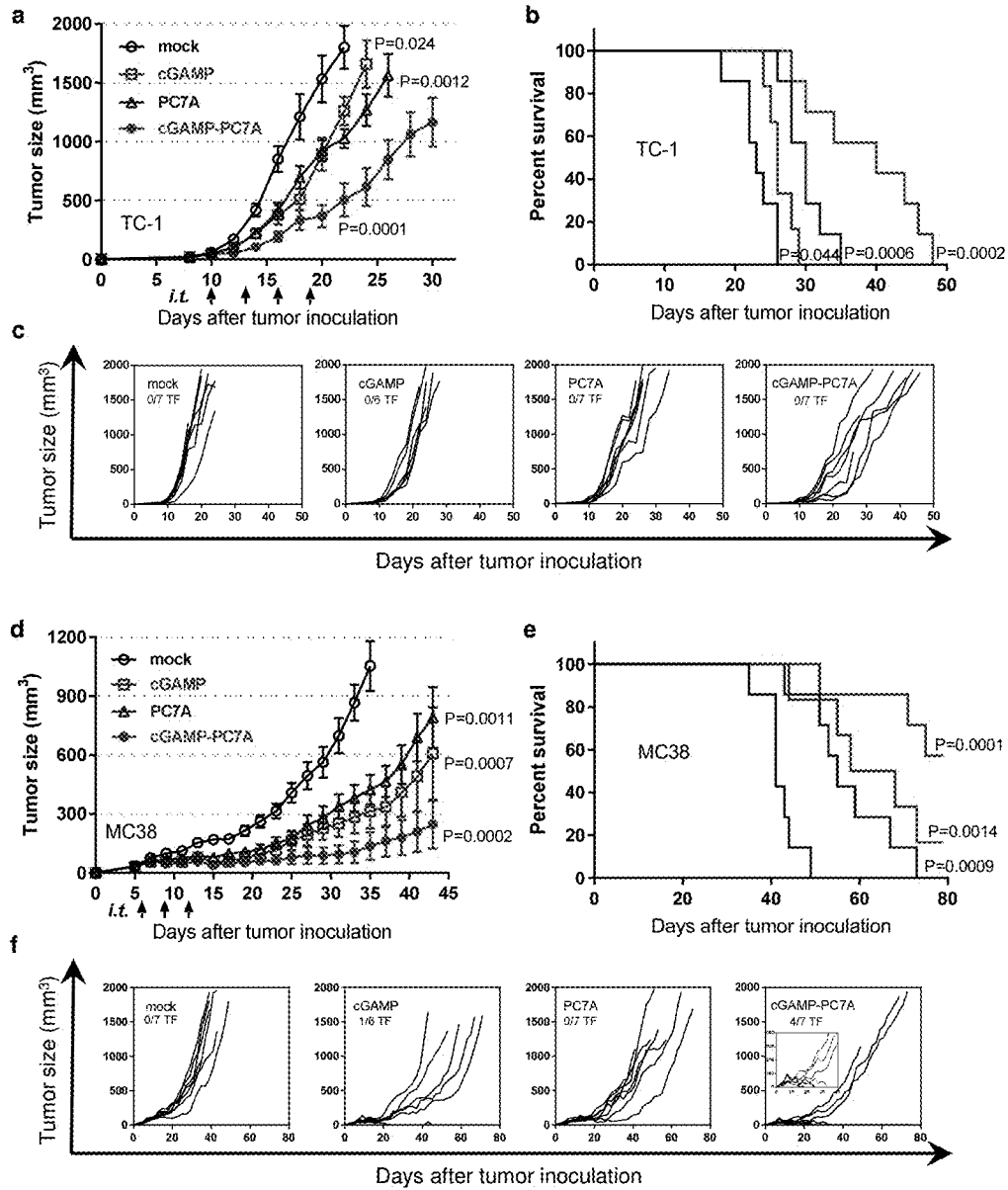
FIG. 5 displays that PC7A and cGAMP show synergistic antitumor efficacy in tumor-bearing mice. (a-c) TC-1 and (d-f) MC38 tumor-bearing mice were injected intratumorally with 5% glucose (mock), cGAMP (2.5 µg), PC7A (50 µg), or cGAMP-loaded PC7A nanoparticles at indicated time points. Mean tumor volume (a, d), Kaplan-Meier survival curves (b, e), and spider plots of individual tumor growth curves (c, f) are shown. PC7A NP or cGAMP alone offers some degree of immune protection. cGAMP-loaded PC7A NP confers a synergistic anti-tumor immune response, with significantly improved survival and 4 of 7 mice in the MC38 model tumor-free. In tumor growth studies, values represent mean±SEM, two-tailed Student's t-test (versus mock). In survival studies, Mantel-Cox test.

To evaluate the antitumor efficacy in animal tumor models, intratumoral injections of free cGAMP, PC7A NP, or cGAMP-loaded PC7A NP were performed when subcutaneous tumors reached 50 mm³ in size. Mice bearing the TC-1 tumors were injected four times (FIG. 5a-c) and those bearing murine colorectal MC38 tumors three times (FIG. 5d-f). Mice injected with a 5% glucose solution were used as a negative control (all treatment groups were prepared in 5% glucose solutions). In the TC-1 model, all mice in the control group died within 26 days. cGAMP or PC7A alone conferred a minor degree of immune protection, extending median survival by 4 or 8 days, respectively. The cGAMP-loaded PC7A NP group offered potent tumor growth inhibition and a significant survival benefit. Better therapeutic outcomes were observed in mice bearing the MC38 tumors, with 4 of 7 mice treated by cGAMP-loaded PC7A NP remaining tumor-free after 80 days.

Figure 15:
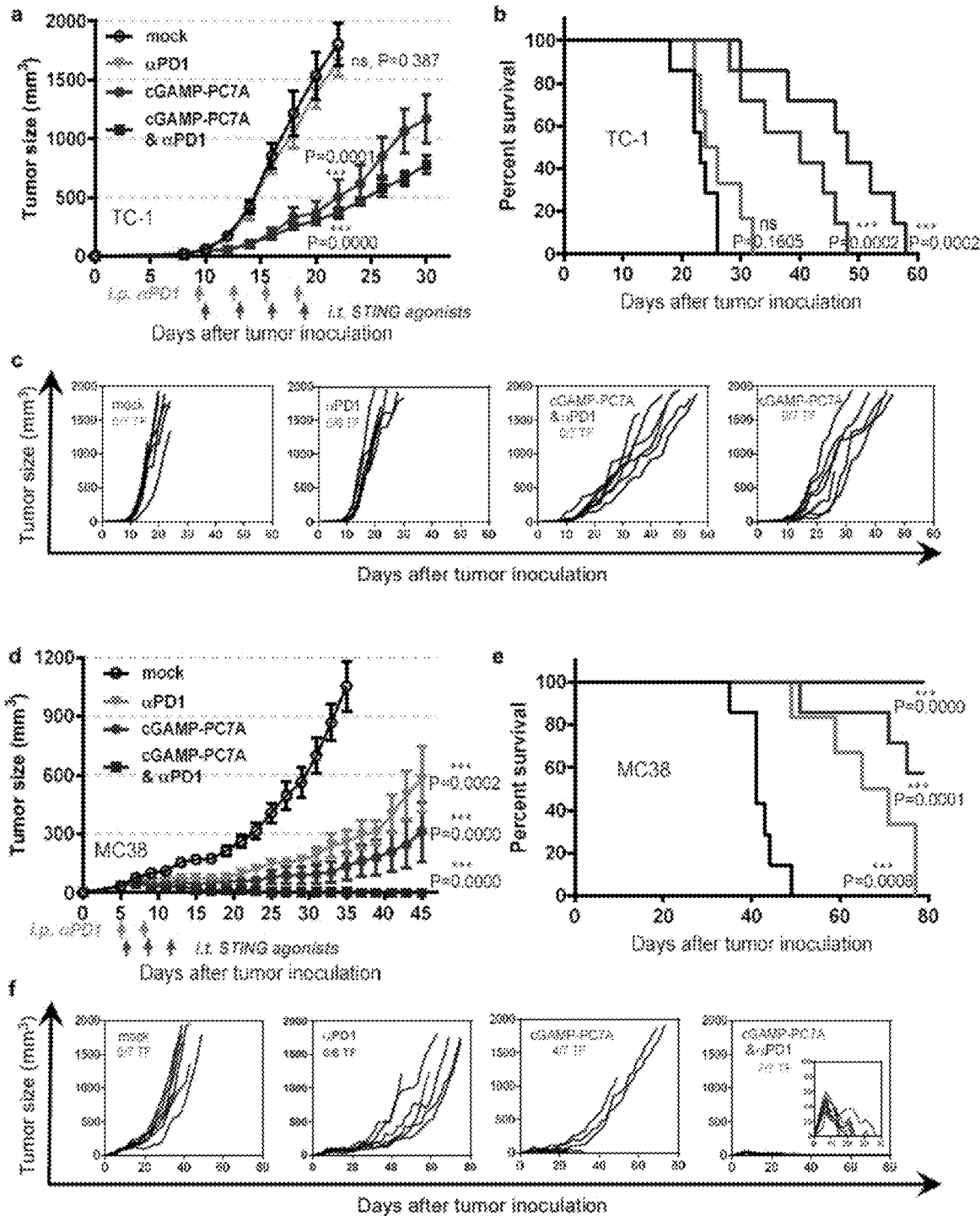
FIG. 15 shows that cGAMP-PC7A nanoparticle synergizes with anti-PD1 in immunotherapy of tumor-bearing animals. (a-c) TC1 and (d-f) MC38 tumor-bearing mice were injected intratumorally with 5% glucose (mock) or cGAMP-loaded PC7A NP, and injected intraperitoneally with saline or anti-PD1 (200 μg) at indicated time points. Mean tumor volume (a, d), Kaplan-Meier survival curves (b, e), and spider plots of individual tumor growth curves (c, f) are shown. cGAMP-PC7A NP treatment confers immune protection, rendering 4/7 MC38 mice tumor free, and further synergizes with anti-PD1 to achieve 100% cure rate in the MC38 model. In tumor growth studies, values represent mean±SEM, Two-tailed Student's t-test. In survival studies, Two-tailed Mantel-Cox test. ns, not significant; *, P<0.05, , P<0.01, *, P<0.001 versus 5% glucose group.
Figure 16:
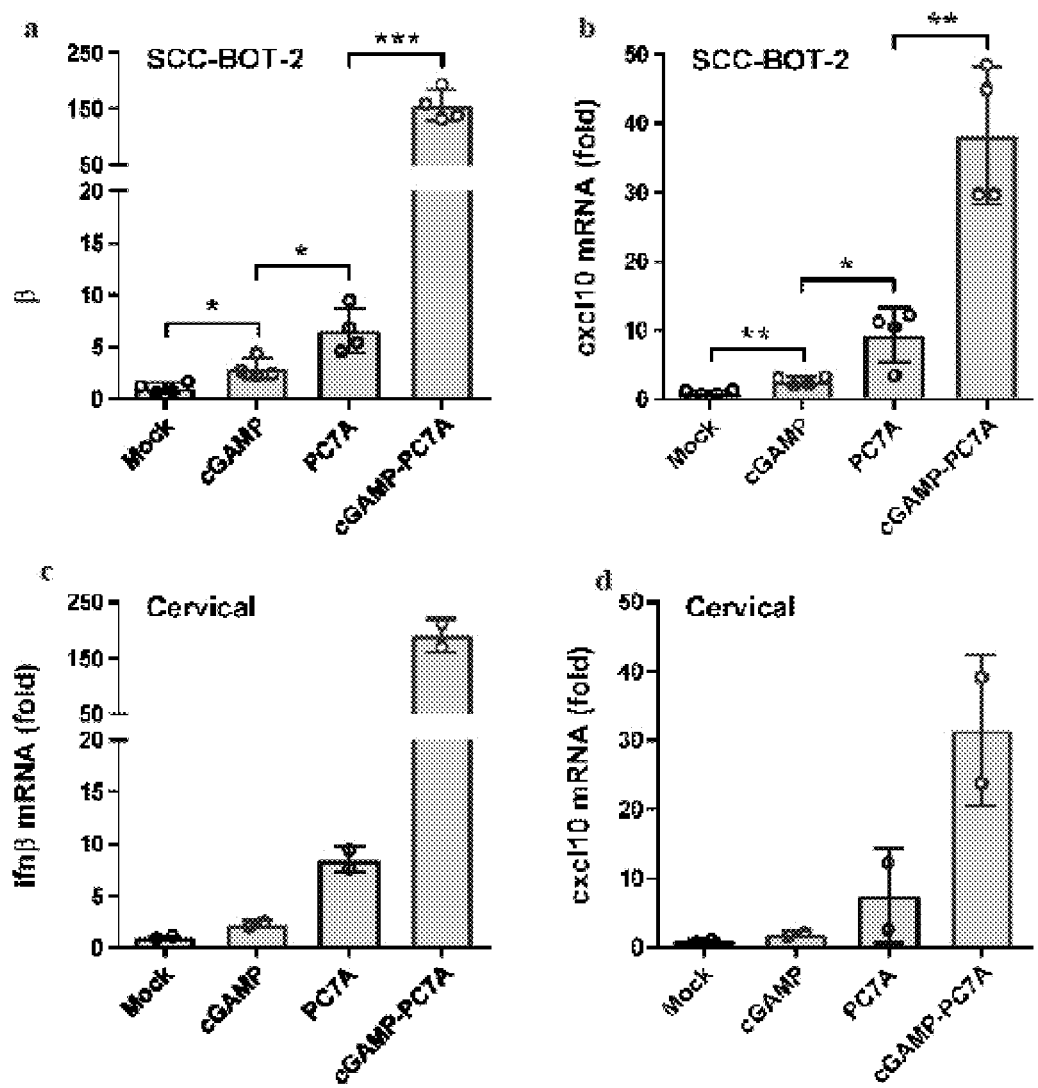
FIG. 16 displays that PC7A and cGAMP show synergistic effect in immune activation in additional human tumor tissues. Ifn-β and cxcl10 gene expression in fresh surgically resected squamous cell carcinoma from the base of tongue (SCC-BOT, second SCC patient from FIG. 6 in main text) (a, b) and cervical tumor tissues (c, d) after injection of 5% glucose, free cGAMP (80 ng), PC7A NPs (50 μg), or cGAMP-loaded PC7A NPs in 5% glucose solution. Values are mean±SD. Two-tailed Student's t-test: *, P<0.05, , P<0.01, *, P<0.001.
Figure 17:
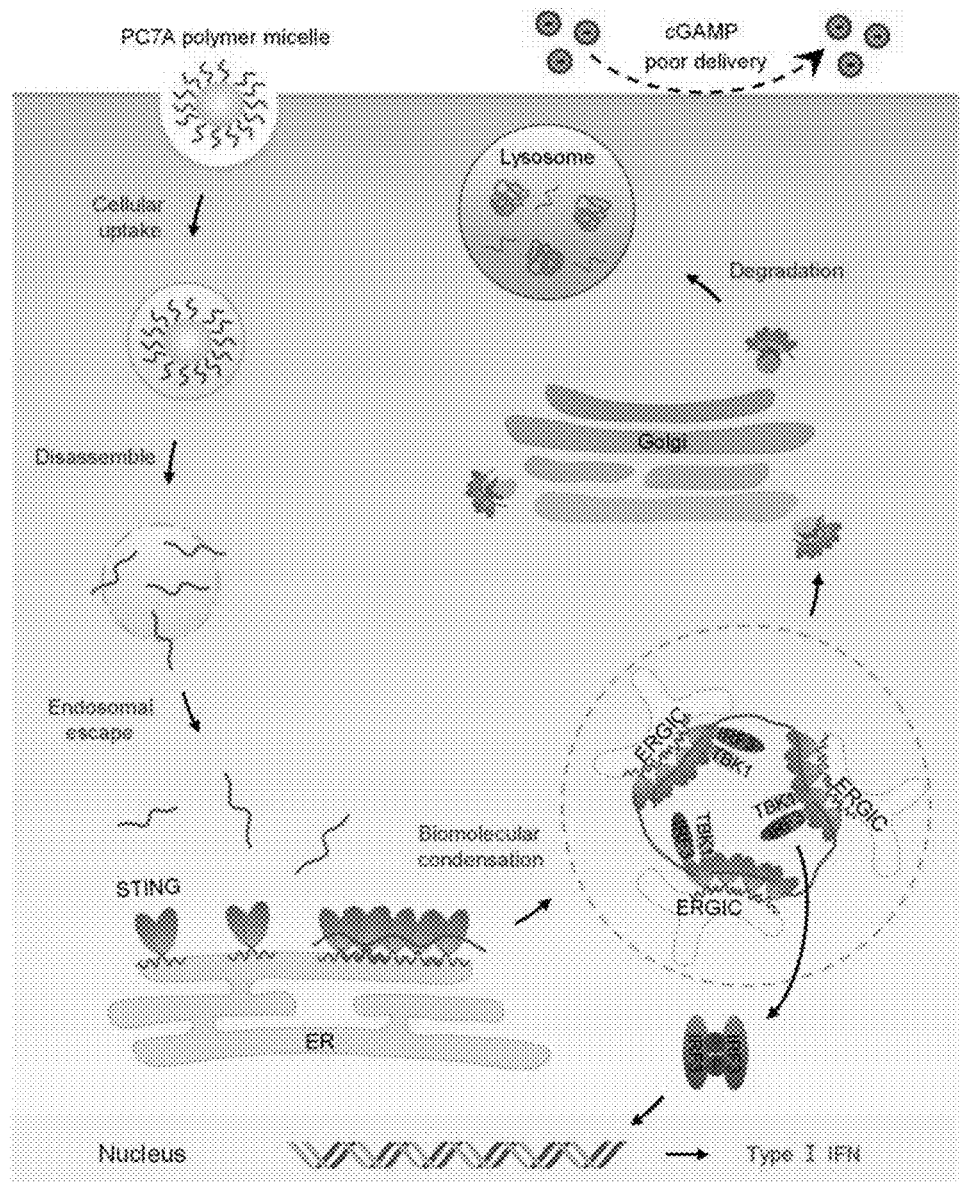
FIG. 17 displays a diagram of PC7A-induced STING phase condensation and immune activation. PC7A NP enter cells through endocytosis while dual negatively charged cGAMP molecules have limited cell permeability. Upon endosomal maturation and acidification below pH 6.9, PC7A NP disassembles into cationic unimers and escape from endo-lysosomes. In the cytosol, PC7A unimers bind to multiple STING molecules leading to STING oligomerization and condensation during translocation from ER to the ER-Golgi intermediate compartment (ERGIC) and the Golgi apparatus. In the process, STING condensates recruit and trigger the TBK1-IRF3 transcription cascade, leading to the production of type I interferons (IFN) and other proinflammatory cytokines. The activated STING is eventually transported to lysosomes for degradation.

Previous studies have shown an association between elevated type I IFN production and increased tumor infiltration of PD-1$^+$ cytotoxic T lymphocytes. STING activation by cGAMP-loaded PC7A NP may synergize with PD-1 blockade. The combination provided significantly improved efficacy, with over 50% of mice bearing TC-1 tumors surviving over 45 days (FIG. 15a-c). Combination cGAMP-PC7A NP and anti-PD-1 therapy conferred even stronger protection in the MC38 model, with 100% of mice remaining tumor-free after 80 days (FIG. 15d-f).

Figure 6:
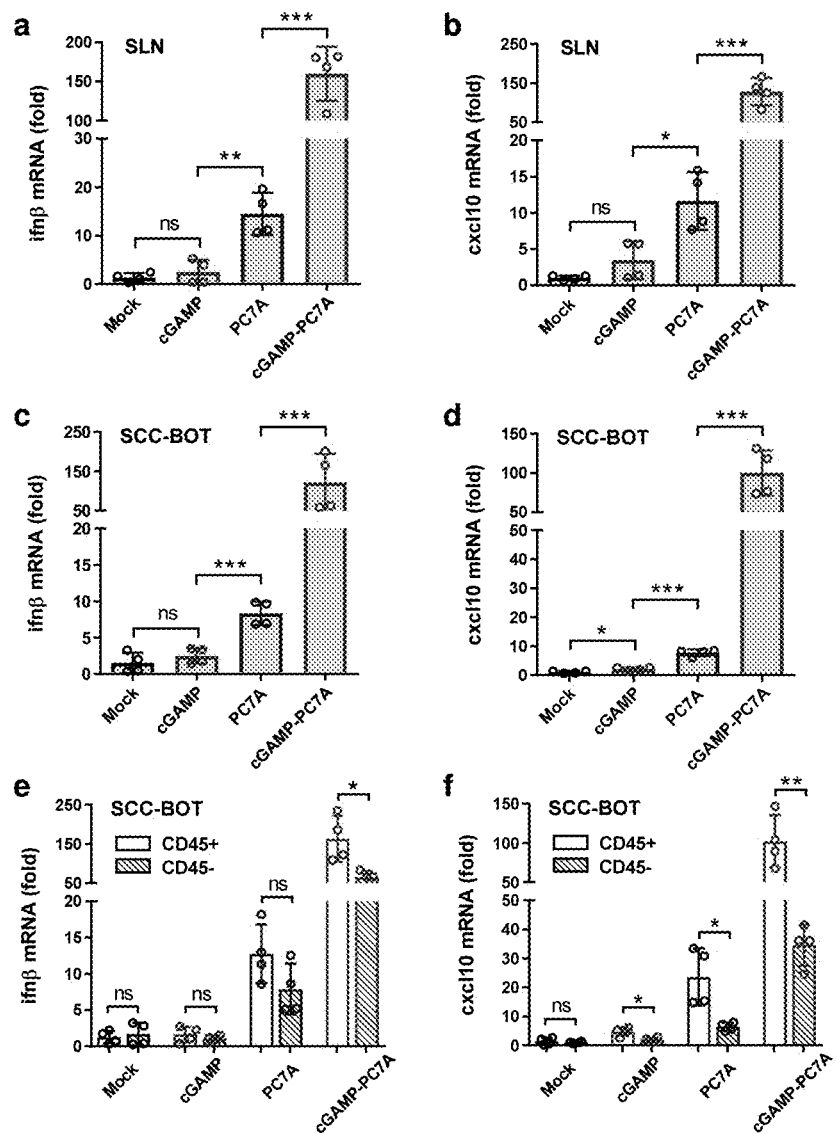
FIG. 6 displays that PC7A and cGAMP show synergistic STING activation in fresh human tissues. Free cGAMP alone is unable to activate STING, while PC7A NP and cGAMP-loaded PC7A NP demonstrate effective STING activation. Fresh surgically resected sentinel lymph node (SLN) (a, b) or squamous cell carcinoma from the base of tongue (SCC-BOT) (c-f) were divided into multiple sections (1-5 mm$^3$) and injected with 5% glucose, free cGAMP, PC7A NP, or cGAMP-loaded PC7A NP in 5% glucose solutions. Ifn-β and cxcl10 gene expressions were measured after 24 h incubation. (e, f) The CD45$^+$ cell population exhibits enhanced level of STING activation compared with CD45$^-$ cells. Values are mean±SD, n=4. Two-tailed Student's t-test: ns, not significant; *, P<0.05, , P<0.01, *, P<0.001.

To explore the translational potential, STING activation was investigated in human tissues. Freshly resected squamous cell carcinoma from the base of tongue, cervical tumor tissues, and a sentinel lymph node were injected with cGAMP, PC7A NP, or cGAMP-loaded PC7A NP, incubated in cell culture medium for 24 h at 37° C., and IFN related gene expression was detected. Free cGAMP had a marginal effect on ifn-β and cxcl10 mRNA expressions over the control due to limited bioavailability. In contrast, PC7A NP elevated downstream signals by 5-20 folds. An increase of cytokine expression (100-200 folds, FIG. 6a-d and FIG. 16) was observed with cGAMP-loaded PC7A NP in all tissue types. CD45$^+$ myeloid cell populations in the tumor showed higher level of STING activation by PC7A NP and cGAMP-loaded PC7A NP treatment over CD45$^-$ cells (FIG. 6e, f), indicating that leukocytes, instead of cancer cells, are the primary targets for STING-mediated immunomodulation by nanoparticles.

The intratumoral injection of PC7A and cGAMP has therefore been observed to provide an unexpected synergistic anti-tumor efficacy. The present inventors believe that delivery of cGAMP using PC7A and analogous STING activating polymers is most effective with intratumoral injection. The inventors have observed that the synergistic activity observed through delivery of cGAMP using STING activating polymers is less pronounced with subcutaneous injection proximate the tumor, and not present with intravenous injection. Accordingly, administration of STING activating pH sensitive polymers, such as PC7A, with non-peptide STING agonist, such as cGAMP, either subcutaneously proximate a tumor or intratumorally is disclosed.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A pharmaceutical composition comprising:
   (i) a block copolymer of Formula (I), or a pharmaceutically acceptable salt, solvate, or hydrate thereof:

(I)

wherein:
   $n_1$ is an integer from 10-200;
   $x_1$ is an integer from 20-300;
   $y_1$ is an integer from 0-10;
   X is a halogen, —OH, or —C(O)OH;
   r denotes randomness in the order of $x_1$ and $y_1$ blocks in the block copolymer;
   $R^1$ and $R^2$ are each independently hydrogen or optionally substituted $C_1$-$C_6$ alkyl;
   $R^3$ and $R^4$ are each independently an optionally substituted $C_1$-$C_6$ alkyl, $C_3$-$C_{10}$ cycloalkyl or aryl;
   or $R^3$ and $R^4$ are taken together with the corresponding nitrogen to which they are attached form an optionally substituted 5 to 7-membered ring;
   $R^5$ is hydrogen or —C(O)CH$_3$; and
   (ii) a non-peptide STING agonist.

2. The pharmaceutical composition of claim 1, wherein $R^1$ and $R^2$ are each independently an optionally substituted $C_1$-$C_6$ alkyl.

3. The pharmaceutical composition of claim 1, wherein, wherein $R^3$ and $R^4$ are each independently an optionally substituted $C_1$-$C_6$ alkyl.

4. The pharmaceutical composition of claim 1, wherein $R^3$ and $R^4$ are taken together with the corresponding nitrogen to which they are attached form an optionally substituted 5 to 7-membered ring.

5. The pharmaceutical composition of claim 1, wherein $y_1$ is 0.

6. The pharmaceutical composition of claim 1, wherein the block copolymer of Formula (I) has the structure of Formula (Ia), or a pharmaceutically acceptable salt, solvate, or hydrate thereof:

(Ia)

7. The pharmaceutical composition according to any one of claims 1, 2, 3, 4, 5, and 6, wherein the non-peptide STING agonist is a cyclic dinucleotide.

8. The pharmaceutical composition according to any one of claims 1, 2, 3, 4, 5, and 6, wherein the non-peptide STING agonist is cGAMP.

9. The pharmaceutical composition of claim 7, wherein the cyclic dinucleotide is a compound having the structure of Formula (IIa) or Formula (IIb), or a pharmaceutically acceptable salt, solvate or hydrate thereof:

(IIa)

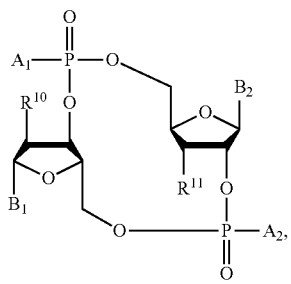
(IIb)
wherein
A¹ and A² are each independently OH or SH;
B¹ and B² are each independently guanine or adenine;
$R^{10}$ is H, halogen, OH, OCH₃; and
$R^{11}$ is halogen or OH.
10. The pharmaceutical composition of claim 7, wherein the cyclic dinucleotide is a compound selected from:
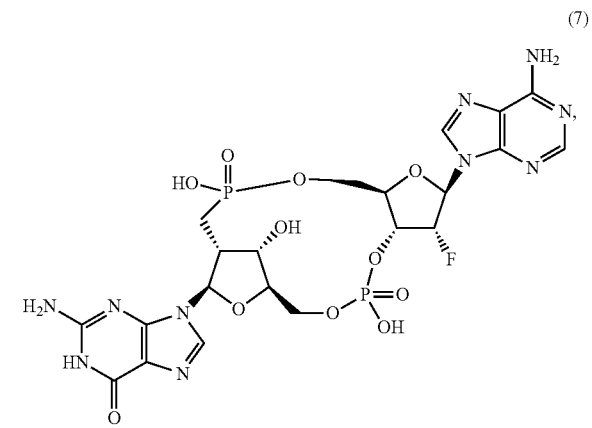
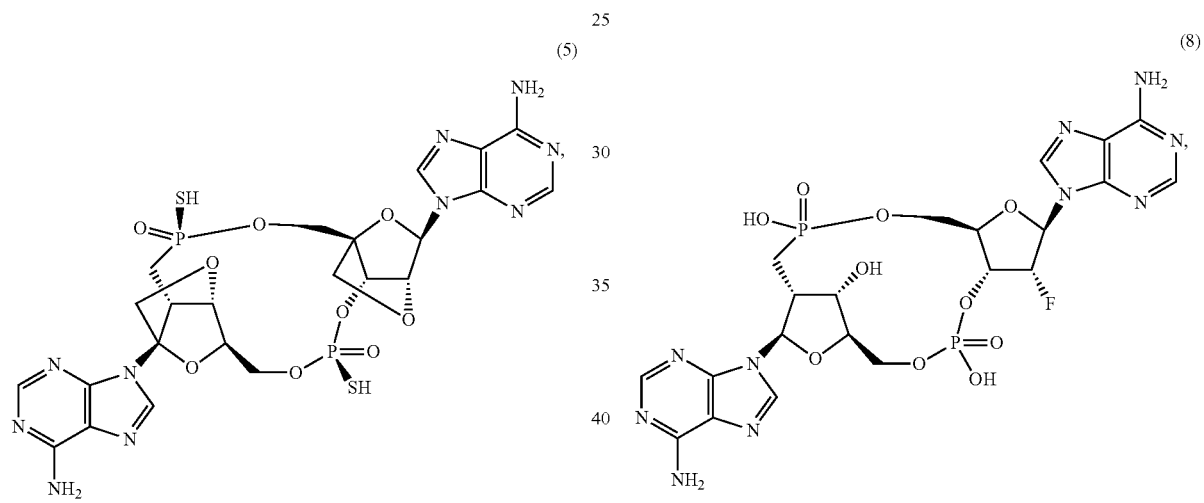
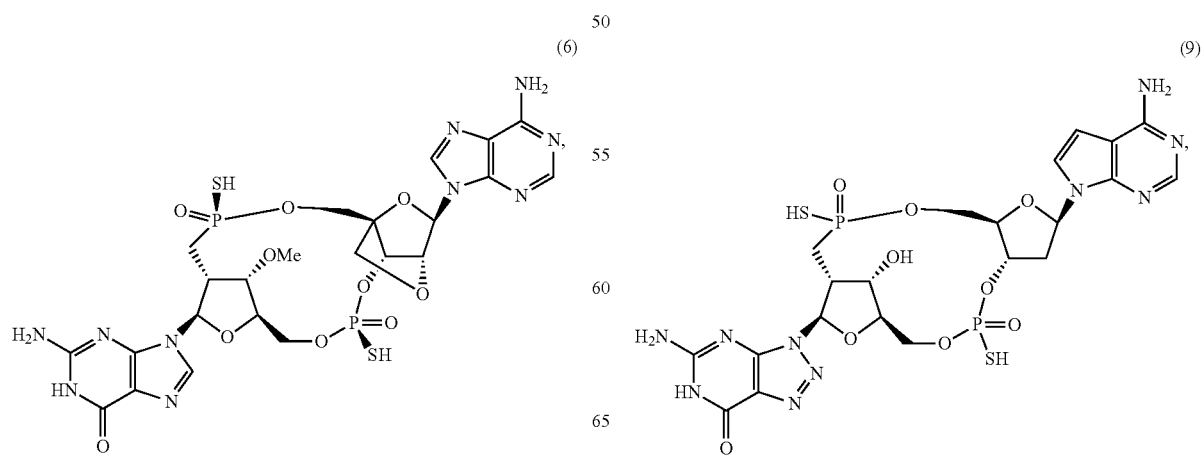

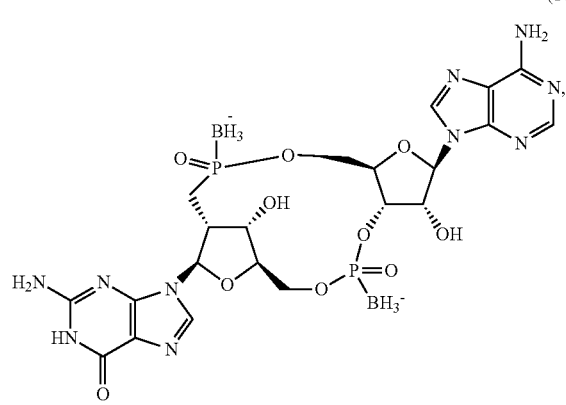
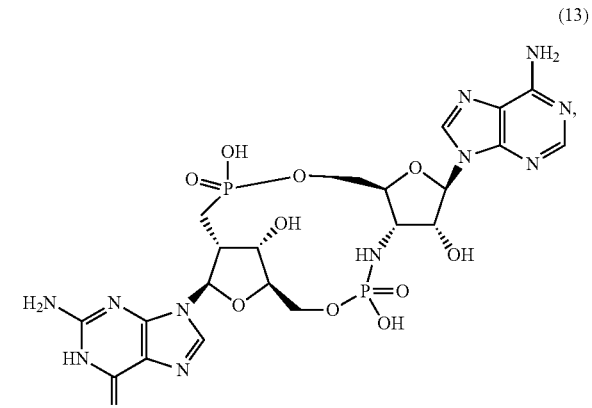
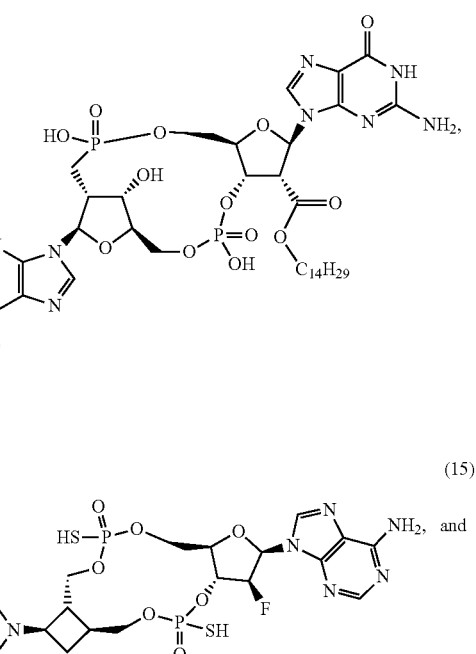
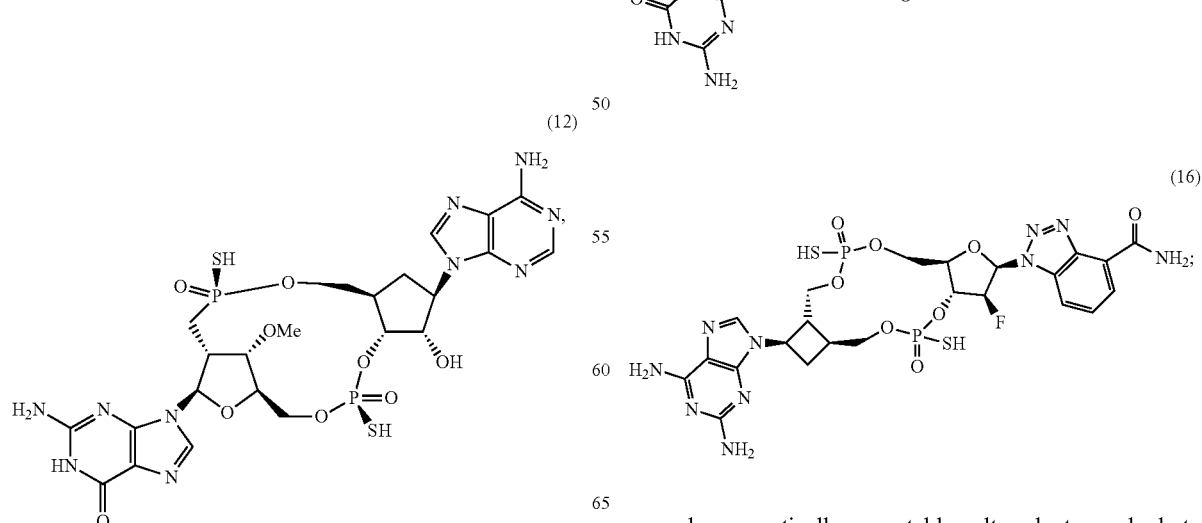
or a pharmaceutically acceptable salt, solvate, or hydrate thereof.

11. The pharmaceutical composition of claim 7, wherein the cyclic dinucleotide is selected from:
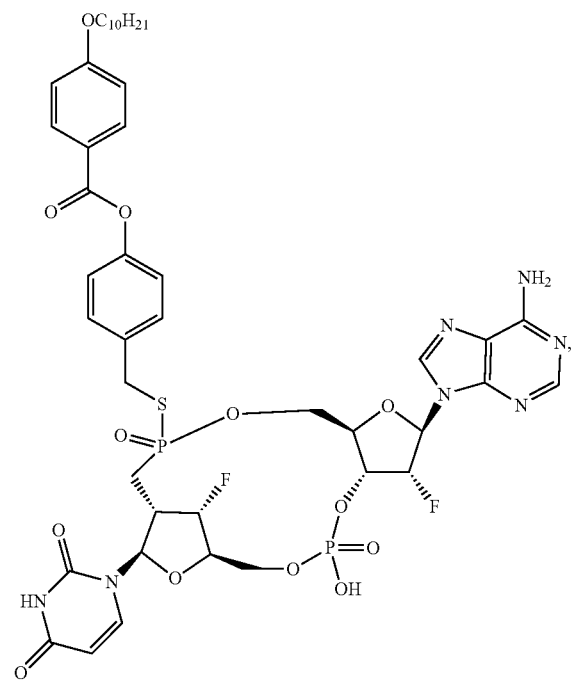
(17)
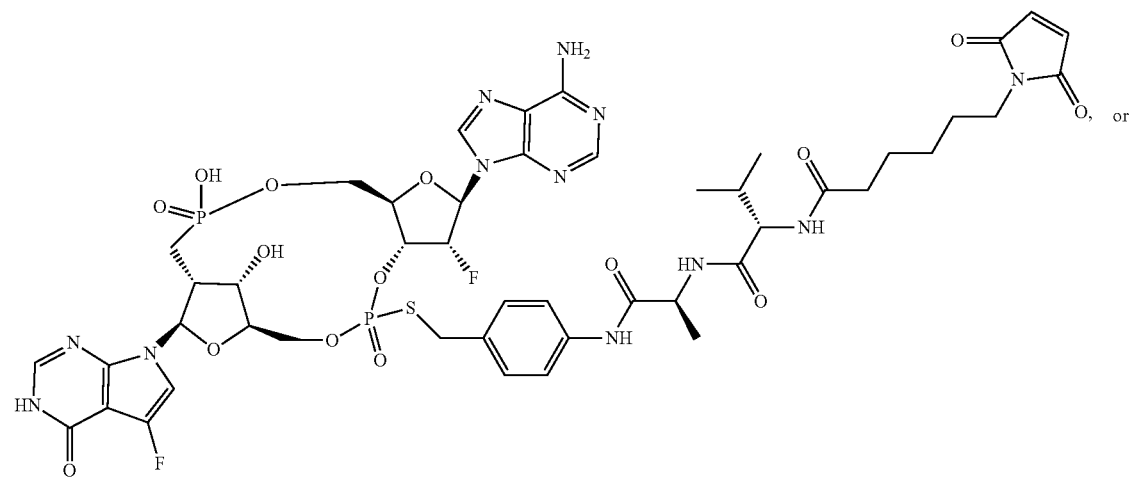
(18), or

(19)
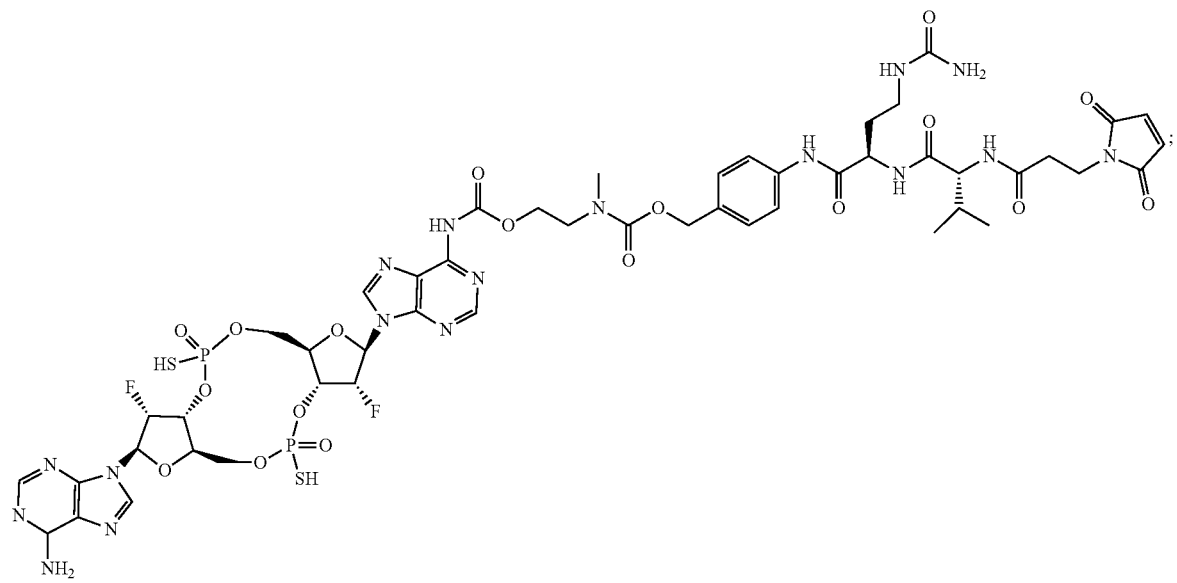
or a pharmaceutically acceptable salt, solvate, or hydrate thereof.
12. The pharmaceutical composition of claim 1, wherein the non-peptide STING agonist is selected from:
(FAA)
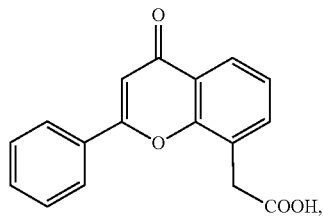
(CMA)
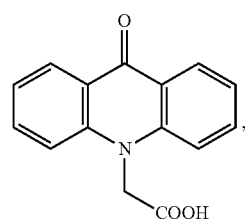
(α-Mangostin)
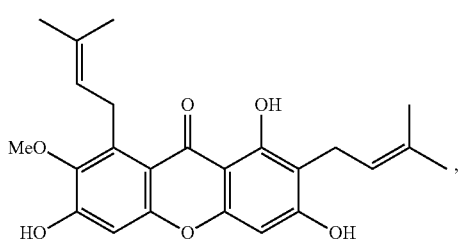
-continued
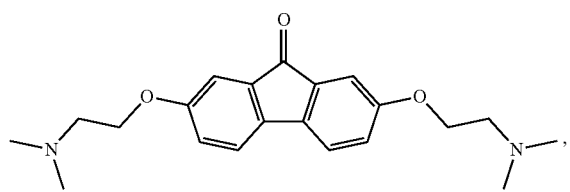
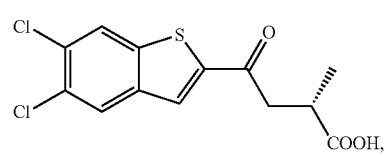
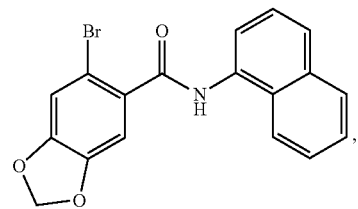
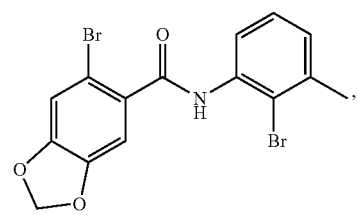

-continued

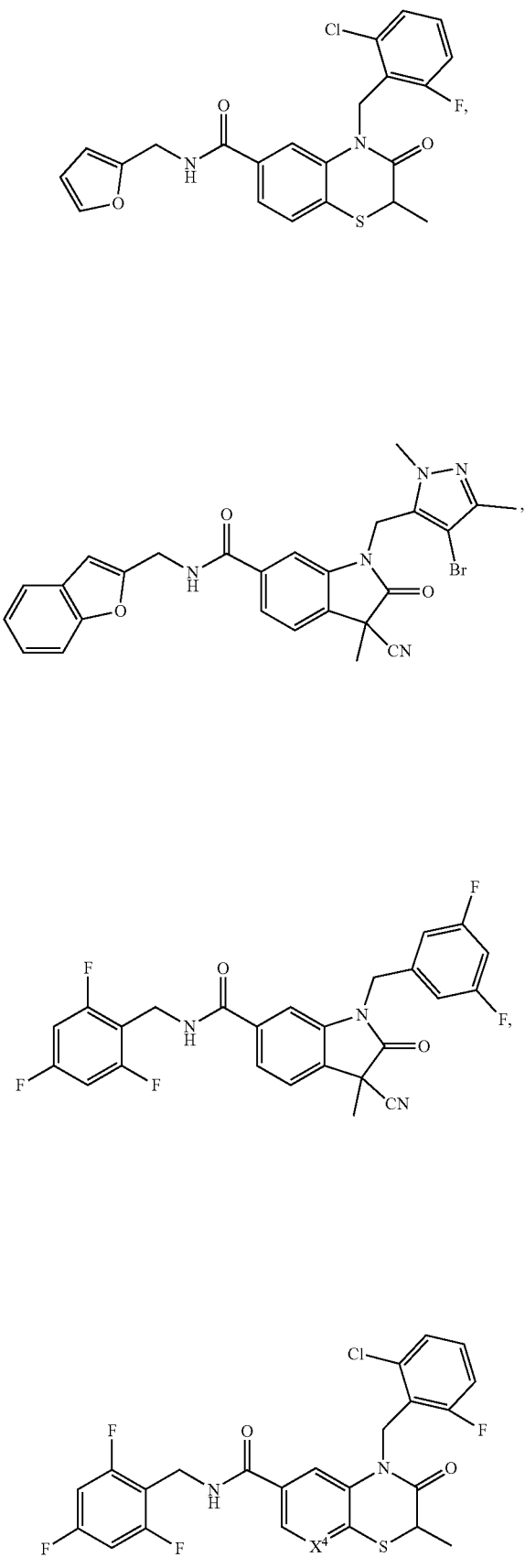

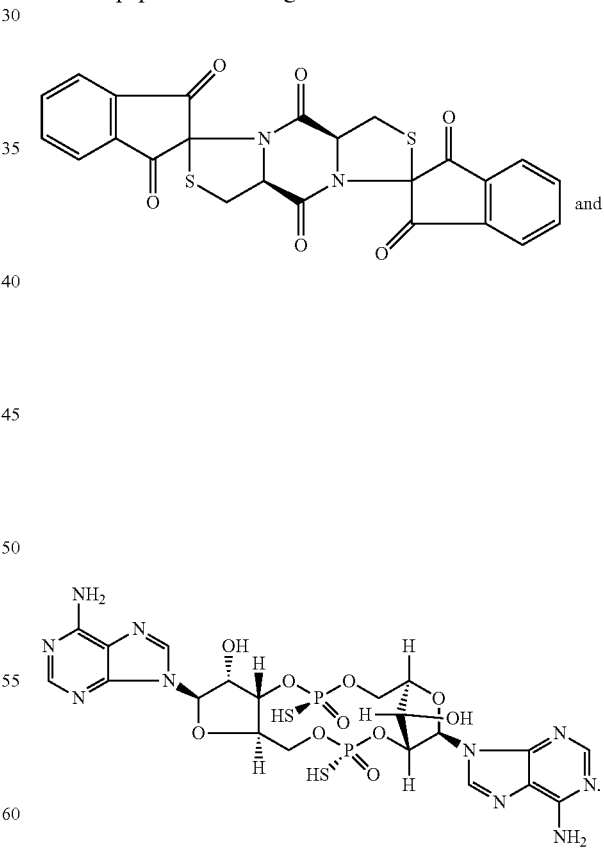

wherein $X^4$ is CH or N; and or $CH_3$;

wherein $X^5$ is CH or N and $Y^4$ is $NH_2$ or a pharmaceutically acceptable salt, solvate, or hydrate thereof.

13. The pharmaceutical composition of claim 1, wherein the non-peptide STING agonist is selected from:

and

14. The pharmaceutical composition of claim 1, wherein the non-peptide STING agonist is a compound having the structure of Formula (IV), or a pharmaceutically acceptable salt, solvate, or hydrate thereof:

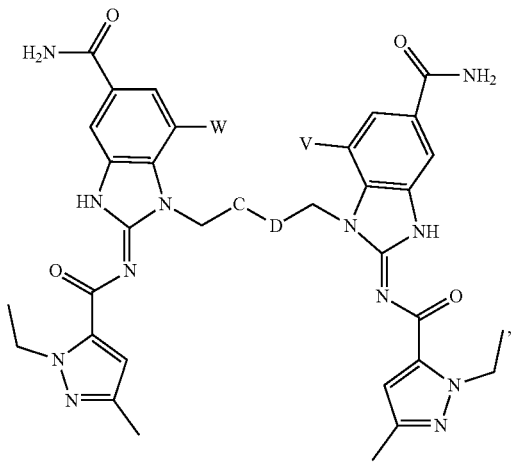

(IV)

wherein:
C-D is an alkylene or alkenylene;
W is H or —OCH$_3$; and
V is H or —O—(C$_1$-C$_3$)alkyl-(C$_3$-C$_6$)heterocycle.

15. The pharmaceutical composition of claim 1, wherein the non-peptide STING agonist is:

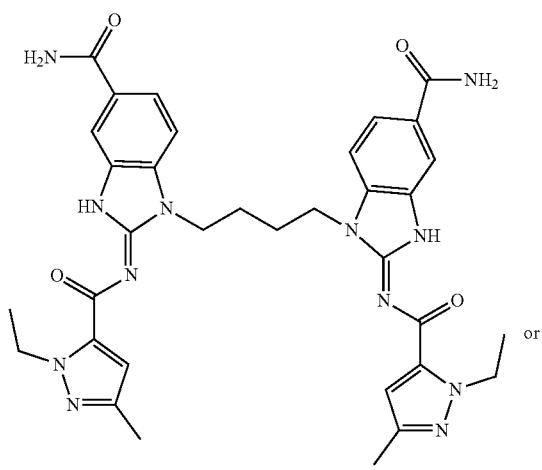

or

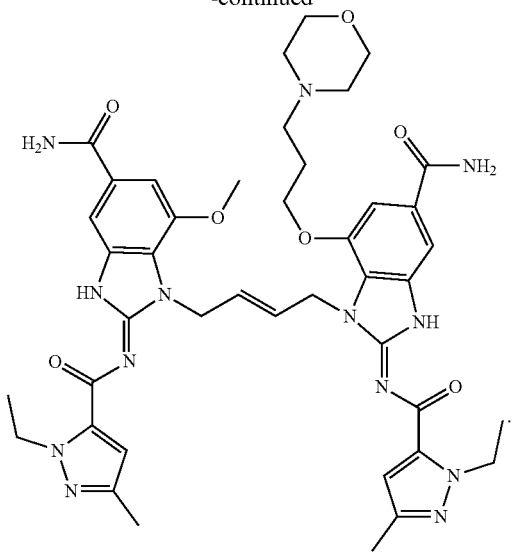

16. The pharmaceutical composition of claim 1, wherein one or more non-peptide STING agonists is encapsulated by the block copolymer within one or more micelles.

17. The pharmaceutical composition of claim 1, wherein one or more non-peptide STING agonists is not encapsulated by the block copolymer within a micelle.

18. The pharmaceutical composition of claim 17, further comprising a saccharide solution.

19. A method for treating cancer in a subject in need thereof, comprising administering to the subject a therapeutically effective amount of a pharmaceutical composition of claim 1.

20. A method of activating the STING pathway in a subject comprising administering to the subject in need thereof a pharmaceutical composition of claim 1.

* * * * *

UNITED STATES PATENT AND TRADEMARK OFFICE
CERTIFICATE OF CORRECTION

PATENT NO. : 12,036,319 B2
APPLICATION NO. : 17/469111
DATED : July 16, 2024
INVENTOR(S) : Jinming Gao and Suxin Li It is certified that error appears in the above-identified patent and that said Letters Patent is hereby corrected as shown below:

In the Claims

Claim 14, Column 67, Line 22, delete "C-D"; and insert --C—D-- therefor.

Claim 14, Column 67, Line 24, delete "—O—(C1-C3)alkyl-(C3-C6)heterocycle"; and insert -- —O—(C1-C3)alkyl—(C3-C6)heterocycle-- therefor.

Signed and Sealed this
Seventeenth Day of September, 2024

Katherine Kelly Vidal
Director of the United States Patent and Trademark Office